United States Patent
Noble et al.

(10) Patent No.: US 10,705,074 B2
(45) Date of Patent: Jul. 7, 2020

(54) TARGETING FIBROBLAST INVASION FOR PULMONARY FIBROSIS

(71) Applicant: CEDARS-SINAI MEDICAL CENTER, Los Angeles, CA (US)

(72) Inventors: Paul W. Noble, Beverly Hills, CA (US); Dianhua Jiang, Encino, CA (US); Carol Jiurong Liang, Encino, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 346 days.

(21) Appl. No.: 15/761,404

(22) PCT Filed: Sep. 26, 2016

(86) PCT No.: PCT/US2016/053743
§ 371 (c)(1),
(2) Date: Mar. 19, 2018

(87) PCT Pub. No.: WO2017/053952
PCT Pub. Date: Mar. 30, 2017

(65) Prior Publication Data
US 2019/0170732 A1    Jun. 6, 2019

Related U.S. Application Data

(60) Provisional application No. 62/232,864, filed on Sep. 25, 2015.

(51) Int. Cl.
C12N 15/11         (2006.01)
G01N 33/50         (2006.01)

(52) U.S. Cl.
CPC ..... *G01N 33/5044* (2013.01); *G01N 2500/02* (2013.01); *G01N 2800/12* (2013.01)

(58) Field of Classification Search
None
See application file for complete search history.

(56) References Cited

U.S. PATENT DOCUMENTS

2014/0050740 A1   2/2014 Noble et al.
2015/0258192 A1   9/2015 Brophy et al.

OTHER PUBLICATIONS

Bolaños et al., Role of Sonic Hedgehog in Idiopathic Pulmonary Fibrosis, Am J Physiol Lung Cell Mol Physiol 303, Sep. 28, 2012, 978-990.
Chilosi et al, Migratory marker expression in fibroblast foci of idiopathic pulmonary fibrosis, Respiratory Research Biomed Central LTD, London, GB 7:1 2006.
Martinez, E. Multi-protein complexes in eukaryotic gene transcription. Plant Mol. Biol. 50: 925-47 (2002).
Martinez, F.O., et al. The M1 and M2 paradigm of macrophage activation: time for reassessment. F1000Prime Rep. 2014; 6:13.
Mason, R.J. Biology of alveolar type II cells. Respirology. Jan. 2006; 11 Suppl: S12-5.
McDonald, S. et al. Combined betaseron R (recombinant human interferon beta) and radiation for inoperable non-small cell lung cancer. Radiother Oncol. Mar. 1993; 26(3): 212-8.
McQualter, J.L., et al. Concise Review: Deconstructing the Lung to Reveal Its Regenerative Potential. Stem Cells. May 2012; 30(5): 811-6.
McQualter, J.L., et al. Endogenous Fibroblastic Progenitor Cells in the Adult Mouse Lung Are Highly Enriched in be Sca-1 Positive Cell Fraction. Stem Cells. 2009; 27: 612-22.
McQualter, J.L., et al. Evidence of an epithelial stem/progenitor cell hierarchy in the adult mouse lung. Proc Natl Acad Sci USA 2010; 107: 1414-19.
Meltzer, E.B., et al., Idiopathic pulmonary fibrosis. Orphanet J Rare Dis. Mar. 26, 2008; 3: 8. doi:10.1186/1750-1172-3-8.
Mentink-Kane, M.M., et al. Accelerated and Progressive and Lethal Liver Fibrosis in Mice that Lack Interleukin (IL)-10, IL-12p40, and IL-13R ?2.Gastroenterology. Dec. 2011; 141(6): 2200-9.
Mentink-Kane, M.M., et al. Opposing roles for IL-13 and IL-13 receptor a2 in health and disease. Immunol Rev. Dec. 2004; 202: 191-202.
Mikecz, K., et al. Anti-CD44 treatment abrogates tissue oedema and leukocyte infiltration in murine arthritis . . . Nat Med. Jun. 1995; 1(6): 558-63.
Minshall, E.M., et al. Eosinophil-associated TGF-beta1 mRNA expression and airways fibrosis in bronchial asthma . . . Am J Respir Cell Mol boil. Sep. 1997; 17(3): 326-33.
Miyazaki, Y. et al. Expression of a Tumor Necrosis Factor-a Transgene in Murine Lung Causes Lymphocytic and Fibrosing Alveolitis a Mouse Model of Progressive Pulmonary Fibrosis. J Clin Invest. Jul. 1995; 96(1): 250-9.
Moeller, A., et al. Circulating Fibrocytes Are an Indicator of Poor Prognosis in Idiopathic Pulmonary Fibrosis. Am J Respir Crit Care Med. Apr. 1, 2009; 179(7): 588-94.
Monroe, D.M., et al. Platelets and Thrombin Generation. Arterioscler Thromb Vasc Biol. 2002; 22:1381-1389.
Moore, B.B. et al. Murine models of pulmonary fibrosis. Am J Physiol Lung Cell Mol Physiol. Feb. 2008; 294(2): L152-60.
Moore, B.B. et al. Animal Models of Fibrotic Lung Disease. Am J Respir Cell Mol Biol. Aug. 2013; 49(2): 167-79.
Morrisey, E.E.,et al. Preparing for the First Breath: Genetic and Cellular Mechanisms in Lung Development. Dev Cell. Jan. 19, 2010; 18(1): 8-2.
Muggia, F. et al., Pulmonary toxicity of antitumor agents. Cancer Treat Rev, 10: 221-243, 1983.
Mukherjee, A.B, et al. Uteroglobin: A Steroid-Inducible Immunomodulatory Protein That Founded the Secretoglobin Superfamily. Endocr Rev. Dec. 2007; 28(7): 707-25.
Murray, L.A., et al. Hyper-responsiveness of IPF/UIP fibroblasts: interplay between TGFbeta1, IL-13 and CCL2. Int J Biochem Cell Biol. 2008; 40(10): 2174-82.

(Continued)

*Primary Examiner* — Ekaterina Poliakova-Georgantas
*Assistant Examiner* — Ekaterina Poliakova
(74) *Attorney, Agent, or Firm* — McCarter & English, LLP; Beverly W. Lubit

(57) ABSTRACT

The described invention provides a method for identifying a therapeutic compound effective to reduce invasiveness of fibroblasts characterized by a highly invasive phenotype obtained from a subject with idiopathic pulmonary fibrosis.

2 Claims, 7 Drawing Sheets

Specification includes a Sequence Listing.

(56) References Cited

OTHER PUBLICATIONS

Mushiroda, T., et al. A genome-wide association study identifies an association of a common variant in TERT with susceptibility to idiopathic pulmonary fibrosis. J Med Genet. Oct. 2008; 45(10): 654-6.
Myers, J.L., et al. Epithelial Necrosis and Alveolar Collapse in the Pathogenesis of Usual Interstitial Pneumonia. Chest. Dec. 1988; 94(6): 1309-11.
Nelson, A.L., "Antibody fragments," Mabs 2010, 2(1): 77-83.
Nobel, P. W., et al. Hyaluronate Activation of CD44 Induces Insulin-like Growth Factor-1 Expression by a Tumor Necrosis Factor-alpha-dependent Mechanism in Murine Macrophages. J Clin Invest. Jun. 1993; 91(6): 2368-77.
Noble, P.W., et al. Pulmonary fibrosis: patterns and perpetrators J Clin Invest. Aug. 2012; 122(8): 2756-62.
Ogawa, T., et al. Suppression of type I collagen production by microRNA-29b in cultured human stellate cells. Biochem Biophys Res Commun. Jan. 1, 2010; 391(1): 316-21.
Osterreicher, C.H., et al. Fibroblast-specific protein 1 identifies an inflammatory subpopulation of macrophages in he liver. Proc Natl Acad Sci USA. Nov. 23, 2010; 108(1): 308-13.
Paddison, P.J. et al. (2002) Stable suppression of gene expression by RNAi in mammalian cells. PNAS 99 (3):1443-1448.
Pardo, A.,et al. Up-Regulation and Profibrotic Role of Osteopontin in Human Idiopathic Pulmonary Fibrosis. PLoS Med. Sep. 2005; 2(9): e251.
Paul, C.P. et al. (2002) Effective expression of small interfering RNA in human cells. Nature Biotechnology 20(5):505-508.
Paulin, D., et al. Desmin: a major intermediate filament protein essential for the structural integrity and function of muscle.Exp Cell Res. Nov. 15, 2004; 301(1): 1-7.
Peterson, M.W., et al. Prognostic Role of Eosinophils in Pulmonary Fibrosis. Chest. Jul. 1987; 92(1): 51-6.
Phan, S. et al., A Comparative Study of Pulmonary Fibrosis Induced by Bleomycin and an O2 Metabolite Producing Enzyme System. Chest., 83(5 Suppl):44S-45S, 1983.
Phan, S. et al., Bleomycin-induced Pulmonary Fibrosis in Rats: Biochemical Demonstration of Increased Rate of Collagen Synthesis. Am Rev Respir Dis 121: 501-506, 1980.
Phillips, R.J., et al. Circulating fibrocytes traffic to the lungs in response to CXCL12 and mediate fibrosis. J Clin Invest. Aug. 2004; 114(3): 438-46.
Piguet, P.F., et al. Expression and Localization of Tumor Necrosis Factor-alpha and Its mRNA in Idiopathic Pulmonary Fibrosis. Am J Pathol. Sep. 1993; 143(3): 651-655.
Piguet, P.F., et al. Tumor necrosis factor/cachectin plays a key role in bleomycin-induced pneumopathy and fibrosis. J Exp Med. Sep. 1, 1989; 170(3): 655-63.
Piguet. P.F., et al. Requirement of tumour necrosis factor for development of silica induced pulmonary fibrosis. Nature. Mar. 15, 1990; 344(6263): 245-7.
Pontoglio, M. et al., Hepatocyte Nuclear Factor 1 Inactivation Results in Hepatic Dysfunction, Phenylketonuria, and Renal Fanconi Syndrome. Cell 84: 575-85 (1996).
Prasse, A. et al. Serum CC-Chemokine Ligand 18 Concentration Predicts Outcome in Idiopathic Pulmonary Fibrosis. Am J Respir Crit Care Med. Apr. 15, 2009; 179(8): 717-23.
Rafii, R., et al. A review of current and novel therapies for idiopathic pulmonar fibrosis. J Thorac Dis. 2013; 5(1): 48-73.
Raghu, G., et al. Incidence and Prevalence of Idiopathic Pulmonary Fibrosis. Am J Respir Crit Care Med. Oct. 1, 2006; 174(7): 810-6.
Ramalingam, T.R., et al. Unique functions of the type II interleukin 4 receptor identified in mice lacking the interleukin 13 receptor ?1 chain. Nat Immunol. Jan. 2008; 9(1): 25-33.
Ramasamy, S. K., et al. Fgf10 dosage is critical for the amplification of epithelial cell progenitors and for the formation of multiple mesenchymal lineages during lung development. Dev Biol. Jul. 15, 2007; 307(2): 237-47.

Ramirez, A.M., et al. Myofibroblast Transdifferentiation in Obliterative Bronchiolitis: TGF-beta Signaling Through Smad3-Dependent and -Independent Pathways. Am J Transplant. Sep. 2006; 6(9): 2080-8.
Ramos, C. et al. Fibroblasts from Idiopathic Pulmonary Fibrosis and Normal Lungs Differ in Growth Rate, Apoptosis, and Tissue Inhibitor of Metalloproteinases Expression. Am J Respir Cell Mol Biol. May 2001; 24(5): 591-8.
Reiman, R.M., et al. Interleukin-5 (IL-5) Augments the Progression of Liver Fibrosis by Regulating IL-13 Activity. Infect Immun. Mar. 2006; 74(3): 1471-9.
Richards,T.J., et al. Peripheral Blood Proteins Predict Mortality in Idiopathic Pulmonary Fibrosis.Am J Respir Crit Care Med. Jan. 1, 2012; 185(1): 67-76.
Roberts, S.N. et al. A novel model for human interstitial lung disease: Hapten-driven lung fibrosis in rodents. J Pathol. Jul. 1995; 176(3): 309-18.
Rock, J.R., et al. Multiple stromal populations contribute to pulmonary fibrosis without evidence for epithelial to mesenchymal transition. Proc Natl Acad Sci USA. Dec. 27, 2011; 108(52): E1475-83.
Rosas, I.O., et al. MMP1 and MMP7 as Potential Peripheral Blood Biomarkers in Idiopathic Pulmonary Fibrosis. PLoS Med. Apr. 29, 2008; 5(4): e93.
Ross, J.S. et al. miRNA The New Gene Silencer, Am J Clin Pathol. 2007; 128(5): 830-36.
Rothman, B.L., et al. Cytokine regulation of C3 and C5 production by the human type II pneumocyte cell line, A549. J Immunol. 1990; 145: 592-598.
Sanders, S.L. et al., Molecular Characterization of *Saccharomyces cerevisiae* TFIID. Mol Cell. Biol. 22: 6000-6013 (2002).
Sanders, S.L., et al. Identification of Two Novel TAF Subunits of the Yeast *Saccharomyces cerevisiae* TFIID Complex. J Biol. Chem. 275: 13895-900 (2000).
Satelli, A., et al. Vimentin as a potential molecular target in cancer therapy or Vimentin, an overview and its potential as a molecular target for cancer therapy. Cell Mol Life Sci. Sep. 2011; 68(18): 3033-46.
Satoh, H., et al. Increased levels of KL-6 and subsequent mortality in patients with interstitial lung diseases.J Intern Med. Nov. 2006; 260(5): 429-34.
Sausville, E., et al. A role for ferrous ion and oxygen in the degradation of DNA by bleomycin. Biochem Biophys Res Commun. Dec. 6, 1976; 73(3): 814-22.
Schniedermann, J., et al. Mouse lung contains endothelial progenitors with high capacity to form blood and lymphatic vessels BMC Cell Biol. 2010; 11:50.
Schrier D. et al., The Role of Strain Variation in Murine Bleomycin-Induced Pulmonary Fibrosis. Am Rev Respir Dis., 127(1):63-6,1983.
Seibold, M.A., et al. A Common MUC5B Promoter Polymorphism and Pulmonary Fibrosis. N Engl J Med. Apr. 21, 2011; 364(16): 1503-12.
Selman, M. & Pardo, A. Idiopathic pulmonary fibrosis: an epithelial/fibroblastic cross-talk disorder. Respir Res. 2002; 3: 3.
Shan, L., et al. Centrifugal Migration of Mesenchymal Cells in Embryonic Lung. Dev Dyn. 2008; 237: 750-5.
Shao, D.D., et al. Pivotal Advance: Th-1 cytokines inhibit, and Th-2 cytokines promote fibrocyte differentiation. J Leukoc Biol. Jun. 2008; 83(6): 1323-33.
Siegelman, M.H., et al. Activation and interaction of CD44 and hyaluronan in immunological systems. J Leukoc Biol. Aug. 1999; 66(2): 315-21.
Silva, J.M. et al. (2005) Second-generation shRNA libraries covering the mouse and human genomes. Nature Genetics 37(11):1281-1288.
Sizemore, S. et al, Podocalyxin Increases the Aggressive Phenotype of Breast and Prostate Cancer Cells in vitro through Its Interaction with Ezrin. Cancer Res. 67: 6183-91 (2007).
Smith, M. et al. Usual interstitial pneumonia-pattern fibrosis in surgical lung biopsies. Clinical, radiological and histopathological clues to aetiology.J Clin Pathol. Oct. 2013; 66(1): 896-903.

(56) References Cited

OTHER PUBLICATIONS

Snider, G. et al., Chronic Interstitial Pulmonary Fibrosis Produced in Hamsters by Endotracheal Bleomycin—Lung Volumes, Volume-Pressure Relations, Carbon Monoxide Uptake, and Arterial Blood Gas Studies. Am Rev Respir Dis. 117: 289-297.
Song, J. W., et al. Acute Exacerbation of Idiopathic Pulmonary Fibrosis: Incidence, Risk Factors, and Outcome. Eur Respir J. 2011; Feb; 37(2): 356-63.
Starcher B. et al., Increased elastin and collagen content in the lungs of hamsters receiving an intratracheal injection of bleomycin. Am Rev Respir Dis., 117(2):299-305, 1978.
Strunk, R.C., et al. Pulmonary Alveolar Type 11 Epithelial Cells Synthesize and Secrete Proteins of the Classical and Alternative Complement Pathways. J. Clin. Invest. 1988; 81: 1419-1426.
Suganuma, H., et al. Enhanced migration of fibroblasts derived from lungs with fibrotic lesions. Thorax. Sep. 1995; 50(9): 984-9.
Summer, R., et al. Isolation of an Adult Mouse Lung Mesenchymal Progenitor Cell Population. Am J Respir Cell Mol Biol. 2007; 37: 152-9.
Sun, H. et al., Oligonucleotide Aptamers: New Tools for Targeted Cancer Therapy. Molec. Therapy—Nucleic Acids 2014, 3: e182; doi: 10.1038/mbna.2014.32.
Tanjore, H., et al. Contribution of Epithelial-derived Fibroblasts to Bleomycin-induced Lung Fibrosis. Am J Respir Crit Care Med. Oct. 1, 2009; 180(7): 657-65.
Teder, P., et al. Resolution of Lung Inflammation by CD44. Science. Apr. 5, 2002; 296: 155-8.
Tesari, M.A.. Transcriptional Activation of the Cyclin A Gene by the Architectural Transcription Factor HMGA2. Mol. Cell Biol. 23:(24) 9104-9116 (2003).
Thannickal, V.J., et al. Myofibroblast Differentiation by Transforming Growth Factor-beta 1 Is Dependent on Cell Adhesion and Integrin Signaling via Focal Adhesion Kinase. J Biol Cehm. Apr. 4, 2003; 278(14): 12384-12389.
Thomas, A.Q., et al. Heterozygosity for a Surfactant Protein C Gene Mutation Associated with Usual Interstitial Pneumonitis and Cellular Nonspecific Interstitial Pneumonitis in One Kindred. Am J. Respir Crit Care Med. May 1, 2002; 165(9): 1322-8.
Thrall, R. et al., Bleomycin-induced pulmonary fibrosis in the rat: inhibition by indomethacin. Am J Pathol, 95: 117-130, 1979.
Timmermans, F., et al. Endothelial progenitor cells: identity defined?. J Cell Mol Med. 2009; 13: 87-102.
Tomasek, J.J., et al. Myofibroblasts and mechano-regulation of connective tissue remodelling. Nat Rev Mol Cell Biol. May 2002; 3(5): 349-63.
Toole, B. P. Hyaluronan: from extracellular glue to pericellular cue. Nat Rev Cancer. Jul. 2004; 4(7): 528-39.
Torry, D.J., et al. Anchorage-independent Colony Growth of Pulmonary Fibroblasts Derived from Fibrotic Human Lung Tissue. J Clin Invest. Apr. 1994; 93(4): 1525-32.
Tsakiri, K.D., et al. Adult-onset pulmonary fibrosis caused by mutations in telomerase. Proc Natl Acad Sci USA. May 1, 2007; 104(18): 7552-7.
Ulloa, L. et al. Inhibition of transforming growth factor-b/SMAD signalling by the interferon-g/STAT pathway. Nature Feb. 25, 1999; 397(6721): 710-3.
Umezawa, H. et al., Studies on bleomycin Cancer 20: 891-895, 1967.
Umezawa, H., Chemistry and mechanism of action of bleomycin.. Fed Proc, 33: 2296 2302, 1974.
Vaccaro, C.A., et al. Alveolar Wall Basement Membranes in Bleomycin-induced Pulmonary Fibrosis. Am Rev Respir Dis. Oct. 1985; 132(4): 905-12.
Valenta, T., et al. The many faces and functions of b-catenin. EMBO J. Jun. 13, 2012; 31(12): 2714-36.
Vittal, R. et al., Effects of the Protein Kinase Inhibitor, Imatinib Mesylate, on Epithelial/Mesenchymal Phenotypes: Implications for Treatment of Fibrotic Diseases. J Pharmacol Exp Ther., 321(1):35-44, 2007.
Vittal, R. et al., Modulation of Prosurvival Signaling in Fibroblasts by a Protein Kinase Inhibitor Protects against Fibrotic Tissue Injury. Am J Pathol., 166(2):367-75, 2005.
Volckaert, T., et al. Parabronchial smooth muscle constitutes an airway epithelial stem cell niche in the mouse lung after injury. J Clin Invest. 2011; 121: 4409-19.
Waghray, M., et al. Hydrogen peroxide is a diffusible paracrine signal for the induction of epithelial cell death by activated myofibroblasts. FASEB J. May 2005; 19(7): 854-6.
Wang, D., et al. A pure population of lung alveolar epithelial type II cells derived from human embryonic stem cells. Proc Natl Acad Sci USA. Mar. 13, 2007; 104(11): 4449-54.
Wang, Y., et al. Genetic Defects in Surfactant Protein A2 Are Associated with Pulmonary Fibrosis and Lung Cancer. Am J Hum Genet. Jan. 2009; 84(1): 52-9.
Werner, S., et al. Regulation of Wound Healing by Growth Factors and Cytokines. Physiol Rev. Jul. 2003; 83(3): 835-870.
Weterman, M.A.J, et al, nmb, a novel gene, is expressed in low-metastatic human melanoma cell lines and xenografts. Intl. J. Cancer 60: 73-81 (1995).
White, E.S., et al. Negative Regulation of Myofibroblast Differentiation by PTEN (Phosphatase and Tensin Homolog Deleted on Chromosome 10) Sem. Am J Respir Crit Care Med. Jan. 1, 2006; 173(1): 112-21.
Wiegand, S. et al. Global Quantitative Phosphoproteome Analysis of Human Tumor Xenografts Treated with a CD44 Antagonist. Cancer Res. Sep. 2012; 72(17): 4329-39.
Wilson, M.S., et al. Bleomycin and IL-1beta-mediated pulmonary fibrosis is IL-17A dependent. J Exp Med. Mar. 15, 2010; 207(3): 535-52.
Wilson, M.S., et al. Colitis and Intestinal Inflammation in IL10−/− Mice Results From IL-13Ra2-Mediated Attenuation of IL-13 Activity. Gastroenterology. Jan. 2011; 140(1): 254-64.
Wipff, P., et al. Myofibroblast contraction activates latent TGF-beta1 from the extracellular matrix. J Cell Biol. Dec. 17, 2007; 179(6): 1311-23.
www.genecards.org/cgi-bin/carddisp.pl?gene-CD44. printed from internet Sep. 7, 2018.
www.genecards.org/cgi-bin/carddisp.pl?gene=CTNNB1. printed from internet Aug. 20, 2018.
www.genecards.org/cgi-bin/carddisp.pl?gene=WNT1. printed from internet Aug. 20, 2018.
Wynn, T.A., et al. An IL-12-based vaccination method for preventing fibrosis induced by schistosome infection. Nature. Aug. 17, 1995; 376(6541): 594-6.
Wynn, T.A., et al. Macrophages: Master Regulators of Inflammation and Fibrosis. Semin Liver Dis. Aug. 2010; 30(3): 245-57.
Wynn, T.A., et al. Mechanisms of fibrosis: therapeutic translation for fibrotic disease. Nat Med. Jul. 6, 2012; 18(7): 1028-40.
Yamamoto, H., et al. Epithelial-vascular cross talk mediated by VEGF-A and HGF signaling directs primary septae formation during distal lung morphogenesis. Dev Biol. Aug. 1, 2007; 308(1) 44-53.
Yoder, M.C., Progenitor Cells in the Pulmonary Circulation. Proc Am Thorac Soc. 2011; 8: 466-70.
Yokoyama, A., et al. Prognostic value of circulating KL-6 in idiopathic pulmonary fibrosis. Respirology. Mar. 2006; 11(2): 164-8.
Zasloff, M. Antimicrobial peptides of multicellular organisms. Nature. Jan. 24, 2002; 415(6870): 389-95.
Zeisberg, M., et al. Cellular Mechanisms of Tissue Fibrosis. 1. Common and organ-specific mechanisms associated with tissue fibrosis. Am J Physiol Cell Physiol. Feb. 1, 2013; 304(3): C216-25.
Zhang, K., et al. Lung monocyte chemoattractant protein-1 gene expression in bleomycin-induced pulmonary fibrosis. J Immunol. Nov. 15, 1994; 153(10): 4733-41.
Zhang, Y. et al. A Variant in the Promoter of MUC5B and Idiopathic Pulmonary Fibrosis. N Engl J Med. Apr. 21, 2011; 364(16): 1576-7.
Zhang, Y., et al. Enhanced IL-1 beta and tumor necrosis factor-alpha release and messenger RNA expression in macrophages from idiopathic pulmonary fibrosis or after asbestos exposure. J Immunol. May 1, 1993; 150(9): 4188-96.

(56) References Cited

OTHER PUBLICATIONS

Zhang, Y., et al., Biomarkers in idiopathic pulmonary fibrosis. Curr Opin Pulm Med. Sep. 2012; 18(5): 441-6.
Zhang, K., et al. Myofibroblasts and Their Role in Lung Collagen Gene Expression during Pulmonary Fibrosis. Am J Pathol. Jul. 1994; 145(1): 114-25.
Zhao, Y. X., et al. Secretion of complement components of the alternative pathway (C3 and factor B) by the human alveolar type II epithelial cell line A549. Int J Mol Med. 2000; 5: 415-419.
Zhou, Y., et al. Inhibition of mechanosensitive signaling in myofibroblasts ameliorates experimental pulmonary fibrosis. J Clin Invest. Mar. 2013; 123(3): 1096-108.
Zhu, F., et al. IL-17 induces apoptosis of vascular endothelial cells—A potential mechanism for human acute coronary syndrome. Clin Immunol. Nov. 2011; 141(2): 152-60.
Zorzetto, M., et al. Complement Receptor 1 Gene Polymorphisms Are Associated with Idiopathic Pulmonary Fibrosis. Am J Respir Crit Care Med. Aug. 1, 2003; 168(3): 330-4.
Zorzetto, M., et al. Nod2/CARD15 gene polymorphisms in idiopathic pulmonary fibrosis. Sarcoidosis Vasc Diffuse Lung Dis. Oct. 2005; 22(3): 180-5.
Zuo, F., et al. Gene expression analysis reveals matrilysin as a key regulator of pulmonary fibrosis in mice and humans. Proc Natl Acad Sci USA. Apr. 30, 2002; 99(9): 6292-7.
Fan, J et al. Interleukin-1 induces tubular epithelial-myofibroblast transdifferentiation through a transforming growth factor-beta1-dependent mechanism in vitro. Am J Kidney Dis. Apr. 2001; 37(4): 820-31.
Flaherty, K.R., et al. Prognostic Implications of Physiologic and Radiographic Changes in Idiopathic Interstitial PneumoniaAm J Respir Crit Care Med. Sep. 1, 2003; 168(5): 543-8.
Fox, C., Drug Delivery & Development. Reversing Idiopathic Pulmonary Fibrosis. http://www.dddmag.com/news/2014/10/reversing-idiopathic-pulmonary-fibrosis, Oct. 15, 2014; downloaded from internet Aug. 15, 2018.
Franzdottir, S.R., et al. Airway branching morphogenesis in three dimensional culture. Respir Res. 2010; 11: 162.
Friedman, S.L. Fibrogenic cell reversion underlies fibrosis regression in liver. Proc Natl Acad Sci USA. Jun. 12, 2012; 109(24): 9230-9231.
Fukuda, Y., et al. Patterns of Pulmonary Structural Remodeling After Experimental Paraquat Toxicity. Am J Pathol. Mar. 1985; 118(3): 452-75.
Furuhashi, K.,et al., Increased expression of YKL-40, a chitinase-like protein, in serum and lung of patients with idiopathic pulmonary fibrosis. Respir Med. Aug. 2010; 104(8): 1204-10.
Gangadharan, B. et al. Murine gammaherpesvirus-induced fibrosis is associated with the development of alternatively activated macrophages. J Leukoc Biol. Jul. 2008; 84(1): 50-8.
Gangloff, YG et al, The histone fold is a key structural motif of transcription factor TFIID. Trends Biochem. Sci. 26: 250-257(2001).
Gasse, P., et al. IL-1 and IL-23 Mediate Early IL-17A Production in Pulmonary Inflammation Leading to Late Fibrosis. PLoS One. 2011; 6(8): e23185.
Gasse, P., et al. IL-1R1/MyD88 signaling and the inflammasome are essential in pulmonary inflammation and fibrosis in mice. J Clin Invest. Dec. 2007; 117(12): 3786-99.
Giangreco, A., et al. Molecular phenotype of airway side population cells. Am J Physiol Lung Cell Mol Physiol. 2004; 286: L624-30.
Giannone, G., et al. Substrate rigidity and force define form through tyrosine phosphatase and kinase pathways. Trends Cell Biol. Apr. 2006; 16(4): 213-23.
Gilani, S. R., et al. CD28 Down-Regulation on Circulating CD4 T-Cells Is Associated with Poor Prognoses of Patients with Idiopathic Pulmonary Fibrosis. PLoS One. Jan. 29, 2010; 5(1): e8959.
Gilbert, H.S. Myelofibrosis revisited: characterization and classification of myelofibrosis in the setting of myeloproliferative disease. Prog Clin Biol Res. 1984; 154: 3-17 (Abstract).
Goldstein R., et al., Failure of mechanical properties to parallel changes in lung connective tissue composition in bleomycin-induced pulmonary fibrosis in hamsters. Am Rev Respir Dis., 120(1):67-73, 1979.
Greene, K.E., et al. Serum surfactant proteins-A and -D as biomarkers in idiopathic pulmonary fibrosis. Eur Respir J. Mar. 2002; 19(3): 439-46.
Harari, S., et al. IPF: new insight on pathogenesis and treatment. Allergy. May 2010; 65(5):537-53.
Hashimoto, N., et al. Bone marrow-derived progenitor cells in pulmonary fibrosis. J Clin Invest. Jan. 2004; 113(2): 243-52.
Hashimoto, N., et al. Endothelial-Mesenchymal Transition in Bleomycin-Induced Pulmonary Fibrosis. Am J Respir Cell Mol Biol. Aug. 2010; 43(2): 161-72.
He, W., et al. Matrix Metalloproteinase-7 as a Surrogate Marker Predicts Renal Wnt/b-Catenin Activity in CKD. J Am Soc Nephrol. Feb. 2012; 23(2): 294-304.
Hecker L. et al., NADPH Oxidase-4 Mediates Myofibroblast Activation and Fibrogenic Responses to Lung Injury. Nat Med., 15(9):1077-81, 2009.
Hegab, A. E., et al. Isolation and Characterization of Murine Multipotent Lung Stem Cells. Stem Cells Dev. 2010; 19: 523-36.
Heise, R. L., et al. Mechanical Stretch Induces Epithelial-Mesenchymal Transition in Alveolar Epithelia via Hyaluronan Activation of Innate Immunity. J Biol Chem. May 20, 2011; 286(20): 17435-44.
Hinz, B. Formation and Function of the Myofibroblast during Tissue Repair. J Invest Dermatol. Mar. 2007; 127(3): 526-37.
Hinz, B. Tissue stiffness, latent TGF-beta1 activation, and mechanical signal transduction: implications for the pathogenesis and treatment of fibrosis. Curr Rheumatol Rep. Apr. 2009; 11(2): 120-6.
Hinz, B., et al. Alpha-Smooth Muscle Actin Expression Upregulates Fibroblast Contractile Activity. Mol Biol Cell. Sep. 2001; 12(9): 2730-41.
Hinz, B., et al. Biological Perspectives the Myofibroblast One Function, Multiple Origins. Am J Pathol. Jun. 2007; 170(6): 1807-16.
Hinz, B., et al. Myofibroblast Development Is Characterized by Specific Cell-Cell Adherens Junctions. Mol Biol Cell. Sep. 2004; 15(9): 4310-20.
Hinz, B., Masters and servants of the force: The role of matrix adhesions in myofibroblast force perception and transmission. Eur J Cell Biol. Apr. 2006; 85(3-4): 175-181.
Hodgson, U., et al. ELMOD2 Is a Candidate Gene for Familial Idiopathic Pulmonary Fibrosis. Am J Hum Genet. Jul. 2006; 79(1): 149-54.
Hoffman, A.M., et al. Lung-Derived Mesenchymal Stromal Cell Post-Transplantation Survival, Persistence, Paracrine Expression, and Repair of Elastase-Injured Lung. Stem Cells Dev. 2011; 20: 1779-92.
Horowitz, J.C., et al. Activation of the Pro-survival Phosphatidylinositol 3-Kinase/AKT Pathway by Transforming Growth Factor-beta1 in Mesenchymal Cells Is Mediated by p38 MAPK-dependent Induction of an Autocrine Growth Factor*. J Biol Chem. Jan. 9, 2004; 279(2): 1359-67.
Horowitz, J.C., et al. Combinatorial activation of FAK and AKT by transforming growth factor-?1 confers an anoikis-resistant phenotype to myofibroblasts. Cell Signal. Apr. 2007; 19(4): 761-71.
Hu, B., et al. Gut-Enriched Kruppel-Like Factor Interaction with Smad3 Inhibits Myofibroblast Differentiation. Am J Respir Cell Mol Biol. Jan. 2007; 36(1): 78-84.
Huang, X., et al. Matrix Stiffness-Induced Myofibroblast Differentiation Is Mediated by Intrinsic Mechanotransduction. Am J Respir Cell Mol Biol. Sep. 2012; 47(3): 340-8.
Humbles, A.A., et al. A Critical Role for Eosinophils in Allergic Airways Remodeling. Science. Sep. 17, 2004; 305(5691): 1776-9.
Hung, C., et al. Role of Lung Pericytes and Resident Fibroblasts in the Pathogenesis of Pulmonary Fibrosis. Am J Respir Crit Care Med. Oct. 1, 2013; 188(7): 820-30.
Hutyrova, B., et al. Interleukin-1 Gene Cluster Polymorphisms in Sarcoidosis and Idiopathic Pulmonary Fibrosis. Am J Respir Crit Care Med. Jan. 15, 2002; 165(2): 148-51.

(56) References Cited

OTHER PUBLICATIONS

International Preliminary Report on Patentability PCT/US2016/053743; dated Mar. 27, 2018, 5 pages.
International Search Report and Written Opinion; PCT/US2016/053743; dated Jan. 26, 2017; 6 pages.
Ishikawa, N., et al. Utility of KL-6/MUC1 in the clinical management of interstitial lung diseases. Respir Investig. Mar. 2012; 50(1): 3-13.
Izbicki G. et al., Time course of bleomycin-induced lung fibrosis. Int J Exp Pathol., 83(3):111-9, 2002.
Jakubzick, C. et al Impact of Interleukin-13 Responsiveness on the Synthetic and Proliferative Properties of Th1- and Th2-Type Pulmonary Granuloma Fibroblasts. Am J Pathol. May 2003; 162(5): 1475-86.
Janick-Buckner, D. et al., Alteration of bronchoalveolar lavage cell populations following bleomycin treatment in mice. Toxicol Appl Pharmacol., 100(3):465-73, 1989.
Jiang, D., et al. Hyaluronan as an Immune Regulator in Human Diseases. Physiol Rev. Jan. 2011; 91(1): 221-64.
Jiang, D., et al. Regulation of lung injury and repair by Toll-like receptors and hyaluronan. Nat Med. Nov. 2005; 11(11): 1173-9.
Jiang, F., et al. Gene expression profile of quiescent and activated rat hepatic stellate cells implicates Wnt signaling pathway in activation. J Hepatol. Sep. 2006; 45(3): 401-9.
Jones, L. K., et al. IL-1RI deficiency ameliorates early experimental renal interstitial fibrosis. Nephrol Dial Transplant. 2009; 24: 3024-32.
Jordana, M., et al. Heterogeneous Proliferative Characteristics of Human Adult Lung Fibroblast Lines and Clonally Derived Fibroblasts from Control and Fibrotic Tissue. Am Rev Respir Dis. Mar. 1988; 137(3): 579-84.
Kalluri, R & Weinberg, R.A.. The basics of epithelial-mesenchymal transition. J Clin Invest. Jun. 1, 2009; 119(6): 1420-28.
Kamari, Y., et al. Lack of Interleukin-1alpha or Interleukin-1beta Inhibits Transformation of Steatosis to Steatohepatitis and Liver Fibrosis in Hypercholesterolemic Mice. J Hepatol. Nov. 2011; 55(5): 1086-94.
Katzenstein, A-L., et al. Erratum to "Diagnosis of usual interstitial pneumonia and distinction from other fibrosing interstitial lung diseases". Hum Pathol. Sep. 2008; 39(9): 1275-94.
Katzenstein, A., et al. Idiopathic Pulmonary Fibrosis Clinical Relevance of Pathologic Classification. Am J Respir Crit Care Med. Apr. 2008; 157: 1301-15.
Kaviratne, M., et al. IL-13 activates a mechanism of tissue fibrosis that is completely TGF-beta independent. J Immunol. Sep. 15, 2004; 173(6): 4020-9.
Keane, M.P. et al. The importance of balanced pro-inflammatory and antiinflammatory mechanisms in diffuse lung disease. Am J Physiol Lung Cell Mol Physiol. Jul. 2001; 281(1): L92-7.
Kim, K.K., et al. Alveolar epithelial cell mesenchymal transition develops in vivo during pulmonary fibrosis and is regulated by the extracellular matrix. Proc Natl Acad Sci USA. Aug. 29, 2006; 103(35): 13180-5.
Kim, V.N. MicroRNA biogenesis: coordinated cropping and dicing. Nature Reviews, Molecular Cell Biology 6(5):376-385 (2005).
Kinder, B.W., et al. Baseline BAL Neutrophilia Predicts Early Mortality in Idiopathic Pulmonary Fibrosis. Chest. Jan. 2008; 133(1): 226-32.
Kinder, B.W., et al. Serum Surfactant Protein-A Is a Strong Predictor of Early Mortality in Idiopathic Pulmonary Fibrosis. Chest. Jun. 2009; 135(6): 1557-63.
King, J., et al.Structural and functional characteristics of lung macro- and microvascular endothelial cell phenotypes. Microvasc Res. 2004; 67: 139-51.
King, T.E. et al. Effect of interferon gamma-1b on survival in patients with idiopathic pulmonary fibrosis (INSPIRE): a multicentre, randomised, placebo-controlled trial. Lancet. 2009; 374(9685): 222-8.

Kisseleva, T., et al. Myofibroblasts revert to an inactive phenotype during regression of liver fibrosis. Proc Natl Acad Sci USA. Jun. 12, 2012; 109(24): 9448-53.
Kitani, A., et al. Transforming growth factor (TGF)-beta1-producing regulatory T cells induce Smad-mediated interleukin 10 secretion that facilitates coordinated immunoregulatory activity and amelioration of TGF-beta1-mediated fibrosis. J Exp Med. Oct. 20, 2003; 198(8): 1179-88.
Kolb, M. et al. Transient expression of IL-1? induces acute lung injury and chronic repair leading to pulmonary fibrosis. J Clin Invest. Jun. 2001; 107(12): 1529-36.
Kolodsick, J.E. et al. Protection from Fluorescein Isothiocyanate-Induced Fibrosis in IL-13-Deficient, but Not IL-4-Deficient, Mice Results from Impaired Collagen Synthesis by Fibroblasts1. J Immunol. Apr. 1, 2004; 172(7): 4068-76.
Komiya, Y, et al. Wnt signal transduction pathways. Organogenesis. Apr.-Jun. 2008; 4(2): 68-75.
Konigshoff, M., et al. WNT1-inducible signaling protein-1 mediates pulmonary fibrosis in mice and is upregulated in humans with idiopathic pulmonary fibrosis. J Clin Invest. Apr. 2009; 119(4): 772-87.
Konishi, K., et al. Gene Expression Profiles of Acute Exacerbations of Idiopathic Pulmonary Fibrosis. Am J Respir Crit Care med. Jul. 15, 2009; 180(2): 167-75.
Korthagen, N.M. et al. Serum and BALF YKL-40 levels are predictors of survival in idiopathic pulmonary fibrosis. Respir Med. Jan. 2011; 105(1): 106-13.
Kramann, R., et al. Perivascular Gli1 + Progenitors Are Key Contributors to Injury-Induced Organ Fibrosis. Cell Stem Cell. Jan. 8, 2015; 16(1): 51-66.
Krenning, G., et al. The origin of fibroblasts and mechanism of cardiac fibrosis. J Cell Physiol. Nov. 2010; 225(3):631-7.
Krizhanovsky, V., et al. Senescence of Activated Stellate Cells Limits Liver Fibrosis. Cell. Aug. 22, 2008; 134(4): 657-67.
Kuan, CT et al, Glycoprotein Nonmetastatic Melanoma Protein B, a Potential Molecular Therapeutic Target in Patients with Glioblastoma Multiforme. Clin. Cancer Res. 12:(7) 1970-82 (2006).
Kuperman, D.A., et al. Direct effects of interleukin-13 on epithelial cells cause airway hyperreactivity and mucus overproduction in asthma. Nat Med. Aug. 2002; 8(8): 885-9.
Laan, M., et al. Neutrophil Recruitment by Human IL-17 Via C-X-C Chemokine Release in the Airways. J Immunol. Feb. 15, 1999; 162(4): 2347-52.
Larrucea, S. et al., Expression of podocalyxin enhances the adherence, migration, and intercellular communication of cells. Exptl Cell Res. 314: 2004-15 (2008).
Larsson, O., et al. Fibrotic Myofibroblasts Manifest Genome-Wide Derangements of Translational Control. PLoS One. Sep. 16, 2008; 3(9): e3220.
Latsi, P.I., et al. Fibrotic Idiopathic Interstitial Pneumonia the Prognostic Value of Longitudinal Functional Trends. Am J Respir Crit Care Med. Sep. 1, 2003; 168(5): 531-537.
Latsi,. P., et al. Analysis of IL-12 p40 subunit gene and IFN-? G5644A polymorphisms in Idiopathic Pulmonary Fibrosis. Respir Res. 2003. 4:6.
Lawson W. et al., Increased and prolonged pulmonary fibrosis in surfactant protein C-deficient mice following intratracheal bleomycin. Am J Pathol. 2005;167(5):1267-1277.
Lawson, W.E., et al. Genetic mutations in surfactant protein C are a rare cause of sporadic cases of IPF. Thorax. Nov. 2004; 59(11): 977-80.
Lebleu, V.S., et al. Origin and Function of Myofibroblasts in Kidney Fibrosis. Nat Med. Aug. 2013; 19(8): 1047-53.
Lebleu, V.S., et al. Origin and Function of Myofibroblasts in Kidney Fibrosis. Nat Med. Feb. 2013; 19(2): 227-31.
Lee, C.G., et al. Interleukin-13 induces tissue fibrosis by selectively stimulating and activating transforming growth factor beta(1). J Exp Med. Sep. 17, 2001; 194(6): 809-821.
Lee, J.H., et al. Interleukin-13 Induces Dramatically Different Transcriptional Programs in Three Human Airway Cell Types. Am J Respir Cell Mol Biol. Oct. 2001; 25(4): 474-85.
Lesley, J., et al. CD44 and Its Interaction with Extracellular Matrix. Adv Immunol. 1993; 54: 271-335.

(56) References Cited

OTHER PUBLICATIONS

Levick, S. P., et al. Cardiac Mast Cells Mediate Left Ventricular Fibrosis in the Hypertensive Rat Heart. Hypertension. Jun. 2009; 53(6): 1041-1047.

Li, Y., et al. Severe lung fibrosis requires an invasive fibroblast phenotype regulated by hyaluronan and CD44. J Exp Med. Jul. 4, 2011; 208(7): 1459-1471.

Li, Z., et al. Protein Kinase C d and c-Abl Kinase Are Required for Transforming Growth Factor beta Induction of Endothelial-Mesenchymal Transition In Vitro. Arthritis Rheum. Aug. 2011; 63(8): 2473-83.

Liang, J., et al. MK2 Inhibition Attenuates Fibroblast Invasion and Severe Lung Fibrosis. Am J Respir Crit Care Med, May 10, 2015. vol. 191, A5333. Abstract only.

Liu, G., et al. miR-21 mediates fibrogenic activation of pulmonary fibroblasts and lung fibrosis. J Exp Med. Aug. 2, 2010; 207(8): 1589-97.

Liu, L. et al. Association of ENA-78, IP-10 and VEGF gene polymorphism with idiopathic pulmonary fibrosis. Zhonghua yi xue za zhi. Oct. 20, 2009; 89(38): 2690-4 (Abstract).

Liu, Y., et al. IL-13 Induces Connective Tissue Growth Factor in Rat Hepatic Stellate Cells via TGF-beta-Independent Smad Signaling. J Immunol. Sep. 1, 2011; 187(5): 2814-2823.

Lok, S.S. et al. Murine gammaherpes virus as a cofactor in the development of pulmonary fibrosis in bleomycin resistant mice. Eur Respir J. Nov. 2002; 20(5): 1228-32.

Lovgren, A.K., et al. ?-arrestin Deficiency Protects Against Pulmonary Fibrosis in Mice and Prevents Fibroblast Invasion of Extracellular Matrix. SC. Sci Transl Med. Mar. 16, 2011; 3(74):74ra23. doi:10.1126/scitranslmed.3001564.

Lown, J.W., et al. The mechanism of the bleomycin-induced cleavage of DNA1. Biochem Biophys Res Commun. Aug. 22, 1977; 77(4): 1150-7.

Ma, G., et al. Indian hedgehog mutations causing brachydactyly type A1 impair Hedgehog signal transduction at multiple levels. Cell Res. 21: 1343-57 (2011).

Mailleuix, A. A., et al. Fgf10 expression identifies parabronchial smooth muscle cell progenitors and is required for their entry into the smooth muscle cell lineage. Development. May 2005; 132(9): 2157-66.

Martinelli, M., et al. A role for epidermal growth factor receptor in idiopathic pulmonary fibrosis onset. Mol Biol Rep. Oct. 2011; 38(7): 4613-7.

Abe, R., et al. Peripheral Blood Fibrocytes: Differentiation Pathway and Migration to Wound Sites. J Immunol. Jun. 15, 2001; 166(12): 7556-62.

Acharya, P.S., et al., Fibroblast migration is mediated by CD44-dependent TGF beta activation. J Cell Sci. May 1, 2008; 121(Pt 9): 1393-402.

Ahn, M-H., et al. A promoter SNP rs4073T>A in the common allele of the interleukin 8 gene is associated with the development of idiopathic pulmonary fibrosis via the IL-8 protein enhancing mode. Respir Res. Jun. 8, 2011; 12:73.

Alvarez, D. F., et al. Lung microvascular endothelium is enriched with progenitor cells that exhibit vasculogenic capacity. Am J Physiol Lung Cell Mol Physiol. 2008; 294: L419-30.

Andersson-Sjoland, A., et al. Fibrocytes are a potential source of lung fibroblasts in idiopathic pulmonary fibrosis. Int J Biochem Cell Biol. 2008; 40(10) 2129-40.

Arch, R., et al. Participation in normal immune responses of a metastasis-inducing splice variant of CD44. Science. Jul. 31, 1992; 257(5070): 682-5.

Armanios, M.Y., et al. Telomerase Mutations in Families with Idiopathic Pulmonary Fibrosis. N Engl J Med. Mar. 29, 2007; 356(13): 1317-26.

Baarsma, H.A., et al. Activation of WNT/b-Catenin Signaling in Pulmonary Fibroblasts by TGF-b1 Is Increased in Chronic Obstructive Pulmonary Disease. PLoS One. 2011; 6(9): e25450.

Balasubramaniam, V., et al. Bone marrow-derived angiogenic cells restore lung alveolar and vascular structure after neonatal hyperoxia in infant mice. Am J Physiol Lung Cell Mol Physiol. 2010; 298: L315-L323.

Balestrini, J.L., et al. The mechanical memory of lung myofibroblastswz. Integr Biol (Camb). Apr. 2012; 4(4): 410-21.

Barkauskas, C. E., et al. Cellular Mechanisms of Tissue Fibrosis. 7. New insights into the cellular mechanisms of pulmonary fibrosis. Am J Physiol Cell Physiol. Jun. 1, 2014; 306(11): C987-96.

Bartel, DP, MicroRNAs: genomics, biogenesis, mechanism, and function. Cell 116(2):281-297 (2004).

Bellusci, S., et al. Fibroblast Growth Factor 10 (FGF10) and branching morphogenesis in the embryonic mouse lung. Development. Dec. 1997; 124(23): 4867-78.

Bergers, G., et al. The role of pericytes in blood-vessel formation and maintenance. Neuro Oncol. Oct. 2005; 7(4): 452-64.

Birck, C. et al., Human TAFII28 and TAFII18 Interact through a Histone Fold Encoded by Atypical Evolutionary Conserved Motifs Also Found in the SPT3 Family. Cell 94: 239-49 (1998).

Bjermer, L., et al. Hyaluronan and type III procollagen peptide concentrations in bronchoalveolar lavage fluid in diopathic pulmonary fibrosis. Thorax. Feb. 1989; 44(2): 126-31.

Bournazos, S., et al. Fcy Receptor IIIb (CD16b) Polymorphisms are Associated with Susceptibility to Idiopathic Pulmonary Fibrosis. Lung. Dec. 2010; 188(6): 475-81.

Brummelkamp, T.R. et al. (2002) A system for stable expression of short interfering RNAs in mammalian cells. Science 296:550-553.

Bujak, M., et al. The role of Interleukin-1 in the pathogenesis of heart disease. Arch Immulon Ther Exp (Warsz). May-Jun. 2009; 57(3): 165-76.

Camenisch, T.D., et al. Disruption of hyaluronan synthase-2 abrogates normal cardiac morphogenesis and hyaluronan-mediated transformation of epithelium to mesenchyme. J Clin Invest. Aug. 2000; 106(3): 349-60.

Chambers, R.C. Abnormal wound healing responses in pulmonary fibrosis: focus on coagulation signalling. Eur Respir Rev. 2008; 17(109): 130-137.

Chamoto, K., et al. CD34+ Progenitor to Endothelial Cell Transition in Post Pneumonectomy Angiogenesis. Am J Respir Cell Mol Biol. Mar. 2012; 46(3): 283-9.

Chan, JH, et al. Antisense oligonucleotides: from design to therapeutic application. Clin. Exp. Pharmacol. Physiol. 33(5-6): 533-40 (2006).

Chang, J.T. et al. Gather: a systems approach to interpreting genomic signatures. Bioinformatics. 2006; 22(23): 2926-33.

Checa, M., et al. MMP-1 polymorphisms and the risk of idiopathic pulmonary fibrosis. Hum Genet. Dec. 2008; 124(5): 465-72.

Chen, J-H., et al. Beta-Catenin Mediates Mechanically Regulated, Transforming Growth Factor-beta1-Induced Myofibroblast Differentiation of Aortic Valve Interstitial Cells. Arterioscler Thromb Vasc Biol. Mar. 2011; 31(3): 590-7.

Cherng, S., et al. Alpha-Smooth Muscle Actin (?-SMA) . J Am Sci. 2008: 4(4): 7-9.

Chiaramonte, M.G., An IL-13 inhibitor blocks the development of hepatic fibrosis during a T-helper type 2-dominated inflammatory response et al. J Clin Invest. Sep. 1999; 104(6): 777-85.

Chiaramonte, M.G., et al. Regulation and function of the interleukin 13 receptor a2 during a T helper cell type 2-dominant immune response J Exp Med. Mar. 17, 2003; 197(6): 687-701.

Chilosi, M., et al. Aberrant Wnt/beta-Catenin Pathway Activation in Idiopathic Pulmonary Fibrosis. Am J Pathol. May 2003; 162(5): 1495-502.

Cho, C. Y., et al., Dressing The Part. Dermatol Clin. Jan. 1998; 16(1): 25-47.

Chung, M.P. et al. Role of Repeated Lung Injury and Genetic Background in Bleomycin-Induced Fibrosis. Am J Respir Cell Mol Biol. Sep. 2003; 29(3 Pt 1): 375-80.

Chunn, J. L. et al. Partially adenosine deaminase-deficient mice develop pulmonary fibrosis in association with adenosine elevations. Am J Physiol Lung Cell Mol Physiol. Mar. 2006; 290(3): L579-87.

Clark, H., et al. The genetics of neonatal respiratory disease.Semin Fetal Neonatal Med. Jun. 2005; 10(3): 271-82.

(56) References Cited

OTHER PUBLICATIONS

Collard, H,.R., et al. Changes in Clinical and Physiologic Variables Predict Survival in Idiopathic Pulmonary Fibrosis. Am J Respir Crit Care Med. Sep. 1, 2003; 168(5): 538-42.

Collard, H.R., et al. Acute Exacerbations of Idiopathic Pulmonary Fibrosis. Am J Respir Crit Care Med. Oct. 1, 2007; 176(7): 636-43.

Collard, H.R., et al. Plasma biomarker profiles in acute exacerbation of idiopathic pulmonary fibrosis. Am J Physiol Lung Cell Mol Physiol. Jul. 2010; 299(1): L3-7.

Cortez, D.M., et al. IL-17 stimulates MMP-1 expression in primary human cardiac fibroblasts via p38 MAPK- and ERK1/2-dependent C/EBP-beta, NF-kappaB, and AP-1 activation. Am J Physiol Heart Circ Physiol. Dec. 2007; 293(6): H3356-65.

Crivellato, E. The role of angiogenic growth factors in organogenesis. Int J Dev Biol. 2011; 55(4-5): 365-75.

Cronkhite, J.T., et al. Telomere Shortening in Familial and Sporadic Pulmonary Fibrosis. Am J Respir Crit Care Med. Oct. 1, 2008; 178(7): 729-37.

Darby, I., et al. a-Smooth muscle actin is transiently expressed by myofibroblasts during experimental wound healing. Lab Invest. Jul. 1990; 63(1): 21-29.

Darby, I.A., et al. Fibroblasts and myofibroblasts in wound healing. Clin Cosmet Investig Dermatol. 2014; 7: 301-11.

De Langhe, S. P., et al. Levels of mesenchymal FGFR2 signaling modulate smooth muscle progenitor cell commitment in the lung. Dev Biol. Nov. 1, 2006; 299(1): 52-62.

De Wever, O., et al. Role of tissue stroma in cancer cell invasion. J Pathol. Jul. 2003; 200(4): 429-447.

Degrendele, H.C., et al. Requirement for CD44 in Activated T Cell Extravasation into an Inflammatory Site. Science. Oct. 24, 1997; 278(5338): 672-5.

Degryse, A.L., et al. Repetitive intratracheal bleomycin models several features of idiopathic pulmonary fibrosis. Am J Physiol Lung Cell Mol Physiol. Oct. 2010; 299(4): L442-52.

Desmouliere, A., et al. Apoptosis Mediates the Decrease in Cellularity during the Transition between Granulation Tissue and Scar. Am J Pathol. Jan. 1995; 146(1): 56-66.

Ding, B., et al. Endothelial-Derived Angiocrine Signals Induce and Sustain Regenerative Lung Alveolarization. Cell. Oct. 28, 2011; 147(3): 539-53.

Dulauroy, S. et al. Lineage tracing and genetic ablation of ADAM12+ perivascular cells identify a major source of profibrotic cells during acute tissue injury. Nat Med. Aug. 2012; 18(8): 1262-70.

Duong, H., et al. Pro-angiogenic Hematopoietic Progenitor Cells and Endothelial Colony Forming Cells in Pathological Angiogenesis of Bronchial and Pulmonary Circulation. Angiogenesis. 2011; 14(4): 411-22.

TARGETING FIBROBLAST INVASION FOR PULMONARY FIBROSIS

CROSS-REFERENCE TO RELATED APPLICATION

This application claims the benefit of priority to U.S. Provisional Application No. 62/232,864, filed on Sep. 25, 2015, the entire contents of which are incorporated by reference herein.

STATEMENT OF GOVERNMENT FUNDING

This invention was made with government support under P01 HL108793, R01 HL060539, and R01 HL122068, awarded by the National Institutes of Health. The government has certain rights in the invention.

FIELD OF THE INVENTION

The described invention generally relates to the pathogenesis of pulmonary fibrosis and therapeutics for treating same.

BACKGROUND OF THE INVENTION

Anatomy and Physiology of the Lungs

The lungs comprise a pair of organs occupying the pulmonary cavities of the thorax, and are the organs of respiration in which aeration of the blood takes place. Normal human lungs weigh about 1 kg, of which 40% to 50% is blood. The lungs contain about 2.5 L of air at end expiration and 6 L of air at full inflation. In human lungs, the right lung is slightly larger than the left, because ⅔ of the heart is located on the left side of the body. The right lung is divided into three lobes (superior lobe, middle lobe, and inferior, or basal lobe), while the left lung is divided into two lobes (superior lobe and inferior, or basal lobe), and contains the cardiac notch, an indentation in the lung that surrounds the apex of the heart.

Each lung is surrounded by the pleura, which are double-layered serous membranes. The parietal pleura forms the outer layer of the membrane and is attached to the wall of the thoracic cavity; the visceral pleura forms the inner layer of the membrane covering the outer surface of the lungs. Between the parietal and visceral pleura is the pleural cavity, which creates a hollow space into which the lungs expand during inhalation. Serous fluid secreted by the pleural membranes lubricates the inside of the pleural cavity to prevent irritation of the lungs during breathing.

The lungs occupy the majority of the space within the thoracic cavity; they extend laterally from the heart to the ribs on both sides of the chest and continue posteriorly toward the spine. Each lung is roughly cone-shaped with the superior end of the lung forming the point of the cone and the inferior end forming the base. The superior end of the lungs narrows to a rounded tip known as the apex. The inferior end of the lungs, known as the base, rests on the dome-shaped diaphragm. The base of the lungs is concave, following the contours of the diaphragm.

Air enters the body through the nose or mouth and passes through the pharynx, larynx, and trachea. Prior to reaching the lungs, the trachea splits into the left and right bronchi, which are large, hollow tubes made of hyaline cartilage and lined with ciliated pseudostratified epithelium. The hyaline cartilage of the bronchi adds rigidity and prevents the bronchi from collapsing and blocking airflow to the lungs. The pseudostratified epithelium lines the inside of the hyaline cartilage. Each lung receives air from a single, large primary bronchus.

As the primary bronchi enter the lungs, they branch off into smaller secondary bronchi that carry air to each lobe of the lung. The secondary bronchi further branch into many smaller tertiary bronchi within each lobe. The secondary and tertiary bronchi improve the efficiency of the lungs by distributing air evenly within each lobe.

The pseudostratified epithelium that lines the bronchi contains many cilia and goblet cells. The goblet cells secrete mucus. The cilia move together to push mucus secreted by the goblet cells away from the lungs.

Particles of dust and even pathogens like viruses, bacteria, and fungi in the air entering the lungs stick to the mucus and are carried out of the respiratory tract, helping to keep the lungs clean and free of disease.

Many small bronchioles branch off from the tertiary bronchi. Bronchioles differ from bronchi both in size and in the composition of their walls. While bronchi have hyaline cartilage rings in their walls, bronchioles are comprised of elastin fibers and smooth muscle tissue. The tissue of the bronchiole walls allows the diameter of bronchioles to change to a significant degree. When the body requires greater volumes of air entering the lungs, such as during periods of physical activity, the bronchioles dilate to permit increased airflow. In response to dust or other environmental pollutants, the bronchioles can constrict to prevent pollution of the lungs.

The bronchioles further branch off into many tiny terminal bronchioles. Terminal bronchioles are the smallest air tubes in the lungs and terminate at the alveoli of the lungs. Like bronchioles, the terminal bronchioles are elastic, capable of dilating or contracting to control airflow into the alveoli.

The alveoli, the functional units of the lungs, permit gas exchange between the air in the lungs and the blood in the capillaries of the lungs. Alveoli are found in small clusters called alveolar sacs at the end of the terminal bronchiole. Each alveolus is a hollow, cup-shaped cavity surrounded by many fine capillaries. The alveolar epithelium covers >99% of the internal surface area of the lungs (Wang et al. Proc Natl Acad Sci USA. 2007 Mar. 13; 104(11): 4449-54).

Adult lungs are very complicated organs containing at least 40-60 different cell types including fibroblasts (McQualter & Bertoncello. Stem Cells. 2012 May; 30(5): 811-6).

The walls of each alveolus are lined with simple squamous epithelial cells known as alveolar cells, ciliated cells, secretory cells, mainly nonciliated bronchiolar secretory cells which express Secretoglobin 1A member 1 (Scgb1a1+ club cells) (Kidiyoor et al., Gene and Cell Therapy: Therapeutic Mechanisms and Strategies 761 (Nancy Smyth Templeton ed., 4$^{th}$ ed. 2015)), and mesenchymal cell types including resident fibroblasts, myofibroblasts, and perivascular cells that wrap around capillaries (pericytes) (Barkauskas & Noble. Am J Physiol Cell Physiol. 2014 Jun. 1; 306(11): C987-96). The term "club cells" as used herein refers to dome-shaped cells with short microvilli, found in the bronchioles of the lungs that are the epithelial progenitor cells of the small airways. Club cells were formerly known as "Clara cells." A thin layer of connective tissue underlies and supports the alveolar cells. Present within this connective tissue are fibroblasts, the least specialized cells in the connective tissue family, which are found dispersed in connective tissue throughout the body, and play a key role in the wound healing process (Alberts et al. Molecular Biology of the Cell. 4$^{th}$ Ed. New York: Garland Science; 2002. Fibroblasts and Their Transformations: The Connective-Tissue Cell Family, 1300-1301). Surrounding the connective tissue on the outer border of the alveolus are capillaries. A respiratory membrane is formed where the walls of a capillary touch the walls of an alveolus. At the respiratory membrane, gas exchange occurs freely between the air and blood through the extremely thin walls of the alveolus and capillary.

There are two major types of alveolar cells, type 1 alveolar epithelial cells (AEC1s), and type 2 alveolar epithelial cells (AEC2s). AEC1s are large flat cells through which the exchange of $CO_2/O_2$ takes place; they cover approximately 95% of the alveolar surface, comprise approximately 40% of the alveolar epithelium, and 8% of the peripheral lung cells; in contrast, AEC2s are small, cuboidal cells that cover approximately 5% of the alveolar surface, comprise 60% of the alveolar epithelium, and 15% of the peripheral lung cells, and are characterized by their ability to synthesize and secrete surfactant protein C (SPC) and by the distinct morphological appearance of inclusion bodies known as lamellar bodies (Wang et al. Proc Natl Acad Sci USA. 2007 Mar. 13; 104(11): 4449-54; Barkauskas & Noble. Am J Physiol Cell Physiol. 2014 Jun. 1; 306(11): C987-96): AEC2s function: 1) to synthesize, store, and secrete surfactant, which reduces surface tension, preventing collapse of the alveolus; 2) to transport ions from the alveolar fluid into the interstitium, thereby minimizing alveolar fluid and maximizing gas exchange; 3) to serve as progenitor cells for AEC1s, particularly during reepithelialization of the alveolus after lung injury; and 4) to provide pulmonary host defense by synthesizing and secreting several complement proteins including C3 and C5 (Strunk et al. J Clin Invest. 1988; 81: 1419-1426; Rothman et al. J Immunol. 1990; 145: 592-598; Zhao et al. Int J Mol Med. 2000; 5: 415-419) as well as numerous cytokines and interleukins that modulate lymphocyte, macrophage, and neutrophil functions (Mason. Respirology. 2006 January; 11 Suppl: S12-5; Wang et al. Proc Natl Acad Sci USA. 2007 Mar. 13; 104(11): 4449-54).

Septal cells and macrophages are also found inside the alveoli. Septal cells produce alveolar fluid that coats the inner surface of the alveoli. Alveolar fluid is a surfactant that moistens the alveoli, helps maintain the elasticity of the lungs, and prevents the thin alveolar walls from collapsing. Macrophages in the alveoli keep the lungs clean and free of infection by capturing and phagocytizing pathogens and other foreign matter that enter the alveoli along with inhaled air.

The lungs receive air from the external environment through the process of negative pressure breathing, which requires a pressure differential between the air inside the alveoli and atmospheric air. Muscles surrounding the lungs, such as the diaphragm, intercostal muscles, and abdominal muscles, expand and contract to change the volume of the thoracic cavity. Muscles expand the thoracic cavity and decrease the pressure inside the alveoli to draw atmospheric air into the lungs, in a process known as inhalation or inspiration. Muscles contract the size of the thoracic cavity to increase the pressure inside of the alveoli and force air out of the lungs, in a process known as exhalation or expiration.

External respiration is the process of exchanging oxygen and carbon dioxide between the air inside the alveoli and the blood in the capillaries of the lungs. Air inside the alveoli contains a higher partial pressure of oxygen compared to that in the blood in the capillaries. Conversely, blood in the lungs' capillaries contains a higher partial pressure of carbon dioxide compared to that in the air in the alveoli. These partial pressures cause oxygen to diffuse out of the air and into the blood through the respiratory membrane. At the same time, carbon dioxide diffuses out of the blood and into the air through the respiratory membrane. The exchange of oxygen into the blood and carbon dioxide into the air allows the blood leaving the lungs to provide oxygen to the body's cells, while depositing carbon dioxide waste into the air.

The lungs are a frequent target of infection, including those caused by viruses, bacteria, or fungal organisms, and are subject to myriad diseases and conditions. Lung diseases affecting the airways include, without limitation, asthma (an inflammatory disease of the lungs characterized by reversible (in most cases) airway obstruction), bronchitis (inflammation of the mucous membrane of the bronchial tubes), chronic obstructive pulmonary disease (general term used for those diseases with permanent or temporary narrowing of small bronchi, in which forced expiratory flow is slowed, especially when no etiologic or other more specific term can be applied), cystic fibrosis (a congenital metabolic disorder in which secretions of exocrine glands are abnormal, excessively viscid mucus causes obstruction of passageways, and the sodium and chloride content of sweat are increased throughout the patient's life), and emphysema (a lung condition characterized by increase beyond the normal in the size of air spaces distal to the terminal bronchiole (those parts containing alveoli), with destructive changes in their walls and reduction in their number).

Lung diseases affecting the alveoli include, without limitation, acute respiratory distress syndrome (acute lung injury from a variety of causes, characterized by interstitial and/or alveolar edema and hemorrhage as well as perivascular pulmonary edema associated with hyaline membrane formation, proliferation of collagen fibers, and swollen epithelium with increased pinocytosis), emphysema, lung cancer (any of various types of malignant neoplasms affecting the lungs), pneumonia (inflammation of the lung parenchyma characterized by consolidation of the affected part, the alveolar air spaces being filled with exudate, inflammatory cells, and fibrin), pulmonary edema (an accumulation of an excessive amount of watery fluid in cells or intercellular tissues affecting the lungs, usually resulting from mitral stenosis or left ventricular failure), pneumoconiosis (inflammation commonly leading to fibrosis of the lungs caused by the inhalation of dust incident to various occupations), and tuberculosis (a specific disease caused by infection by *Mycobacterium tuberculosis*, the tubercle *bacillus*, which can affect almost any tissue or organ of the body, the most common seat of the disease being the lungs).

Lung diseases affecting the interstitium, the thin lining between the alveoli, include, without limitation, pneumonia, pulmonary edema, and interstitial lung disease, a broad collection of lung conditions including, without limitation, autoimmune diseases (disorders in which the loss of function or destruction of normal tissue arises from humoral or cellular immune responses to the body's own tissue constituents), idiopathic pulmonary fibrosis (an acute to chronic inflammatory process or interstitial fibrosis of the lung of unknown etiology), and sarcoidosis (a systemic granulomatous disease of unknown cause, especially involving the lungs with resulting interstitial fibrosis, but also involving lymph nodes, skin, liver, spleen, eyes, phalangeal bones, and parotid glands).

Lung diseases affecting blood vessels of the lung include, without limitation, pulmonary embolism (obstruction or occlusion of pulmonary arteries by an embolus, most frequently by detached fragments of thrombus from a leg or pelvic vein) and pulmonary hypertension (high blood pressure in the pulmonary circuit).

Lung diseases affecting the pleura include, without limitation, pleural effusion (increased fluid within the pericardial sac), pneumothorax (the presence of free air or gas in the pleural cavity), and mesothelioma (a rare neoplasm derived from the lining of the cells of the pleura and peritoneum which grows as a thick sheet covering the viscera, and is composed of spindle cells or fibrous tissue which may enclose glandlike spaces lined by cuboidal cells).

Lung diseases affecting the chest wall include, without limitation, obesity hypoventilation syndrome (a combination of severe, grotesque obesity, somnolence, and general debility, theoretically resulting from hypoventilation induced by the obesity) and neuromuscular disorders, including, without limitation, amyotrophic lateral sclerosis (a fatal degenerative disease involving the corticobulbar, corticospinal, and spinal motor neurons, manifested by progressive weakness and wasting of muscles innervated by the affected neurons) and myasthenia gravis (a disorder of neuromuscular transmission marked by fluctuating weakness and fatigue of certain voluntary muscles, including those innervated by brainstem motor nuclei).

Regenerative Cells of the Lungs

The adult lung comprises at least 40-60 different cell types of endodermal, mesodermal, and ectodermal origin, which are precisely organized in an elaborate 3D structure with regional diversity along the proximal-distal axis. In addition to the variety of epithelial cells, these include cartilaginous cells of the upper airways, airway smooth muscle cells, interstitial fibroblasts, myofibroblasts, lipofibroblasts, and pericytes as well as vascular, microvascular, and lymphatic endothelial cells, and innervating neural cells. The regenerative ability of lung epithelial stem/progenitor cells in the different regions of the lung are thought to be determined not only by their intrinsic developmental potential but also by the complex interplay of permissive or restrictive cues provided by these intimately associated cell lineages as well as the circulating cells, soluble and insoluble factors and cytokines within their niche microenvironment (McQualter & Bertoncello. Stem Cells. 2012 May; 30(5); 811-16).

The crosstalk between the different cell lineages is reciprocal, multidirectional, and interdependent. Autocrine and paracrine factors elaborated by mesenchymal and endothelial cells are required for lung epithelial cell proliferation and differentiation (Yamamoto et al. Dev Biol. 2007 Aug. 1; 308(1) 44-53; Ding et al. Cell. 2011 Oct. 28; 147(3): 539-53), while endothelial and epithelial cell-derived factors also regulate mesenchymal cell proliferation and differentiation, extracellular matrix deposition and remodeling, and adhesion-mediated signaling (Crivellato. Int J Dev Biol. 2011; 55(4-5): 365-75); Grinnell & Harrington. Pulmonary endothelial cell interactions with the extracellular matrix. In: Voelkel N F, Rounds S, eds. The Pulmonary Endothelium: Function in Health and Disease. Chichester, West Suxssex: Wiley-Blackwell, 2009: 51-72). Chemotactic factors elaborated by these cell lineages also orchestrate the recruitment of inflammatory cells, which participate in the remodeling of the niche and the regulation of the proliferation and differentiation of its cellular constituents (McQualter & Bertoncello. Stem Cells. 2012 May; 30(5); 811-16).

Lung Mesenchymal Stem/Progenitor Cells

Tracheal and distal embryonic lung mesenchyme have been demonstrated to have inductive properties for the regional specification of the embryonic epithelium (Shannon & Deterding. Epithelial-mesenchymal interactions in lung development. In: McDonald J A, ed. Lung Biology in Health and Disease. Vol. 100. New York: Marcel Dekker Inc, 1997, pp. 81-118.). During lung development, mesenchymal stromal cells at the distal tip of the branching epithelium are known to secrete fibroblast growth factor (FGF)-10, which influences the fate and specificity of early lung epithelial progenitor cells (Bellusci et al. Development. 1997 December; 124(23): 4867-78; Ramasamy et al. Dev Biol. 2007 Jul. 15; 307(2): 237-47). FGF-10 is a component of a multifaceted epithelial-mesenchymal cell signaling network involving BMP, Wnt, and Shh pathways which coordinate the proliferation and differentiation of progenitor cells in the developing lung (reviewed in Morrisey & Hogan. Dev Cell. 2010 Jan. 19; 18(1): 8-23). Lineage tracing studies have also revealed that FGF-10$^{pos}$ mesenchymal cells residing at the branching tip of the epithelium function as stem/progenitor cells for smooth muscle cells, which become distributed along the elongating airways (De Langhe et al. Dev Biol. 2006 Nov. 1; 299(1): 52-62; Mailleuix et al. Development. 2005 May; 132(9): 2157-66). In other studies, mesenchymal stromal cells adjacent to the trachea and extrapulmonary bronchi have also been shown to give rise to bronchiolar smooth muscle cells (Shan et al. Dev Dyn. 2008; 237: 750-5). Collectively, these studies suggest that at least two distinct populations of mesenchymal stromal cells endowed with epithelial modulating properties emerge during development.

Several studies have identified resident mesenchymal stromal cells in adult lungs with the capacity for adipogenic, chondrogenic, osteogenic, and myogenic differentiation. These cells have been clonally expanded from heterogeneous populations of mixed lineage cells defined by their ability to efflux Hoechst 33342 (Giangreco et al. Am J Physiol Lung Cell Mol Physiol. 2004; 286: L624-30; Summer et al. Am J Respir Cell Mol Biol. 2007; 37: 152-9), by their capacity for outgrowth from lung explant cultures (Hoffman et al. Stem Cells Dev. 2011; 20: 1779-92) or by their characteristic expression of Sca-1 (McQualter et al. Stem Cells. 2009; 27: 612-22; Hegab et al. Stem Cells Dev. 2010; 19: 523-36). In addition, further enrichment of $CD45^{neg}$ $CD31^{neg}$ $Sca-1^{pos}$ mesenchymal stromal cells has been achieved based on their lack of EpCAM expression, which selectively labels epithelial lineage cells (McQualter et al. Proc Natl Acad Sci USA 2010; 107:1414-19). Resolution of the mesenchymal and epithelial lineages has revealed that the endogenous lung mesenchymal stromal cell population is necessary and sufficient to support the proliferation and differentiation of bronchiolar epithelial stem/progenitor cells in coculture (Id.). This suggests that adult mesenchymal stromal cells share similar epithelial inductive properties to their embryonic counterparts and are an important element of the epithelial stem/progenitor cell niche in the adult lung. This concept is also supported by recent in vivo studies showing that following naphthalene injury of club cells, parabronchial mesenchymal cells secrete FGF-10 to support epithelial regeneration from surviving epithelial stem/progenitor cells (Volckaert et al. J Clin Invest. 2011; 121: 4409-19).

Lung Endothelial Progenitor Cells

Endothelial-epithelial cell interactions and angiogenic and angiocrine factors elaborated in the lung epithelial stem/progenitor cell microenvironment also play a role in the regulation of endogenous lung epithelial stem/progenitor cell regeneration and repair (Yamamoto et al. Dev Biol. 2007 Aug. 1; 308(1) 44-53; Ding et al. Cell. 2011 Oct. 28; 147(3): 539-53; Crivellato. Int J Dev Biol. 2011; 55(4-5): 365-75); Grinnell & Harrington. Pulmonary endothelial cell interactions with the extracellular matrix. In: Voelkel N F, Rounds S, eds. The Pulmonary Endothelium: Function in Health and Disease. Chichester, West Suxssex: Wiley-Blackwell, 2009: 51-72). For example, it has been reported that the coculture of human vascular endothelial cells with a human bronchial epithelial cell line promotes the generation of branching bronchioalveolar epithelial structures in a 3D culture system (Frazdottir et al. Respir Res. 2010; 11: 162). While considerable progress has been made in understanding the heterogeneity, functional diversity, and pathophysiological behavior of lung vascular and microvascular endothelial cells, the immunophenotypic profiling, quantitation, and functional analysis of lung endothelial progenitor cells (EPC) lags far behind. As for EPC derived from human umbilical cord blood, bone marrow, and mobilized peripheral blood (Timmermans et al. J Cell Mol Med. 2009; 13: 87-102), the rarity of EPC in the lung, their lack of distinguishing markers, and the inability to discriminate circulating EPC and tissue resident EPC have been major impediments in assessing the contribution of endogenous lung EPC in lung vascular repair, and lung regeneration and remodeling (Thebaud & Yoder. Pulmonary endothelial progenitor cells. In: Voelkel N F, Rounds S, eds. The Pulmonary Endothelium: Function in Health and Disease. Chichester, West Sussex: Wiley, 2009: 203-16; Yoder. Proc Am Thorac Soc. 2011; 8: 466-70).

Lung macrovascular and microvascular endothelial cells can be resolved on the basis of their preferential binding to the lectins *Helix pomatia* and *Griffonia simplicifolica*, respectively (King et al. Microvasc Res. 2004; 67: 139-51), but there are no other cell surface markers that can discriminate mature lung endothelial cells and EPC (Yoder. Proc Am Thorac Soc. 2011; 8: 466-70). In addition, the rarity of EPC has necessitated the ex vivo expansion and passaging of adherent heterogeneous rat (Alvarez et al. Am J Physiol Lung Cell Mol Physiol. 2008; 294: L419-30) or mouse (Schniedermann et al. BMC Cell Biol. 2010; 11:50) lung endothelial cells in liquid culture prior to quantitation and flow cytometric and functional analysis of lung-derived EPC in in vitro assays. These assays suggest that the lung microvasculature is a rich source of EPC. However, the incidence, immunophenotypic and functional properties of EPC in the primary explanted endothelial cells compared with their ex vivo manipulated, selected, and expanded counterparts remains indeterminate. The ability of these endogenous lung EPCs to contribute to vascular repair and remodeling in vivo is also unproven (Yoder. Proc Am Thorac Soc. 2011; 8: 466-70). Recent studies suggest it likely that both circulating EPC and resident lung EPC contribute to endothelial cell regeneration and repair (Balasubramian et al. Am J Physiol Lung Cell Mol Physiol. 2010; 298: L315-23; Duong et al. Angiogenesis. 2011: 411-22; Chamoto et al. Am J Respir Cell Mol Biol. 2012 March; 46(3): 283-9).

General Principles of Wound Healing

The term "wound healing" refers to the processes by which the body repairs trauma to any of its tissues, especially those caused by physical means and with interruption of continuity.

A wound-healing response can be viewed as comprising four separate phases, comprising: 1) an initial phase post injury involving hemostasis; 2) a second phase involving inflammation; 3) a third phase involving granulation and proliferation; and 4) a fourth phase involving remodeling and maturation. The culmination of the wound-healing response results in the replacement of normal tissue structures with fibroblastic mediated scar tissue. Processes involved in the wound healing response, however, can go awry and produce an exuberance of fibroblastic proliferation, which can result in tissue damage, including hypertrophic scarring (a widened or unsightly scar that does not extend the original boundaries of the wound).

Initial Phase—Hemostatsis

An initial injury results in an outflow of blood and lymphatic fluid. This is also the process during which the initial reparative blood clot is created. Both the intrinsic coagulation pathways, so called because all of the components are intrinsic to plasma, and the extrinsic coagulation pathways are activated. The intrinsic and extrinsic systems converge to activate the final common pathways causing fibrin formation. FIG. 1 shows an illustrative representation of the classical coagulation cascades. It is generally recognized that these systems function together and interact in vivo.

The intrinsic coagulation pathway is initiated when blood contacts any surface except normal endothelial and blood cells. This pathway, also known as the contact activation pathway, begins with formation of the primary complex on collagen by high-molecular weight kininogen (HMWK), prekallikrein, and coagulation factor (Factor) XII (Hageman factor). Prekallikrein is converted to kallikrein and Factor XII becomes Factor XIIa. Factor XIIa converts Factor XI into Factor XIa. Factor XIa activates Factor IX, which, with its co-factor FVIIIa form the tenase complex, which activates Factor X to Factor Xa.

The extrinsic coagulation pathway, also known as the tissue factor pathway, generates a thrombin burst and is initiated when tissue thromboplastin activates Factor VII. Upon vessel injury, tissue factor (TF), a nonenzymatic lipoprotein cofactor that greatly increases the proteolytic efficiency of Factor VIIa, is exposed to the blood and enzyme coagulation factor VII (proconvertin) circulating in the blood. Once bound to TF, Factor VII is activated to Factor VIIa by different proteases, including thrombin (Factor IIa), Factors Xa, IXa, XIIa and the Factor VIIa-TF complex itself. The Factor VIIa-TF complex activates Factors IX and X. The activation of Factor Xa by the Factor VIIa-TF complex almost immediately is inhibited by tissue factor pathway inhibitor (TFPI). Factor Xa and its cofactor Va form the prothrombinase complex which activates the conversion of prothrombin to thrombin. Thrombin then activates other components of the coagulation cascade, including Factors V and VIII (which activates Factor XI, which, in turn, activates Factor IX), and activates and releases Factor VIII from being bound to von Willebrand Factor (vWF). Factors VIIa and IXa together form the "enase" complex, which activates Factor X, and so the cycle continues.

As currently understood, coagulation in vivo is a 3-step process centered on cell surfaces. FIG. 2 shows an illustration of the cell-surface based model of coagulation in vivo (Monroe Arterioscler Thromb Vase Biol. 2002; 22:1381-1389). In the first step, coagulation begins primarily by initiation with tissue factor, which is present on the subendothelium, tissues not normally exposed to blood, activated monocytes and endothelium when activated by inflammation. Factors VII and VIIa bind to tissue factor and adjacent collagen. The factor VIIa-tissue factor complex activates factor X and IX. Factor Xa activates factor V, forming a prothrombinase complex (factor Xa, Va and calcium) on the tissue factor expressing cell. In the second step, coagulation is amplified as platelets adhere to the site of injury in the blood vessel. Thrombin is activated by platelet adherence and then acts to fully activate platelets, enhance their adhesion and to release factor V from the platelet a granules. Thrombin on the surface of activated platelets activates factors V, VIII and XI, with subsequent activation of factor IX. The tenase complex (factors IXa, VIIIa and calcium) now is present on platelets where factor Xa can be produced and can generate another prothrombinase complex on the platelet so that there can be large-scale production of thrombin. Propagation, the third step, and is a combination of activation of the prothrombinase complexes that allow large amounts of thrombin to be generated from prothrombin. More platelets can be recruited, as well as activation of fibrin polymers and factor XIII.

The inflammatory phase (see below) begins during the hemostasis phase. Thrombocytes, as well as recruited white blood cells, release numerous factors to ramp up the healing process. Alpha-granules liberate platelet-derived growth factor (PDGF), platelet factor IV, and transforming growth factor beta (TGF-β). The processes of inflammation, collagen degradation and collagenogenesis, myoblastic creation from transformed fibroblasts, growth of new blood vessels, and reepithelialization are mediated by a host of cytokines and growth factors. The interleukins strongly influence the inflammatory process. Vascular endothelial growth factor (VEGF) and other factors enhance blood vessel formation, and some have multiple roles, such as fibroblast growth factor (FGF)-2, which affects not only the process of angiogenesis but also that of reepithelialization. Vasoactive amines, such as histamine and serotonin, are released from dense bodies found in thrombocytes. PDGF is chemotactic for fibroblasts and, along with TGF-β, is a potent modulator of fibroblastic mitosis, leading to prolific collagen fibril construction in later phases. Fibrinogen is cleaved into fibrin, and the framework for completion of the coagulation process is formed. Fibrin provides the structural support for cellular constituents of inflammation. This process starts immediately after the insult and may continue for a few days.

Second Phase: Inflammation

The early component of the inflammatory phase is predominated by the influx of the polymorphonuclear leukocytes (PMNs) and the later component of the inflammatory phase is predominated by monocytes/macrophages.

Within the first 6-8 hours, PMNs engorge the wound. TGF-β facilitates PMN migration from surrounding blood vessels, from which they extrude themselves from these vessels. These cells cleanse the wound, clearing it of debris. The PMNs attain their maximal numbers in 24-48 hours and commence their departure by hour 72. Other chemotactic agents are released, including FGF, TGF-β and TGF-α, PDGF, and plasma-activated complements C3a and C5a (anaphylactic toxins). They are sequestered by macrophages or interred within the scab or eschar (Id.; Habif. Dermatologic surgical procedures. Clinic Dermatology: A Color Guide to Diagnosis and Therapy. 3$^{rd}$ ed. 1996. 809-810).

As the process continues, monocytes also exude from surrounding blood vessels. Once they leave the vessel, these are termed macrophages. The macrophages continue the cleansing process, manufacture various growth factors during days 3-4, and orchestrate the multiplication of endothelial cells with the sprouting of new blood vessels, the duplication of smooth muscle cells, and the creation of the milieu created by the fibroblast. Many factors influencing the wound healing process are secreted by macrophages, including TGFs, cytokines and interleukin (IL)-1, tumor necrosis factor (TNF), and PDGF.

Third Phase: Granulation and Proliferation

The granulation and proliferation phase consists of an overall and ongoing process, comprising subphases termed the "fibroplasia, matrix deposition, angiogenesis and re-epithelialization" subphases (Cho & Lo. Dermatol Clin. 1998 January; 16(1): 25-47).

By days 5-7, fibroblasts have migrated into the wound, laying down new collagen of subtypes I and III. Early in normal wound healing, type III collagen predominates but is later replaced by type I collagen.

Tropocollagen is the precursor of all collagen types and is transformed within the cell's rough endoplasmic reticulum, where proline and lysine are hydroxylated. Disulfide bonds are established, allowing 3 tropocollagen strands to form a triple left-handed triple helix, termed procollagen. As the procollagen is secreted into the extracellular space, peptidases in the cell membrane cleave terminal peptide chains, creating true collagen fibrils.

The wound is suffused with glycosaminoglycans (GAGs) and fibronectin produced by fibroblasts. These GAGs include heparin sulfate, hyaluronic acid, chondroitin sulfate, and keratin sulfate. Proteoglycans are GAGs that are bonded covalently to a protein core and contribute to matrix deposition.

Angiogenesis results from parent vessel offshoots. The formation of new vasculature requires extracellular matrix and basement membrane degradation followed by migration, mitosis, and maturation of endothelial cells. Basic FGF and vascular endothelial growth factor are believed to modulate angiogenesis.

Re-epithelization occurs with the migration of cells from the periphery of the wound and accessory or adjoining tissues. This process commences with the spreading of cells within 24 hours. Division of peripheral cells occurs in hours 48-72, resulting in a thin epithelial cell layer, which bridges the wound. Epidermal growth factors are believed to play a key role in this aspect of wound healing.

This succession of subphases can last up to 4 weeks in the clean and uncontaminated wound.

Fourth Phase: Remodeling and Maturation

After the third week, the wound undergoes constant alterations, known as remodeling, which can last for years after the initial injury occurred. Collagen is degraded and deposited in an equilibrium-producing fashion, resulting in no change in the amount of collagen present in the wound. The collagen deposition in normal wound healing reaches a peak by the third week after the wound is created. Contraction of the wound is an ongoing process resulting in part from the proliferation of specialized fibroblasts termed myofibroblasts, which provide mechanical support and integrity to the tissue after initial injury. Wound contraction occurs to a greater extent with secondary healing (i.e., healing by second intention, which describes a wound left open and allowed to close by reepithelialization and contraction by myofibroblasts) than with primary healing (i.e., healing by first intention, which describes a wound closed by approximation of wound margins or by placement of a graft or flap, or wounds created and closed in the operating room, unlike via reepithelialization and contraction by myofibroblasts). Maximal tensile strength (the greatest longitudinal stress a substance can bear without tearing apart) of the wound is achieved by the 12th week, and the ultimate resultant scar has only 80% of the tensile strength of the original skin that it has replaced. At the end of tissue repair, the reconstructed ECM takes over the mechanical load and myofibroblasts disappear by massive apoptosis (Tomasek et al. Nat Rev Mol Cell Biol. 2002 May; 3(5): 349-63).

Fibroblastic Cells and Myofibroblast Differentiation in Normal Conditions

Under normal conditions, fibroblastic cells exhibit few or no actin-associated cell-cell and cell-matrix contacts and little ECM production (Tomasek et al. Nat Rev Mol Cell Biol. 2002 May; 3(5): 349-63), but after tissue injury, they become activated to migrate into the damaged tissue and to synthesize ECM components (Hinz. J Invest Dermatol. 2007 March; 127(3): 526-37) by cytokines locally released from inflammatory and resident cells (Werner & Grose. Physiol Rev. 2003 July; 83(3): 835-70) or from malignant epithelial cells (De Wever & Mareel. J Pathol. 2003 July; 200(4): 429-47).

Another important stimulus for this phenotypic transition is the change of the mechanical microenvironment; whereas fibroblasts in intact tissue are generally stress-shielded by the crosslinked ECM, this protective structure is lost in the continuously remodeled ECM of injured tissue (Tomasek et al. Nat Rev Mol Cell Biol. 2002 May; 3(5): 349-63). In response to mechanical challenge, fibroblasts acquire contractile stress fibers that are first composed of cytoplasmic actins (Tomasek et al. Nat Rev Mol Cell Biol. 2002 May; 3(5): 349-63), hallmarking the "protomyofibroblast." Stress fibers are connected to fibrous ECM proteins at sites of integrin-containing cell-matrix junctions (Hinz. Eur J Cell Biol. 2006 April; 85(3-4): 175-81) and between cells via de novo established N-cadherin-type adherens junctions (Hinz et al. Mol Biol Cell. 2004 September; 15(9): 4310-20).

In culture, protomyofibroblasts are a stable phenotype, representing an intermediate step in most in vivo conditions where they proceed toward the "differentiated myofibroblast" that is characterized by de novo expression of α-smooth muscle actin (α-SMA), its most commonly used molecular marker, and by increased production of ECM proteins. Expression of α-SMA in stress fibers confers to the differentiated myofibroblast at least a twofold stronger contractile activity compared with α-SMA-negative fibroblasts in culture (Hinz et al. Am J Pathol. 2007 June; 170(6): 1807-16).

At least three local events are needed to generate α-SMA-positive differentiated myofibroblasts: 1) accumulation of biologically active transforming growth factor (TGF) β1; 2) the presence of specialized ECM proteins like the ED-A splice variant of fibronectin; and 3) high extracellular stress, arising from the mechanical properties of the ECM and cell remodeling activity (Tomasek et al. Nat Rev Mol Cell Biol. 2002 May; 3(5): 349-63). Mechanoperception is mediated by specialized cell-matrix junctions, called "fibronexus" in vivo and "supermature focal adhesions" (FAs) in vitro (Hinz. Eur J Cell Biol. 2006 April; 85(3-4): 175-81). Analogously, small N-cadherin-type cell-cell adhesions develop into larger OB-cadherin (cadherin-11)-type junctions during generation of the differentiated myofibroblast in vitro and in vivo (Hinz et al. Mol Biol Cell. 2004 September; 15(9): 4310-20; Hinz et al. Am J Pathol. 2007 June; 170(6): 1807-16).

The main myofibroblast inducer TGFβ1 up-regulates expression of fibronectin and its integrin receptors in lung fibroblasts; this is closely linked to the activation/phosphorylation of focal adhesion kinase essential for the induction of myofibroblast differentiation (Thannickal et al. *J Biol Chem.* 2003 Apr. 4; 278(14): 12384-9). At the end of tissue repair, the reconstructed ECM again takes over the mechanical load and myofibroblasts disappear by massive apoptosis (Tomasek et al. Nat Rev Mol Cell Biol. 2002 May; 3(5): 349-63); stress release is a powerful promoter of myofibroblast apoptosis in vivo (Hinz et al. Am J Pathol. 2007 June; 170(6): 1807-16).

After injury, the main myofibroblast progenitor appears to be the locally residing fibroblast, which transiently differentiates into a protomyofibroblast, characterized by α-SMA-negative stress fibers. In the lung, the endothelial-to-mesenchymal transition (the biologic process that allows an epithelial cell to undergo multiple biochemical changes that enable it to assume a mesenchymal cell phenotype (Kalluri & Weinberg. J Clin Invest. 2009 Jun. 1; 119(6): 1420-28)) may provide an additional mechanism to generate fibroblasts (Hinz et al. Am J Pathol. 2007 June; 170(6): 1807-16).

Pulmonary Fibrosis

Pulmonary fibrosis, an interstitial lung disease, is a general term used to describe an increased accumulation of extracellular matrix ("ECM") in the distal lung, rendering the lung stiff and compromising its ability to facilitate normal gas exchange. Patients typically present with the insidious onset of shortness of breath with exertion as the disease often goes unnoticed in its early stages. Pulmonary fibrosis can be associated with a number of underlying diseases (such as connective tissue/rheumatologic disease) or environmental exposures (asbestosis), or it can be idiopathic, i.e., of unknown cause, in nature (Barkauskas & Nobel. Am J Physiol Cell Physiol. 2014 Jun. 1; 306(11): C987-96).

Progressive tissue fibrosis is a major cause of morbidity, and idiopathic pulmonary fibrosis (IPF) is a terminal illness characterized by unremitting ECM deposition in the lung with very limited choice of therapies (Noble et al. J Clin Invest. 2012 August; 122(8): 2756-62). Although certain mediators have been identified as initiating progressive fibrosis, the mechanisms that contribute to the disease are unknown.

IPF, a chronic, terminal disease that manifests over several years, is the most common form of fibrotic lung disease with a prevalence of 14.0-42.7 cases per 100,000 individuals in the United States (depending on the case definition used) and a median survival of 2.5-3.5 yr (Raghu et al. Am J Respir Crit Care Med. 2006 Oct. 1; 174(7): 810-6). It is characterized by excess ECM components and scar tissue within the lungs, and exercise-induced breathlessness and chronic dry cough are the prominent symptoms. IPF is viewed as a disease of aging, with the median age at diagnosis being in the mid-60s. There are few effective therapies for IPF short of lung transplant (Meltzer and Nobel. Orphanet J Rare Dis. 2008 Mar. 26; 3: 8. Doi: 10, 1186/1750-1172-3-8). Because a pharmacologic therapy capable of halting or at least slowing the progression of the disease has been elusive, there are intense efforts to better understand the factors that trigger and perpetuate this disease.

IPF belongs to a family of lung disorders known as interstitial lung diseases ("ILD"), or more accurately, the diffuse parenchymal lung diseases ("DPLD"). Within this broad category of diffuse lung diseases, IPF belongs to the subgroup known as idiopathic interstitial pneumonia ("IIP"). By definition, the etiology of IIP is unknown. There are seven distinct IIPs, differentiated by specific clinical features and pathological patterns (Katzenstein et al. Am J Respir Crit Care Med. 2008 April; 157(4 Pt 1): 1301-15). IPF is the most common form of IIP, and is associated with the pathologic pattern known as usual interstitial pneumonia (UIP). The UIP patter of fibrosis is characterized by two features: 1) Spatial or geographic heterogeneity, which refers to a patchy distribution of dense lung scarring with areas of less affected or normal lung tissue; and 2) Temporal heterogeneity, which refers to areas of densely collagenized fibrosis with variable smooth muscle proliferation alternating with active fibroblast foci (Smith et al. J Clin Pathol. 2013 October; 66(1): 896-903). Therefore, IPF is often referred to as IPF/UIP. IPF is usually fatal, with an average survival of approximately three years from the time of diagnosis (Collard et al. Am J Respir Crit Care Med. 2003 Sep. 1; 168(5): 538-42; Flaherty, et al. Am J Respir Crit Care Med. 2003 Sep. 1; 168(5): 543-8; Latsi et al. Am J Respir Crit Care Med. 2003 Sep. 1; 168(5): 531-7).

IPF arises in the alveolar regions of the lung, a region that consists of AEC2s, and AEC1 s, as well as a number of mesenchymal cell types. It is hypothesized that cross talk between the alveolar epithelium and its associated mesenchyme is dysregulated in IPF pathogenesis, and this leads to the unchecked proliferation of extracellular matrix-producing cells. Evidence from genetic analysis of rare familial cases of IPF suggests that defects that incite the development of the disease can originate in the alveolar epithelium (Barkauskas & Noble. Am J Physiol Cell Physiol. 2014 Jun. 1; 306(11): C987-96).

Examples of non-medication based interventions for IPF include pulmonary rehabilitation, long-term oxygen therapy, mechanical ventilation, and lung transplantation. Of these treatments, the only intervention that improves survival in select patients with IPF is lung transplantation (Rafii et al. J Thorac Dis. 2013; 5(1): 48-73). However, lung transplantation is not without significant risks, including infection, given the need for immunosuppression, acute and chronic graft rejection, and airway stenosis (Id.).

Many proposed medication based treatments have failed to date (Id.). These include anti-inflammatory or immunomodulatory therapies, such as corticosteroid monotherapy, azathioprine, cyclophosphamide, everolimus; anticoagulants and therapies targeting the coagulation cascade, such as warfarin, heparin, and prednisolone; endothelin receptor antagonists and vasodilators, such as bosentan, ambrisentan, macitentan, and sildenafil; and antifibrotics and cytokine/kinase inhibitors, such as interferon-gamma, etanercept, imatinib, and CC-930 (Id.). Many of these failures have been associated with a high degree of side effects, which would be expected for medications of these classes, and limited therapeutic effects.

To date, two therapeutic medications have been FDA approved for the treatment of IPF. Esbriet® (pirfenidone), a small molecule antifibrotic that acts on multiple pathways, including the transforming growth factor beta (TGF-β) pathway, and Ofev® (nintedanib), a small molecule inhibitor of the receptors for tyrosine kinases, fibroblast growth factor (FGF), platelet-derived growth factor (PDGF), and vascular endothelial growth factor (VEGF). Although these medications have side effects and do not appear to be able to reverse IPF, they have been shown to significantly slow the progression of the disease.

Recently, microRNAs have shown promise as a therapeutic tool in the treatment of IPF. MicroRNAs (miRNAs) include a broad class of small evolutionarily conserved noncoding RNAs that have important roles in a variety of patho-physiological processes by blocking translation or promoting degradation of complementary target mRNAs (Wynn & Ramalingam. Nat Med. 2012 Jul. 6; 18(7): 1028-40). Although unique subsets of miRNAs have been identified in various fibrotic diseases, a much smaller subset of miRNAs have emerged as regulators of the fibrotic process. For example, miR-21 is expressed in the lungs of individuals with IPF, and mice treated with miR-21 antisense probes were protected from bleomycin-induced pulmonary fibrosis (Liu et al. J Exp Med. 2010 Aug. 2; 207(8): 1589-97). Mechanistically, miR-21 is thought to promote fibrosis by regulating TGF-β1 and MAP kinase signaling in activated myofibroblasts (Id.), and miR-29 also seems to promote fibrosis in human cells by directly regulating type I collagen expression (Ogawa et al. Biochem Biophys Res Commun. 2010 Jan. 1; 391(1): 316-21). In addition, miR-29 has been found to be down regulated in various forms of fibrosis, including IPF. Animal studies injecting a miR-29 mimic into mice has demonstrated promising results even in cases of "established fibrosis." (Fox. Drug Discovery & Development—http://www.dddmag.com/news/2014/10/reversing-idiopathic-pulmonary-fibrosis).

Wound Healing in Pulmonary Fibrosis

Pulmonary fibrosis is hypothesized to develop because of epithelia injuries and/or cellular stress is met by a dysregulated mesenchymal response, leading to a deposition of excess collagen and other ECM components into the fibrotic lung (Barkauskas & Noble. Am J Physiol Cell Physiol. 2014 Apr. 16; 306L C987-96).

The wound healing response is dysregulated in pulmonary fibrosis, and disruptions to the highly coordinated wound-repair processes result in pathological scar formation and excessive deposition of ECM components, such as collagen (Chambers. Eur Respir Rev. 2008; 17(109): 130-7). It is thought that in pulmonary fibrosis, aberrant activation of alveolar epithelial cells provokes the migration, proliferation, and activation of mesenchymal cells with the formation of fibroblastic/myofibroblastic foci, leading to the exaggerated accumulation of extracellular matrix with the irreversible destruction of lung tissue (Harari & Caminati. Allergy. 2010 May; 65(5):537-53).

Following injury or "wear and tear" to the alveolar epithelium in otherwise normal lungs, dead or damaged alveolar epithelial cells are replaced by descendants of AEC2s that self-renew and differentiate to AEC1s. It is hypothesized that Scgb1a1+ club secretory cells and/or basal cells serve as a source of AEC2s following injury. These repair processes effectively cover denuded basal lamina, and in the normal healing process, fibrosis does not occur (Barkauskas & Noble. Am J Physiol Cell Physiol. 2014 Jun. 1; 306(11): C987-96). However, in pulmonary fibrosis, abnormal AEC2s are observed, usually overlying fibroblast foci (Rock et al. Proc Natl Acad Sci USA. 2011 Dec. 27; 108(52): E1475-83). The abnormal, hyperplastic morphology of the AEC2s in IPF is thought to relate to cellular stress and the failure to regenerate AEC1 s lost by injury or wear and tear. The inability of defective AEC2s to cover the basement membrane denuded by the loss of AEC1 s, results the release of profibrotic signals and may perpetuate the development of fibroblast foci (Id.).

In addition to activating the coagulation cascade, platelets and damaged epithelial and endothelial cells release a variety of chemotactic factors that recruit inflammatory monocytes and neutrophils to the site of tissue damage (Wynn & Ramalingam. Nat Med. 2012 Jul. 6; 18(7): 1028-40).

Various growth factors and cytokines secreted by innate inflammatory cells (including macrophages, neutrophils, mast cells and eosinophils) have emerged as potential targets for antifibrotic therapy (Id.). Tumor necrosis factor-α (TNF-α) and interleukin-1 (IL-1β), in particular, have been identified as important targets in a variety of fibrotic diseases (Zhang et al. J Immunol. 1993 May 1; 150(9): 4188-96). Mice that overexpress TNF-α or IL-1β in the lung develop highly progressive pulmonary fibrosis (Miyazaki et al. J Clin Invest. 1995 July; 96(1): 250-9; Kolb et al. J Clin Invest.

2001 June; 107(12): 1529-36). Studies have also shown an essential role for TNF-α in the development of silica- and bleomycin-induced pulmonary fibrosis in mice (Piguet et al. Nature. 1990 Mar. 15; 344(6263): 245-7; Piguet et al. J Exp Med. 1989 Sep. 1; 170(3): 655-63). In support of these experimental findings, patients with idiopathic or systemic sclerosis-associated pulmonary fibrosis have high levels of TNF-α (Piguet et al. Am J Pahtol. 1993 September; 143(3): 651-5). Other studies have documented profibrotic activity for IL-1β and NALP3/ASC inflammasome signaling in macrophages (Gasse et al. J Clin Invest. 2007 December; 117(12): 3786-99). Pulmonary fibrosis induced by bleomycin and silica is reduced in IL-1β-deficient mice (Bujak et al. Arch Immulon Ther Exp (Warsz). 2009 May-June; 57(3): 165-76: Jones et al. Nephrol Dail Transplant. 2009; 24: 3024-32; Kamari et al. J Hepatol. 2011 November; 55(5): 1086-94). Like TNF-α, IL-1β is a potent proinflammatory mediator that exacerbates parenchymal-cell injury. It also induces epithelial-mesenchymal transition (EMT) and myofibroblast activation through a TGF-β1-mediated mechanism (Fan et al. Am J Kidney Dis. 2001 April; 37(4): 820-31), confirming that it functions as a potent upstream driver of fibrosis. IL-1β and TNF-α also increase expression of IL-6, which shows autocrine growth-factor activity in fibroblasts. Studies suggest that the cellular source of TGF-β1 dictates its activity, with TGF-β1 derived from macrophages generally showing wound-healing and profibrotic activity and TGF-β1 secreted from CD4+T regulatory cells ($T_{reg}$ cells) functioning as an anti-inflammatory and antifibrotic mediator (Kitani et al. J Exp Med. 2003 Oct. 20; 198(8): 1179-88). Mice deficient in TGF-β1 develop numerous autoimmune disorders and are more susceptible to cancer (Id.).

The CD4+$T_H$17 cell subset that expresses the proinflammatory cytokine IL-17A is emerging as a driver of fibrosis. IL-17A expression has been implicated in the pathogenesis of pulmonary fibrosis (Wilson et al. J Exp Med. 2010 Mar. 15; 207(3): 535-52). In many cases, IL-17A expression is associated with persistent neutrophilia (Laan et al. J Immunol. 1999 Feb. 15; 162(4): 2347-52), and it has been suggested that exaggerated neutrophil recruitment contributes to the development of tissue damage and fibrosis by inducing apoptosis in vascular endothelial cells (Zhu et al. Clin Immunol. 2011 November; 141(2): 152-60). Neutrophil recruitment is also an important predictor of early mortality in IPF patients (Kinder et al. Chest. 2008 January; 133(1): 226-32). Mechanistic studies investigating the IL-17 pathway of fibrosis in mice have identified the proinflammatory cytokines IL-1β and IL-23 as important upstream initiators of profibrotic $T_H$17 responses (Wilson et al. J Exp Med. 2010 Mar. 15; 207(3): 535-52; Gasse et al. PLoS One. 2011; 6(8): e23185). A link between IL-17A and TGF-β1 has also been identified (Wilson et al. J Exp Med. 2010 Mar. 15; 207(3): 535-52). In addition to its role in promoting neutrophilic inflammation, IL-17A has been shown to directly induce expression of matrix metalloproteinase-1 in primary human cardiac fibroblasts (Cortez et al. Am J Physiol Heart Circ Physiol. 2007 December: 293(6): H3356-65), suggesting that IL-17A promotes fibrosis by both exacerbating the upstream inflammatory response and regulating the downstream activation of fibroblasts (Wynn & Ramalingam. Nat Med. 2012 Jul. 6; 18(7): 1028-40).

IL-13 has emerged as a dominant mediator of fibrotic tissue remodeling in several experimental and natural models of fibrosis (Chiaramonte et al. J Clin Invest. 1999 September; 104(6): 777-85). IL-13 production has been implicated in the development of IPF (Murray et al. Int J Biochem Cell Biol. 2008; 40(10): 2174-82). Mechanistically, IL-13 has been hypothesized to induce fibrosis by stimulating the production and activation of TGF-β (Lee et al. J Exp Med. 2001 Sep. 17; 194(6): 809-21). Other studies have suggested that IL-13 can promote fibrosis independently of TGF-β (Liu et al. J Immunol. 2011 Sep. 1; 187(5): 2814-23; Kaviratne et al. J Immunol. 2004 Sep. 15; 173(6): 4020-9) by directly activating the synthetic and proliferative properties of fibroblasts, epithelial cells and smooth-muscle cells (Kuperman et al. Nat Med. 2002 August; 8(8): 885-9; Lee et al. Am J Respir Cell Mol Biol. 2001 October; 25(4): 474-85). Unlike IL-17A—which seems to promote fibrosis indirectly by inducing tissue damage and inflammation-IL-13 and TGF-β show direct fibrotic activity. $T_H$2 cells that produce IL-13 and $T_{reg}$ cells that express TGF-β are also known to inhibit $T_H$17 responses (Wilson et al. Gastroenterology. 2011 January; 140(1): 254-64), suggesting dual roles for IL-13 and TGF-β in the wound-healing response, as both cytokines suppress inflammation while promoting fibrosis. The profibrotic activity of IL-13 is controlled by the abundance of the IL-13Rα1 signaling receptor and IL-13Rα2 decoy receptor expressed on target cells such as myofibroblasts (Ramalingam et al. Nat Immunol. 2008 January; 9(1): 25-33; Chiaramonte et al. J Exp Med. 2003 Mar. 17; 197(6): 687-701). When decoy receptor expression is low or absent, IL-13-dependent fibrosis is exacerbated (Mentink-Kane et al. Gastroenterology. 2011 December; 141(6): 2200-9). However, mice deficient in IL-13Rα2 are more resistant to IL-1β- and IL-17-driven inflammation, probably because of the enhanced IL-13 activity (Wilson et al. Gastroenterology. 2011 January; 140(1): 254-64), suggesting that IL-13Rα2 functions as a key regulator of both $T_H$17-mediated inflammation and $T_H$2-driven fibrosis (Mentink-Kane & Wynn. Immunol Rev. 2004 December; 202: 191-202).

Mechanistically, IFN-γ is believed to inhibit fibrosis, at least in part, by antagonizing the profibrotic activity of TGF-β1. IFN-γ inhibits the TGF-β-induced phosphorylation of the signal transducer Smad3 and subsequent activation of TGF-α-responsive genes (Ulloa et al. Nature 1999 Feb. 25; 397(6721): 710-3). IFN-γ also acts through a pathway dependent on Janus-associated kinase (Jak1) and the transcription factor Stat1 and induces expression of Smad7, which can prevent the interaction of Smad3 with the TGF-β receptor, thus further attenuating TGF-β-induced signaling. IFN-γ also directly inhibits fibroblast proliferation, TGF-β1-induced expression of the genes encoding procollagen I and procollagen III, and collagen synthesis in activated myofibroblasts. IFN-γ also prevents the $T_H$2 cytokine-induced differentiation of CD14+ peripheral blood monocytes into fibroblast-like cells called fibrocytes, which are believed to participate in the development of fibrosis in many organ systems Shao et al. J Leukoc Biol. 2008 June; 83(6): 1323-33). By virtue of its ability to stimulate IFN-γ production in $T_H$1 and natural killer cells, IL-12 has shown similar antifibrotic activity in vivo in mice (Wynn et al. Nature. 1995 Aug. 17; 376(6541): 594-6: Keane et al. Am J Physiol Lung Cell Mol Physiol. 2001 July; 281(1): L92-7). But despite an abundance of in vitro and in vivo evidence supporting an antifibrotic role for $T_H$1-type immunity, clinical studies investigating the therapeutic potential of IFN-γ in the treatment of IPF, systemic sclerosis and other fibrotic disorders have so far been mostly unsuccessful (King et al. Lancet. 2009 Jul. 18; 374(9685): 222-8).

The circulating myeloid cells respond to a gradient of CCL2 and are recruited to damaged tissues, where they differentiate into macrophages that phagocytose the fibrin clot and cellular debris.

Macrophages that appear early in the wound-healing response are also major producers of TGF-β, which is one of the drivers of fibrosis (Wynn & Ramalingam. Nat Med. 2012 Jul. 6; 18(7): 1028-40). Macrophages have also been implicated in the pathogenesis of fibrosis (Wynn & Ramalingam. Nat Med. 2012 Jul. 6; 18(7): 1028-40). Recent literature indicates that various factors should be taken in account in evaluating macrophage activity (Martinez & Gordon. F1000Prime Rep. 2014; 6: 13). Martinez & Gordon have hypothesized that macrophages do not form stable subsets but respond to a combination of factors present in tissues, that various pathways interact to form complex, even mixed, macrophage phenotypes (Id.).

Although it is widely recognized that monocytes, macrophages and neutrophils have important roles in the progression and resolution of fibrosis (Wynn & Barron. Semin Liver Dis. 2010 August; 30(3): 245-57), other myeloid-lineage cells (such as mast cells, eosinophils and basophils) have also been implicated in the pathogenesis of fibrosis in multiple organ systems (Wynn & Ramalingam. Nat Med. 2012 Jul. 6; 18(7): 1028-40). Mechanistic studies in rats have suggested that mast cells promote fibrosis by recruiting inflammatory leukocytes and by producing profibrotic mediators (Levick et al. Hypertension. 2009 June; 53(6): 1041-7). Eosinophils seem to function in a similar fashion and are considered to be important sources of TGF-β1 and IL-13 (Reiman et al. Infect Immun. 2006 Mar.; 74(3): 1471-9; Minshall et al. Am J Respir Cell Mol boil. 1997 September; 17(3): 326-33). Eosinophils have been most commonly associated with the development of pulmonary fibrosis (Humbles et al. Science. 2004 Sep. 17; 305(5691): 1776-9. Bronchoalveolar-lavage eosinophilia has also been identified as a predictive biomarker of progressive lung disease in IPF and pulmonary fibrosis associated with collagen vascular disorder (Peterson et al. Chest. 1987 July; 92(1): 51-6). Although basophils have a less clear role in the development of fibrosis than the other myeloid-cell populations, they have been implicated in the pathogenesis of myelofibrosis and are frequently found in greater numbers in patients with interstitial lung disease (Gilbert. Prog Clin Biol Res. 1984; 154: 3-17).

ECM fragments, including hyaluronan, have also been shown to be important drivers of fibrosis by stimulating chemokine and proinflammatory cytokine production by inflammatory monocytes and macrophages (Li et al. J Exp Med. 2011 Jul. 4; 208(7): 1459-71).

While in normal wound healing, myofibroblasts are lost via apoptosis when the tissue integrity has been sufficiently restored to be mechanically coherent (Darby et al. Lab Invest. 1990 July; 63(1): 21-9); Desmouliere et al. Am J Pathol. 1995 January; 146(1): 56-66), in the wound healing response in pulmonary fibrosis, myofibroblasts remain, failing to undergo apoptosis, and in turn lead to ongoing pathology of accumulation of collagen and other ECM components, and scarring (Darby et al. Clin Cosmet Investig Dermatol. 2014; 7: 301-11). In other words, in pulmonary fibrosis, there is a defect in the granulation and proliferation and remodeling phases; if the remodeling phase of the granulation tissue fails to happen (neither apoptosis of the cells present in the granulation tissue, myofibroblasts, and vascular cells, nor the reorganization of the ECM), myofibroblasts may persist, leading to pathological situations characterized by pulmonary fibrosis (Id.).

Fibroblastic Cells and Myofibroblast Differentiation in Fibrotic Conditions

Fibroblasts and myofibroblasts from IPF patients have been shown to have distinct properties, including the ability to invade the ECM. A hallmark and defining pathological feature of IPF is the formation of fibroblastic foci, which are the accumulation of myofibroblasts in the interstitium of the lung juxtaposed to the alveolar epithelium with destruction of the adjoining alveolar basement membrane (Selman & Pardo. Respir Res. 2002; 3: 3). The destruction of alveolar basement membrane was also observed in experimental lung fibrosis (Fukuda et al. Am J Pathol. 1985 March; 118(3): 452-75; Vaccaro et al. Am Rev Respir Dis. 1985 October; 132(4): 905-12). In view of the many characteristics that encompass features of fibrosis, such as the elaboration of ECM and expression/activation of TGFβ1 (Zhang et al. Am J Pathol. 1994 July; 145(1): 114-25); Zhang et al. J Immunol. 1994 Nov. 15; 153(10): 4733-41), the persistence of the myofibroblast is thought to be of significance in the propagation of fibrosis in pulmonary fibrosis. Early studies of the origin of the myofibroblast in lung injury and fibrosis suggest several possibilities based on observations of its cytoskeletal phenotype, tissue localization, and in vitro studies. Based on evidence that myofibroblasts arise de novo and on the kinetics of the induction of α-SMA expression, the perivascular and peribronchiolar adventitial fibroblasts, i.e., the local fibroblasts, are suggested as precursors (Zhang et al. Am J Pathol. 1994 July; 145(1): 114-25), but it has also been reported that circulating fibrocytes (expressing CD45, CD34, collagen I, and CXCR4) can migrate to sites of tissue injury and differentiate into myofibroblasts (Abe et al. J Immunol. 2001 Jun. 15; 166(12): 7556-62; Phillips et al. J Clin Invest. 2004 August; 114(3): 438-46).

The mechanism underlying the source of myofibroblasts in pulmonary fibrosis is complex; it has been determined that the presence of Smad3, an intracellular signal transducer for TGF-β1, may have an essential role in myofibroblast differentiation (Ramirez et al. Am J Transplant. 2006 September; 6(9): 2080-8; Hu et al. Am J Respir Cell Mol boil. 2007 January; 36(1): 78-84). However, regulation of the α-SMA gene is quite complex (Giannone & Sheetz. Trends Cell Biol. 2006 April; 16(4): 213-23; Ramirez et al. Am J Transplant. 2006 September; 6(9): 2080-8; Hu et al. Am J Respir Cell Mol boil. 2007 January; 36(1): 78-84). Additional transcription factors, including C/EBPP (CCAAT/enhancer-binding protein P), GKLF (gut-enriched Krippel-like factor), Sp1/Sp3, c-myb, and the downstream effector component of Notch signaling, have been implicated to regulate this gene in a complex and interactive manner, and in addition to inducers, suppressors such as the liver-enriched inhibitory protein isoform of C/EBPβ may serve to keep the precursor fibroblast in an undifferentiated state under normal homeostasis (Hinz et al. Am J Pathol. 2007 June; 170(6): 1807-16). Epigenetic modifications in fibroblasts also contribute to the pathogenesis of fibrosis by stably altering the activation status of myofibroblasts (Wynn & Ramalingam. Nat Med. 2012 Jul. 6; 18(7): 1028-40).

In pulmonary fibrosis, myofibroblasts are found in abundance in areas of high ECM expression and represent the predominant source of heightened ECM and cytokine gene expression (Zhang et al. Am J Pathol. 1994 July; 145(1): 114-25). The myofibroblast is a factor in alveolar epithelial apoptosis, denudation, and retardation of epithelial regeneration (Waghray et al. FASEB J. 2005 May; 19(7): 854-6). Thus, in addition to its potential contribution to reduction in lung tissue compliance, the myofibroblast is likely to play significant roles in promoting ECM deposition, release of inflammatory mediators, and epithelial injury, all of which are considered to be key factors in perpetuating the cycle of injury and fibrosis. As noted above, in pulmonary fibrosis, myofibroblasts fail to undergo apoptosis, as in the normal wound healing response, which leads to ongoing pathology of accumulation of collagen and other ECM components, and scarring (Darby et al. Clin Cosmet Investig Dermatol. 2014; 7: 301-11).

TGFβ1 can induce p38 mitogen-activated protein kinase pathway activation with subsequent activation of the pro-survival phosphatidylinositol 3-kinase-AKT pathway (Horowitz et al. J Biol Chem. 2004 Jan. 9; 279(2): 1359-67). Deficiency in PTEN, a phosphatidylinositol 3-kinase-AKT pathway inhibitor, is associated with increased myofibroblast differentiation (White et al. Am J Respir Crit Care Med. 2006 Jan. 1; 173(1): 112-21). Thus, in addition to promoting myofibroblast differentiation, combinatorial activation of the adhesion-dependent focal adhesion kinase pathway and the soluble growth factor-mediated AKT pathway confers apoptosis/anoikis (programmed cell death induced by anchorage-dependent cells detaching from surrounding ECM) resistance to TGFβ1-differentiated myofibroblasts (Horowitz et al. Cell Signal. 2007 April; 19(4): 761-71).

IPF Fibroblasts Possess a Malignant Phenotype with an Increased Capacity for Invasion It has been proposed that fibroblasts in the IPF lung acquire a phenotype that is reminiscent of malignant cells (Barkauskas & Noble. Am J Physiol Cell Physiol. 2014 Jun. 1; 306(11): C987-96). Fibroblasts from the IPF lung display enhanced migratory capacity when assessed in a chemotaxis chamber with platelet-derived growth factor (PDGF) as the chemoattractant. Fibroblasts from tissues with more dense fibrosis displayed capacity for migration compared with fibroblasts isolated from earlier stage disease (Suganuma et al. Thorax. 1995 September; 50(9): 984-9). IPF fibroblasts, compared with fibroblasts from normal human lung, display slower growth rates, higher rates of apoptosis, and a profibrotic secretory phenotype (Ramos et al. Am J Respir Cell Mol Biol. 2001 May; 24(5): 591-8). In addition, fibrotic lung fibroblasts, unlike normal fibroblasts and more consistent with cancer-derived cells, are able to survive in the absence of attachment and interaction with extracellular matrix and neighboring cells, displaying anchorage-independent growth in soft agar (Torry et al. J Clin Invest. 1994 April; 93(4): 1525-32).

IPF Fibroblasts Demonstrate Impaired Mechanosensitive Signaling

It has long been viewed that myofibroblasts, with their contractile properties, are key effector cells in wound healing (Barkauskas & Noble. Am J Physiol Cell Physiol. 2014 Jun. 1; 306(11): C987-96). After facilitating wound closure, these cells typically disappear from granulation tissue, presumably via a de-differentiation mechanism (Kisseleva et al. Proc Natl Acad Sci USA. 2012 Jun. 12; 109(24): 9448-53), a clearance mechanism (Friedman. Proc Natl Acad Sci USA. 2012 Jun. 12; 109(24): 9230-1; Krizhanovsky et al. Cell. 2008 Aug. 22; 134(4): 657-67), or a combination of both. In IPF, myofibroblasts are believed to persist inappropriately, leading to progressive fibrosis. It has been shown that mechanical stimuli (e.g., stiff extracellular matrix with myofibroblasts generating high contractile forces) can be converted to fibrogenic signals (e.g., liberation of TGF-β1), which, in turn, maintains the myofibroblastic phenotype (Wipff et al. J Cell Biol. 2007 Dec. 17; 179(6): 1311-23). An intrinsic mechanotransduction mechanism that promotes myofibroblast differentiation regulated by nuclear translocation of MKL1 (myocardin-related transcription factor-A, a mechanosensitive transcription factor that is involved in activating the fibrotic gene program) that results in stiff matrix-promoting aSMA gene expression by normal lung fibroblasts (Huang et al. Am J Respir Cell Mol Biol. 2012 September; 47(3): 340-8) has been described. These experiments were done by comparing (myo)fibroblast behavior on polyarylamide hydrogels of differing stiffness. This intrinsic mechanotransduction is mediated by the Rho kinase (ROCK) pathway, which regulates myofibroblast contractility, differentiation, and survival experiments (Zhou et al. J Clin Invest. 2013 March; 123(3): 1096-108). These experiments also demonstrated that preexisting myofibroblasts can be shuttled to an apoptotic fate if their contractile properties are disrupted (Barkauskas & Noble. Am J Physiol Cell Physiol. 2014 Jun. 1; 306(11): C987-96).

Mechanisms and Pathways of Fibrosis

Because ECM-secreting myofibroblasts are central to the pathogenesis of fibrotic diseases, fibrosis research has focused on elucidating the molecular and immunological mechanisms that initiate, maintain and terminate the differentiation of quiescent fibroblasts into actively proliferating, ECM-producing myofibroblasts (Wynn & Ramalingam. Nat Med. 2012 Jul. 6; 18(7): 1028-40). The mechanisms that control progressive fibrosis, however, are largely unknown (Li et al. J Exp Med. 2011 Jul. 4; 208(7): 1459-71).

Origin of Profibrotic Fibroblasts

The origin of fibrotic fibroblasts has been of great interest in understanding the pathogenesis of tissue fibrosis (Dulauroy et al. Nat Med. 2012 August; 18(8): 1262-70; Hung et al. Am J Respir Crit Care Med. 2013 Oct. 1; 188(7): 820-30; LeBleu et al. Nat Med. 2013 February; 19(2): 227-31; Rock et al. Proc Natl Acad Sci USA. 2011 Dec. 27; 108(52): E1475-83). Fibrotic fibroblasts in IPF are extremely heterogeneous (Jordana et al. Am Rev Respir Dis. 1988 March; 137(3): 579-84.), suggesting they may be raised from different cell types, or represent different stages of activation, or are influenced by their milieu (Zeisberg and Kalluri. Am J Physiol Cell Physiol. 2013 Feb. 1; 304(3): C216-25.). The heterogeneous nature of fibroblasts is also demonstrated in mouse models (Rock et al. Proc Natl Acad Sci USA. 2011 Dec. 27; 108(52): E1475-83). A common, long-sought-after, marker for fibroblasts has not been identified because fibroblasts seem to be a heterogeneous cell population (Zeisberg and Kalluri. Am J Physiol Cell Physiol. 2013 Feb. 1; 304(3): C216-25), and the major source of profibrotic fibroblasts has not yet been discovered.

Markers such as α smooth muscle actin (α SMA, encoded by ACTA2 gene, the actin isoform that predominates within smooth-muscle cells and plays an important role in fibrogenesis (Cherng et al. J Am Sci. 2008: 4(4): 7-9)), FSP1/S100A4 (fibroblast-specific protein 1/S100A4-positive protein, a marker of fibroblasts in different organs undergoing tissue remodeling (Osterreicher et al. Proc Natl Acad Sci USA. 2010 Nov. 23; 108(1): 308-13)), Vimentin (a major constituent of the intermediate filament (IF) family of proteins, known to maintain cellular integrity and provide resistant against stress (Satelli & Li. Cell Mol Life Sci. 2011 September; 68(18): 3033-46)), Desmin (a major muscle-specific IF protein essential for structural integrity and muscle function (Paulin & Li. Exp Cell Res. 2004 Nov. 15; 301(1): 1-7)), and PDGFRB (platelet-derived growth factor receptor, beta polypeptide, a tyrosine kinase receptor for members of the PDGF family) are either not exclusively expressed by fibroblasts or specific to all fibroblasts (Krenning et al. J Cell Physiol. 2010 November; 225(3): 631-7; Rock et al., Proc Natl Acad Sci USA. 2011 Dec. 27; 108(52): E1475-83).

It has been suggested that several cellular sources contribute to fibrotic fibroblasts. For example, it has been suggested that circulating fibrocytes or other bone marrow-derived progenitor cells of extrapulmonary origin might be able to migrate to active fibrotic lesions and become fibrotic cells (Andersson-Sjoland et al. Int J Biochem Cell Biol. 2008; 40(10) 2129-40; Hashimoto et al. J Clin Invest. 2004 January; 113(2): 243-52; Phillips et al. J Clin Invest. 2004 August; 114(3): 438-46). Experimental fibrosis models have led to the proposal that epithelial cells (Degryse et al. Am J Physiol Lung Cell Mol Physiol. 2010 October; 299(4): L442-52; Kim et al. Proc Natl Acad Sci USA. 2006 Aug. 29; 103(35): 13180-5; Tanjore et al. Am J Respir Crit Care Med. 2009 Oct. 1: 180(7): 657-65) or endothelial cells (Hashimoto et al. Am J Respir Cell Mol Biol. 2010 August; 43(2): 161-72; LeBleu et al. Nat Med. 2013 August; 19(8): 1047-53; Li and Jimenez. Arthritis Rheum. 2011 August; 63(8): 2473-83) may be able to transform to stromal cells in experimental fibrosis models. However, a genetic tracing approach showed that lung epithelial cells such as Sftpc-lineage AEC2s, as well as Scgb1a1-lineage club cells, do not give rise to fibroblasts (Rock et al. Proc Natl Acad Sci USA. 2011 Dec. 27; 108(52): E1475-83). Genetic fate-mapping methods have confirmed that pericytes proliferate during fibrogenesis, where the pericytes were trace-labeled with either NG2, FoxJ1 or Foxd1 (Hung et al. Am J Respir Crit Care Med. 2013 Oct. 1; 188(7): 820-30 Rock et al. Proc Natl Acad Sci USA. 2011 Dec. 27; 108(52): E1475-83). However, neither these cells nor their progeny express high levels of the myofibroblast marker aSMA: expression of aSMA marks myofibroblasts and smooth muscle cells. Some perivascular Gli1+ cells with distinct characteristics of mesenchymal stem cells (MSCs) can differentiate into myofibroblasts in tissue fibrosis (Kramann et al. Cell Stem Cell. 2015 Jan. 8; 16(1): 51-66).

C. Intrinsic, Autocrine and Epigenetic Mechanisms Regulate Fibrosis

Hyaluronan (HA) is a nonsulfated glycosaminoglycan produced by mesenchymal cells and a variety of tumor cells and has been suggested to contribute to tumor metastasis through interactions with its cognate cell surface receptor CD44 (Arch et al. Science. 1992 Jul. 31; 257(5070): 682-5; Toole, Nat Rev Cancer. 2004 July; 4(7): 528-39). HA is nearly ubiquitous in its distribution, being present in the interstitial spaces of most animal tissues. Accumulation of HA has been shown to be a characteristic of disorders that are associated with progressive tissue fibrosis (Bjermer et al. Thorax. 1989 February; 44(2): 126-31). HA has also been shown to accumulate in the lungs of rats after bleomycin-induced injury, and has a role in regulating the inflammatory response (Jiang et al. Nat Med. 2005 November; 11(11): 1173-9; Noble et al. Physiol Rev. 2011 January; 91(1): 221-64). Three HA synthase genes (HAS1-3) have been identified. Targeted deletion of HAS2 generates an embryonic lethal phenotype caused by impaired cardiac development (Camenisch et al. J Clin Invest. 2000 August; 106(3): 349-60).

CD44 is a ubiquitous cell-surface glycoprotein involved in myriad processes, comprising over 25 signaling super pathways (www.genecards.org/cgi-bin/carddisp.pl?gene=CD44). FIG. 3 illustrates the pathways in which CD44 is involved. CD44 is a major cell surface receptor for HA and plays an important role in inflammatory cell recruitment (Mikecz et al. Nat Med. 1995 June; 1(6): 558-63; Siegelman et al. J Leukoc Biol. 1999 August; 66(2): 315-21) and activation (Nobel et al. J Clin Invest. 1993 June; 91(6): 2368-77; DeGrendele et al. Science. 1997 Oct. 24; 278 (5338): 672-5), as well as tumor growth and metastasis (Lesley et al. Adv Immunol. 1993; 54: 271-335). CD44 is necessary for hematopoietic cells to clear HA from sites of inflammation (Teder et al. Science. 2002 Apr. 5; 296(5565: 155-8), and is critical for the recruitment of fibroblasts to the injury sites (Acharya et al., J Cell Sci. 2008 May 1; 121 (Pt 9): 1393-402.).

The inexorable course of progressive fibrosis in IPF has led to the theory that fibroblasts may take on properties similar to metastatic cancer cells that overexpress HA. Consistent with this concept is a recent study showing that IPF fibroblasts have abnormalities in translational control (Larsson et al. PLoS One. 2008 Sep. 16; 3(9): e3220) that can be found in cancer cells. One of the seminal properties of metastatic cancer cells is the ability to invade basement membrane. It has been suggested that fibrotic fibroblasts and myofibroblasts drive fibrogenesis by invasion and destruction of basement membrane and that HA-CD44 interactions may regulate this process.

Mechanical modifications to the ECM and cell-intrinsic changes in fibroblasts and epithelial cells have been shown to contribute to the progression of fibrosis by maintaining the activation of the following fibrogenic pathways (Wynn & Ramalingam. Nat Med. 2012 Jul. 6; 18(7): 1028-40).

1. The Wnt-β-Catenin Signaling Pathway

The Wnt-β-catenin signaling pathway is constitutively activated in AEC2s in mouse models of pulmonary fibrosis and in patients diagnosed with IPF and chronic obstructive pulmonary disease (Baarsma et al. PLoS One. 2011; 6(9): e25450). The Wnt-β-catenin signaling pathway is illustrated in FIG. 4. This ubiquitous pathway is involved in organ development, tissue homeostasis, cell growth, renewal, and regeneration, is intimately involved in tumorigenesis (Valenta et al. EMBO J. 2012 Jun. 13; 31(12): 2714-36). Wnt-1 is involved in over 30 signaling super pathways, and β-catenin is involved in nearly 100 signaling super pathways (www.genecards.org/cgi-bin/carddisp.pl?gene=WNT1; www.genecards.org/cgi-bin/carddisp.pl?gene=CTNNB1)

Mechanistically, Wnt-1-inducible signaling protein 1 (WISP-1) has been shown in mice to increase the proliferation of AEC2s, and promote EMT in the lung (Wynn & Ramalingam. Nat Med. 2012 Jul. 6; 18(7): 1028-40). WISP-1 also increases the synthesis of ECM components in mouse and human lung fibroblasts (Jiang et al. J Hepatol. 2006 September; 45(3): 401-9). Blocking studies demonstrated that bleomycin-induced pulmonary fibrosis is highly dependent on the Wnt-1 pathway (Konigshoff et al. J Clin Invest. 2009 April; 119(4): 772-87).

As tissues become more fibrotic, the increased tissue stiffness and decreased elasticity result in mechanical stress, which has been shown to exacerbate tissue injury and perpetuate the activation of local fibroblasts expressing α-smooth muscle actin (α-SMA) (Hinz et al. Mol Biol Cell. 2001 September; 12(9): 2730-41). Two in vitro studies in mouse and porcine cells have suggested that mechanical stress contributes to aberrant wound healing and fibrosis by inducing EMT in AEC2s via a mechanism driven by TGF-β1, Wnt-3-catenin and hyaluronan (Heise et al. J Biol Chem. 2011 May 20; 286(20): 17435-44; Chen et al. Arterioscler Thromb Vasc Biol. 2011 March; 31(3): 590-7). Fibroblasts that are activated as a result of increased tissue or substrate stiffness also seem to maintain their activated phenotype when returned to healthy 'soft' tissues (Balestrini et al. Integr Biol (Camb). 2012 April; 4(4): 410-21), suggesting that mechanical sensing by fibroblasts can permanently alter their behavior in favor of a fibrotic phenotype. It has been suggested that the differentiation of fibroblasts into ECM-producing myofibroblasts is controlled by the combined actions of IL-1, TGF-β1 and mechanical tension (Hinz. Curr Rheumatol Rep. 2009 April; 11(2): 120-6). Increased compression, shear forces and hydrostatic pressures associated with portal hypertension and vascular remodeling can also perpetuate myofibroblast activation (Wynn & Ramalingam. Nat Med. 2012 Jul. 6; 18(7): 1028-40).

Biomarkers in IPF

Researchers have made efforts to identify diagnostic and predictive biomarkers to improve the drug development in IPF, especially in view of the devastating effects and lethality of IPF and its unknown origin (Zhang & Kaminski. Curr Opin Pulm Med. 2012 September; 18(5): 441-6).

A. Diagnostic Biomarkers

In the context of peripheral blood markers, multiple molecules have been shown to distinguish patients with IPF from controls. These include KL-6 (a high molecular weight glycoprotein used as a serum marker for interstitial lung diseases (Yokoyama et al. Respirology. 2006 March; 11(2): 164-8), surfactant proteins SP-A and SP-D (collagenous glycoproteins investigated at biomarkerse for IPF (Greene et al. ur Respir J. 2002 March; 19(3): 439-46)), matrix metalloproteases MMP-1 and MMP-7 (interstitial collagenases investigated as biomarkers for IPF (Rosas et al. PLoS Med. 2008 Apr. 29; 5(4): e93)). SPP1 (glycoprotein observed to be upregulated in human IPF (Pardo et al. PLoS Med. 2005 September; 2(9): e251)) and YKL-40 (a mammalian chitinase-like protein observed to be upregulated in IPF (Furuhashi et al. Respir Med. 2010 August; 104(8): 1204-10). However, the diagnostic utility of any of these molecules is in doubt as the majority of the studies usually only compared IPF to control individuals, and when smoking controls or other interstitial lung diseases ("ILDs") were analyzed, they often had increased levels of the markers (Zhang & Kaminski. Curr Opin Pulm Med. 2012 September; 18(5): 441-6).

B. Disease Susceptibility Biomarkers

Multiple mutations associated with familial and sporadic forms of IPF have been reported including mutations in surfactant (Thomas et al. Am J. Respir Crit Care Med. 2002 May 1; 165(9): 1322-8; Lawson et al. Thorax. 2004 November; 59(11): 977-80; Wang et al. Am J Hum Genet. 2009 January; 84(1): 52-9) and telomerase proteins (Armanios et al. N Engl J Med. 2007 Mar. 29; 356(13): 1317-26; Tsakiri et al. Proc Natl Acad Sci USA. 2007 May 1; 104(18): 7552-7). Polymorphisms within TERT (telomerase reverse transcriptase) have also been identified [single nucleotide polymorphism (SNP) in intron 2 of the TERT gene—rs2736100] in a genome-wide association (GWA) study including a derivation cohort of 159 sporadic IPF patients and 934 controls as well as a replication cohort of 83 sporadic IPF cases and 535 controls (Mushiroda et al. J Med Genet. 2008 October; 45(10): 654-6). Leukocyte telomere shortening was found in 24% of familial pulmonary fibrosis and 23% of sporadic IPF cases when compared to control individuals (P=2.6×10-8) (Cronkhite et al. Am J Respir Crit Care med. 2008 Oct. 1; 178(7): 729-37) in a study that contained 201 control individuals, 59 probands with familial pulmonary fibrosis and 73 sporadic pulmonary fibrosis cases without TERT or TERC (telomerase RNA component) mutations. Other genetic variants have been described in IPF, including genes encoding ELMOD2 (a GPTase-activating protein (Hodgson et al. Am J Hun Genet. 2006 July; 79(1): 149-54)), IL-1 (cytokine involved in immune and inflammatory responses (Hutyrova et al. Am j Respir Crit Care Med. 2002 Jan. 15; 165(2): 148-51)), CR-1 (complement receptor 1, a transmembrane glycoprotein, (Zorzetto et al. Am J Respir Crit Care Med. 2003 Aug. 1; 168(3): 330-4)), IL12p40 and IFN-γ (IL-12 p40 subunit and IFN-γ (Latsi et al. Respir Res. 2003. 4:6)), NOD2/CARD15 (an intracellular innate immune sensor (Zorzetto et al. Sarcoidosis Vasc Diffuse Lung Dis. 2005 October; 22(3): 180-5)), MMP-1 (matrix metalloproteinase-1 (ENA-78, epithelial neutrophil activating peptide 78; VEGF, vascular endothelial growth factor; IP-10, interferon-inducible protein 10 (Checa et al. Hum Genet. 2008 December; 124(5): 465-72)), ENA-78, IP-10 and VEGF (Liu et al. Zhonghua Yi Xue Za Zhi. 2009 Oct. 20; 89(38): 2690-4)), CD16b (Fcγ receptor IIIb (Bournazos et al. Lung. 2010 December; 188(6): 475-81)), IL-8 (interleukin 8 (Ahn et al. Respir Res. 2011 Jun. 8; 12:73)) and HER2 (human epidermal growth factor receptor 2 (Martinelli et al. Mol Biol Rep. 2011 October; 38(7): 4613-7)), but the majority have not been replicated. Recently, a SNP in the putative promoter of MUC5B (rs35705950) that was associated with familial interstitial pneumonia (minor allele frequency of 34%, $P=1.2\times10^{-5}$) and IPF (minor allele frequency of 38%, P=2.5×10-37) has been identified; in controls, the minor allele frequency was 9% (Seibold et al. N Engl J Med. 2011 Apr. 21; 364(16): 1503-12). The odds ratio was 6.2 [95% confidence interval (CI) 3.7-10.4] for familial interstitial pneumonia and 8.3 (95% CI 5.8-11.9) for IPF (Id.). These findings were simultaneously confirmed by other researchers in an independent case-control study that included 341 IPF and 801 control individuals (Zhang et al. N Engl J Med. 2011 Apr. 21; 364(16): 1576-7). The minor-allele frequency was 34.3% in patients with IPF and 11.1% in controls (allelic association, P=7.6×10-40). (Id.).

C. Prognostic Biomarkers

High blood concentrations of KL-6, also known as MUC-1, repeatedly have been repeatedly shown to be predictive of decreased survival in IPF (Zhang & Kaminski. Curr Opin Pulm Med. 2012 September; 18(5): 441-6). Most studies have been limited by cohort size and lack replication, but are still highly consistent and support the use of KL-6 in disease stratification (Ishikawa et al. Respir Investig. 2012 March; 50(1): 3-13. Other studies have shown that serum CCL18 (chemokine (C-C motif) ligand 18) levels were able to predict the outcomes in IPF (higher serum CCL18 concentrations were predictive of decreased total lung capacity, decreased forced vital capacity and increased mortality (Prasse et al. Am J Respir Crit Care Med. 2009 Apr. 15; 179(8): 717-23)), that high serum SP-A concentrations was a predictor of early mortality in IPF (Kinder et al. Chest. 2009 June; 135(6): 1557-63), and that high serum concentrations of YKL-40 distinguished two groups with distinct survival patterns with the hazard ratio for serum YKL-40 (cut-off 79 ng/ml) as 10.9 (95% CI 1.9-63.8, P<0.01) (Korthagen et al. Respir Med. 2011 January; 105(1): 106-13). Researchers using a targeted proteomic approach screened 95 proteins in the plasma of 140 IPF patients (derivation cohort) and validated the results in a replication cohort (101 patients) (Richards et al. Am J Respir Crit Care Med. 2012 Jan. 1; 185(1): 67-76). High plasma concentrations of MMP-7, ICAM-1 and IL-8 were predictive of poor overall survival in both cohorts (Id.). The derivation cohort was used to derive a personal clinical and molecular mortality prediction index (PCMI) using the step AIC approach (Venables & Ripley. Modern applied statistics with S. New York: Springer; 2002). This index [PCMI=114×I(Male)+2×(100%−FVC % predicted)+3×(100%−DIco % predicted)+111×I(MMP-7≥4.3 ng/ml)] was highly predictive of mortality in the replication cohort with a C-index for early mortality of 84 (Richards et al. Am J Respir Crit Care Med. 2012 Jan. 1; 185(1): 67-76).

Similarly, changes in circulating blood cell populations have been associated with outcome. Recent studies have demonstrated in a cohort of 51 patients that increases in circulating fibrocytes predicted poor prognosis (Moeller et al. Am J Respir Crit Care Med. 2009 Apr. 1; 179(7): 588-94) and other researchers have observed that downregulation of CD28 in circulating CD4 T cells was a marker of poor prognoses in a cohort of 89 IPF patients (Gilani et al. PLoS One. 2010 Jan. 29; 5(1): e8959.

D. Disease Activity Markers

There is no real definition of the disease activity of IPF. It is conceivable that KL-6, SP-A and MMP-7 are markers of alveolar epithelial cell injury and CCL-18 a marker of alveolar macrophage activation; however, at the present, markers for some of the processes that happen in IPF such as deposition of excess collagen have not yet been discovered. Mechanistically, the biomarker that may be tied most closely to disease pathogenesis is MMP-7, a pluripotent matrix metalloprotease expressed in alveolar type II cells. MMP-7 is a WNT/0-catenin pathway target molecule (He et al. J Am Soc Nephrol. 2012 February; 23(2): 294-304), suggesting that increases of MMP-7 are reflective of aberrant WNT/P catenin that has been described in IPF (Chilosi et al. Am J Pathol. 2003 May; 162(5): 1495-502; Konigshoff et al. J Clin Invest. 2009 April; 119(4): 772-87). MMP-7 knockout mice are relatively protected from bleomycin-induced fibrosis, suggesting that it is mechanistically involved in the fibrosis pathways (Zuo et al. Proc Natl Acad Sci USA. 2002 Apr. 30; 99(9): 6292-7). However, at present, there is no data to support MMP-7 as a marker of disease activity (Id.).

Acute exacerbations of IPF (AE-IPF) are episodes of decline in respiratory status without an identifiable cause (Collard et al. Am J Respir Crit Care Med. 2007 Oct. 1; 176(7): 636-43), that lead to significant mortality (Song et al. Eur Respir J. February; 37(2): 356-63). Of the previous markers mentioned, KL-6 has been mostly widely studied in this context (Ishikawa et al. Respir Investig. 2012 March; 50(1): 3-13; Collard et al. Am J Physiol Lung Cell Mol Physiol. 2010 July; 299(1): L3-7; Satoh et al. J Intern Med. 2006 November; 260(5): 429-34). It appears that AE-IPF are associated with increases in blood KL-6, although the mechanisms have not yet been elucidated. Comparisons of gene expression in the lungs of patients with AE-IPF lungs to stable IPF (Konishi et al. Am J Respir Crit Care med. 2009 Jul. 15; 180(2): 167-75) has identified 579 differentially expressed genes, and did not find any indication of infectious or inflammatory cause. Researchers have found increases in α-defensins, a group of innate antimicrobial peptides, in the mRNA levels as well as in the plasma protein level of AE-IPF patients, suggesting that they should be evaluated as biomarkers for acute exacerbations (Zasloff. Nature. 2002 Jan. 24; 415(6870): 389-95).

E. Drug Efficacy Biomarkers

There are no drug efficacy biomarkers in IPF (Zhang & Kaminski. Curr Opin Pulm Med. 2012 September; 18(5): 441-6).

Utility and Limitations of Animal Models in the Study of IPF

Bleomycin, a chemotherapeutic agent used in the treatment of certain human cancers, has been the most commonly used agent to induce pulmonary fibrosis in animal models of the disease. Bleomycin can be administered through a variety of routes including intratracheal (most common), intraperitoneal, oropharyngeal aspiration, and via osmotic pump. It induces DNA strand breaks (Lown & Sim. Biochem Biophys Res Commun. 1977 Aug. 22; 77(4): 1150-7) and oxidative injury (Sausville et al. Biochem Biophys Res Commun. 1976 Dec. 6; 73(3): 814-22), thus leading to epithelial injury, inflammation, and ultimately fibrosis (Barkauskas & Noble. Am J Physiol Cell Physiol. 2014 Jun. 1; 306(11): C987-96).

The bleomycin model is well-documented and the best characterized murine model in use today to demonstrate efficacy of a particular drug or protein kinase inhibitor in the post-inflammatory/pre-fibrotic/fibro-preventive stages (Vittal, R. et al., J Pharmacol Exp Ther., 321(1):35-44, 2007; Vittal, R. et al., Am J Pathol., 166(2):367-75, 2005; Hecker L. et al., Nat Med., 15(9):1077-81, 2009).

The antibiotic bleomycin was originally isolated from *Streptomyces verticillatus* (Umezawa, H. et al., Cancer 20: 891-895, 1967). This antibiotic was subsequently found to be effective against squamous cell carcinomas and skin tumors (Umezawa, H., Fed Proc, 33: 2296-2302, 1974); however, its usefulness as an anti-neoplastic agent was limited by dose-dependent pulmonary toxicity resulting in fibrosis (Muggia, F. et al., Cancer Treat Rev, 10: 221-243, 1983). The delivery of bleomycin via the intratracheal route (generally 1.25-4 U/kg, depending on the source) has the advantage that a single injection of the drug produces lung injury and resultant fibrosis in rodents (Phan, S. et al., Am Rev Respir Dis 121: 501-506, 1980; Snider, G. et al., Am Rev Respir Dis. 117: 289-297, 1978; Thrall, R. et al., Am J Pathol, 95: 117-130, 1979). Intratracheal delivery of the drug to rodents results in direct damage initially to alveolar epithelial cells. This event is followed by the development of neutrophilic and lymphocytic pan-alveolitis within the first week (Janick-Buckner, D. et al., Toxicol Appl Pharmacol., 100(3):465-73, 1989). Subsequently, alveolar inflammatory cells are cleared, fibroblast proliferation is noted, and extracellular matrix is synthesized (Schrier D. et al., Am Rev Respir Dis., 127(1):63-6, 1983). The development of fibrosis in this model can be seen biochemically and histologically by day 14 with maximal responses generally noted around days 21-28 (Izbicki G. et al., Int J Exp Pathol., 83(3):111-9, 2002; Phan, S. et al., Chest., 83(5 Suppl):44S-45S, 1983). Beyond 28 days, however, the response to bleomycin is more variable. Original reports suggest that bleomycin delivered intratracheally may induce fibrosis that progresses or persists for 60-90 days (Thrall R. et al., Am J Pathol., 95(1):117-30, 1979; Goldstein R., et al., Am Rev Respir Dis., 120(1):67-73, 1979; Starcher B. et al., Am Rev Respir Dis., 117(2):299-305, 1978); however, other reports demonstrate a self-limiting response that begins to resolve after this period (Thrall R. et al., Am J Pathol., 95(1):117-30, 1979; Phan, S. et al., Chest, 83(5 Suppl): 44S-45S, 1983; Lawson W. et al., Am J Pathol. 2005; 167(5):1267-1277). While the resolving nature of this model does not mimic human disease, this aspect of the model offers an opportunity for studying fibrotic resolution at these later time points.

The pathology generated by intratracheal bleomycin is not fully representative of IPF histology. The diagnostic criteria for IPF (usual interstitial pneumonia) are threefold: 1) nonuniform pattern of disease involvement with normal lung interspersed with diseased lung, 2) architectural distortion (honeycomb change and/or scar), and 3) presence of fibroblast foci, presumed to be indicative of current ongoing disease. These structures are covered by hyperplastic AEC2s (Katzenstein et al. Hum Pathol. 2008 September; 39(9): 1275-94). While not a diagnostic criterion, human IPF specimens also typically include areas of alveolar collapse with incorporation of basal lamina (Myers & Katzenstein. Chest. 1988 December; 94(6): 1309-11). While experimental bleomycin fibrosis can recapitulate alveolar collapse and cystic air spaces 14 days after intratracheal instillation (Moore et al. Am J Respir Cell Mol Biol), it is also typically characterized by significant neutrophilic inflammation and there rarely exist examples of the hyperplastic AEC2s that are pathognomonic for the human disease (Degryse et al. Am J Physiol Lung Cell Mol Physiol. 2010 October; 299(4): L442-52; Moore et al. Am J Respir Cell Mol Biol. 2013 August; 49(2): 167-79; Barkauskas & Noble. Am J Physiol Cell Physiol. 2014 Jun. 1; 306(11): C987-96).

Unlike IPF, however, the fibrosis generated after intratracheal bleomycin is not progressive. Following intratracheal bleomycin, collagen content (as assessed by hydroxyproline assay) peaks around 21-28 days postinjury (Izbicki et al. Int J Exp Pathol. 2002 June; 83(3): 111-9). Recent reports and our own personal experience with this model suggest that the fibrosis induced by a single exposure to bleomycin is self-limited and can display some resolution/regression during the weeks following the injury (Chung et al. Am J Respir Cell Mol Biol. 2003 September; 29(3 Pt 1): 375-80; Lawson et al. Am J Pathol. 2005 November; 167(5): 1267-77; Rock et al. Proc Natl Acad Sci USA. 2011 Dec. 27; 108(52): E1475-83; Barkauskas & Noble. Am J Physiol Cell Physiol. 2014 Jun. 1; 306(11): C987-96).

Investigators have tried to optimize the bleomycin fibrosis model to better replicate the histology associated with human IPF. In one such study, a repetitive bleomycin model was developed in an attempt to recapitulate the recurrent alveolar injury that is hypothesized to drive IPF pathogenesis. Degryse et al. (Am J Physiol Lung Cell Mol Physiol. 2010 October; 299(4): L442-52) describe a model in which they administered intratracheal bleomycin biweekly up to eight times. The histology from this repetitive injury model revealed prominent hyperplastic AEC2s in areas of fibrosis as well as more of a temporally heterogeneous pattern of lung injury (i.e., fibrotic scar next to hyperplastic AEC2s next to normal tissue). Further, the fibrosis that developed seemed to persist until at least 10 weeks after the last bleomycin dose. While the histological results of this model do seem more consistent with human IPF, the time-intensive nature of this model may limit its applicability in the laboratory (Barkauskas & Noble. Am J Physiol Cell Physiol. 2014 Jun. 1; 306(11): C987-96).

Despite its imperfections, the bleomycin model of pulmonary fibrosis remains the most common in the study of fibrotic lung disease. Other fibrosis generating models include the following (reviewed in Moore et al. Am J Physiol Lung Cell Mol Physiol. 2008 February; 294(2): L152-60): granulomatous inflammation (Jakubzick et al Am J Pathol. 2003 May; 162(5): 1475-86), fluorescein isocyanate (Kolodsick et al. J Immunol. 2004 Apr. 1; 172(7): 4068-76; Roberts et al. J Pathol. 1995 July; 176(3): 309-18), irradiation-induced (McDonald et al. Radiother Oncol. 1993 March; 26(3): 212-8), adenosine deaminase deficiency (Chunn et al. Am J Physiol Lung Cell Mol Physiol. 2006 March; 290(3): L579-87), and murine gamma-herpesvirus (which is typically used to augment a fibrotic response to another stimulus) (Gangadharan et al. J Leukoc Biol. 2008 July; 84(1): 50-8; Lok et al. Eur Respir J. 2002 November; 20(5): 1228-32). While many investigators are now designing experiments with human IPF tissue/cells, the field at large still relies heavily on murine models of the disease. A murine model of IPF that recapitulates the disease more faithfully than bleomycin would be most welcome (Barkauskas & Noble. Am J Physiol Cell Physiol. 2014 Jun. 1; 306(11): C987-96).

To date, only limited treatments or therapies exist for the treatment of IPF, and there is a substantial unmet need for effective treatments that can alter the course of IPF by slowing or reversing disease progression. Many clinical trials have ended unsuccessfully after showing negligible patient benefit or high incidence of side effects.

The described invention involves novel methods to target fibroblast invasion as a way to screen therapeutics for patients with progressive pulmonary fibrosis, such as IPF, and has several advantages including: 1. the screening is targeted to a small group of cells which have been proved to be important in fibrogenesis in vitro in human disease and in mouse models in vivo; 2. the hits generated from this screening will have a minimal impact to the majority of fibroblasts; and 3. this screening strategy would lead to drugs with no or minimal side effect.

SUMMARY OF THE INVENTION

According to one aspect, the described invention provides a method for identifying a therapeutic compound effective to reduce invasiveness of fibroblasts characterized by a highly invasive phenotype obtained from a subject with idiopathic pulmonary fibrosis, comprising (a) purifying a population of the fibroblasts characterized by a highly invasive phenotype by: (i) confirming expression of cell surface markers Krtap2-3$^{high}$ and Patched1$^{negative}$ by the invasive fibroblasts by flow cytometry; (ii) isolating and establishing single cell clones based on expression of the cell surface markers; (iii) Transfecting into IPF fibroblasts one or more mammalian expression pcDNA3-XFP vectors selected from the group of Krtap23-GFP, PODXL-RFP, CD127-CFP and PTCH1-mCherry comprising a promoter of Krtap23, PODXL, CD127, or Patched1 inserted upstream of the fluorescent protein tag; (iv) selecting positive cells of XFP expression; and (v) determining cell marker expression, matrix production, proliferation, survival, migration and invasive capacity of the transfected cells, (b) contacting the population of fibroblasts characterized by the highly invasive phenotype with a prospective therapeutic compound; and (c) reducing invasiveness of the fibroblasts as measured in an invasiveness assay, with minimal impact on normal lung fibroblasts with a non-invasive phenotype. According to one embodiment of the method, the highly invasive phenotype comprises differential expression of one or more of genes Krtap2-3, Involucrin, PODXL, IL7R. GPNMB, VAMP1, Patched1. According to another embodiment, transcriptional control of the invasive phenotype comprises upregulation of one or more transcriptional factors selected from TAF12, MGA2, and BNC1 and downregulation of one or more transcriptional factors selected from NR4A2 and NEAT1. According to another embodiment, the therapeutic compound is a short hairpin RNA.

BRIEF DESCRIPTION OF THE DRAWINGS

The patent or patent application file contains at least one drawing executed in color. Copies of this patent or patent application publication with color drawing(s) will be provided by the Office upon request and payment of the necessary fee.

DETAILED DESCRIPTION OF THE INVENTION

Glossary

Figure 1:
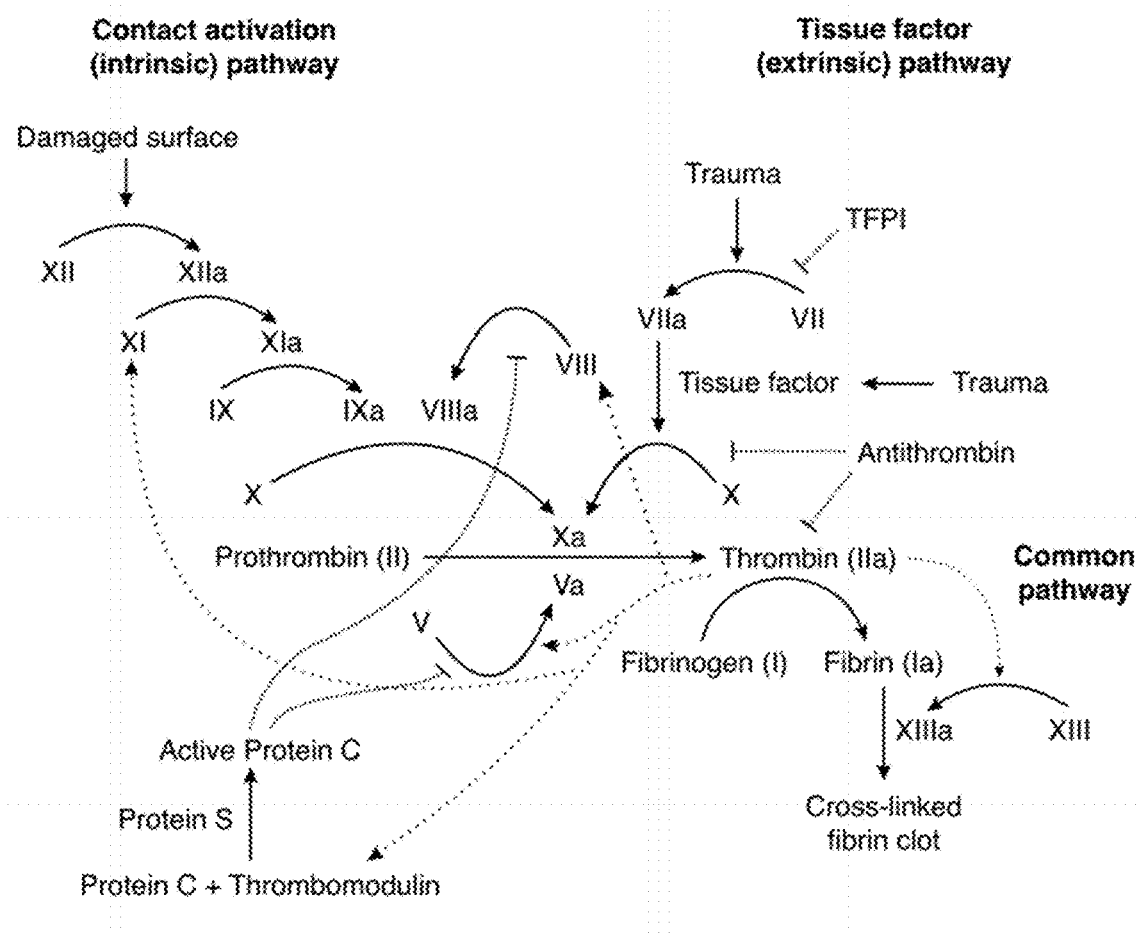
FIG. 1 shows the contact activation (intrinsic) and the tissue factor (extrinsic) coagulation pathways.
Figure 2:
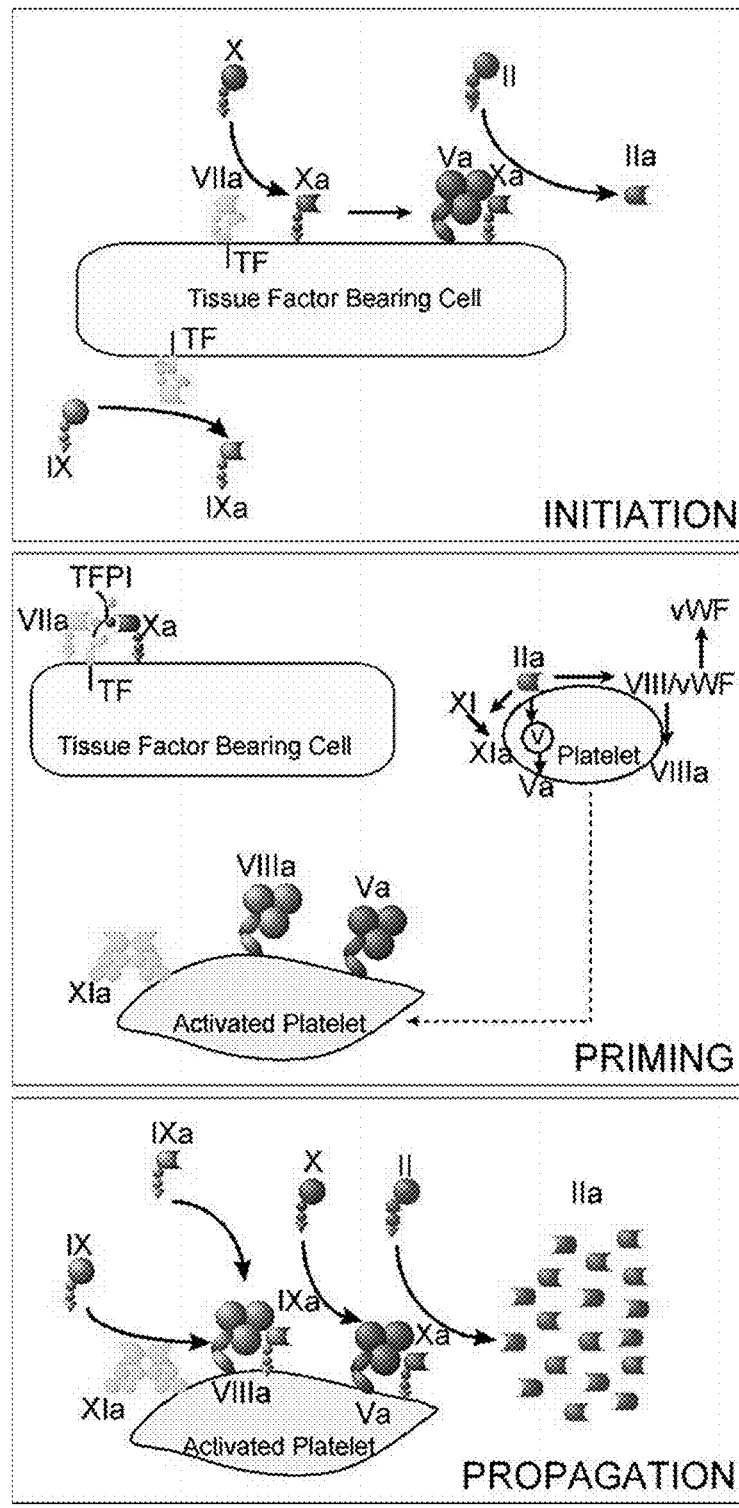
FIG. 2 shows a three stage cell-surface based model of coagulation, comprising initiation, priming, and propagation (Monroe et al. Arterioscler Thromb Vasc Biol. 2002 Sep. 1; 22:1381-1389).
Figure 3:
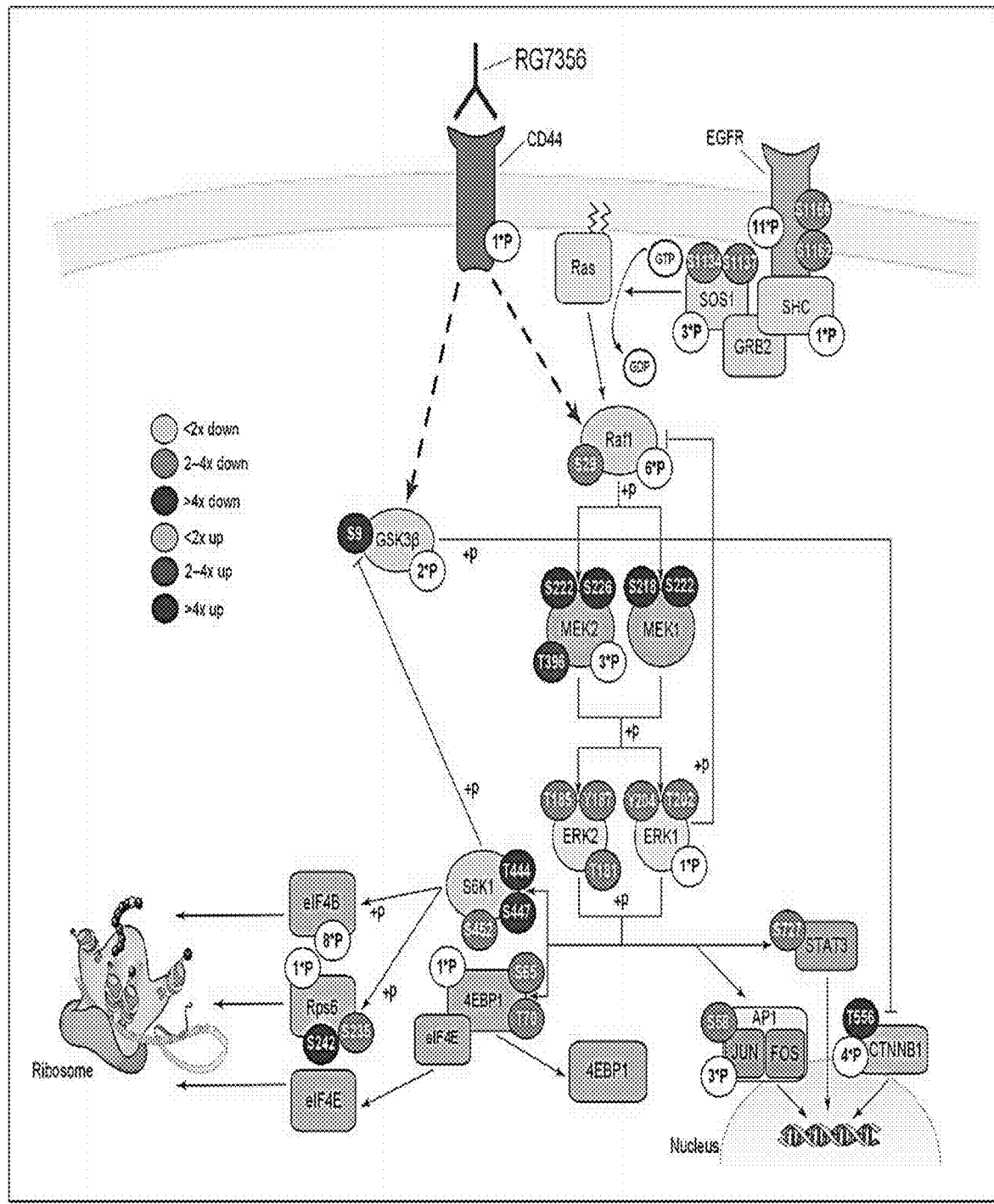
FIG. 3 depicts the role of CD44 in various pathways (Wiegand et al. Cancer Res. 2012 September; 72(17): 4329-39).
Figure 4:
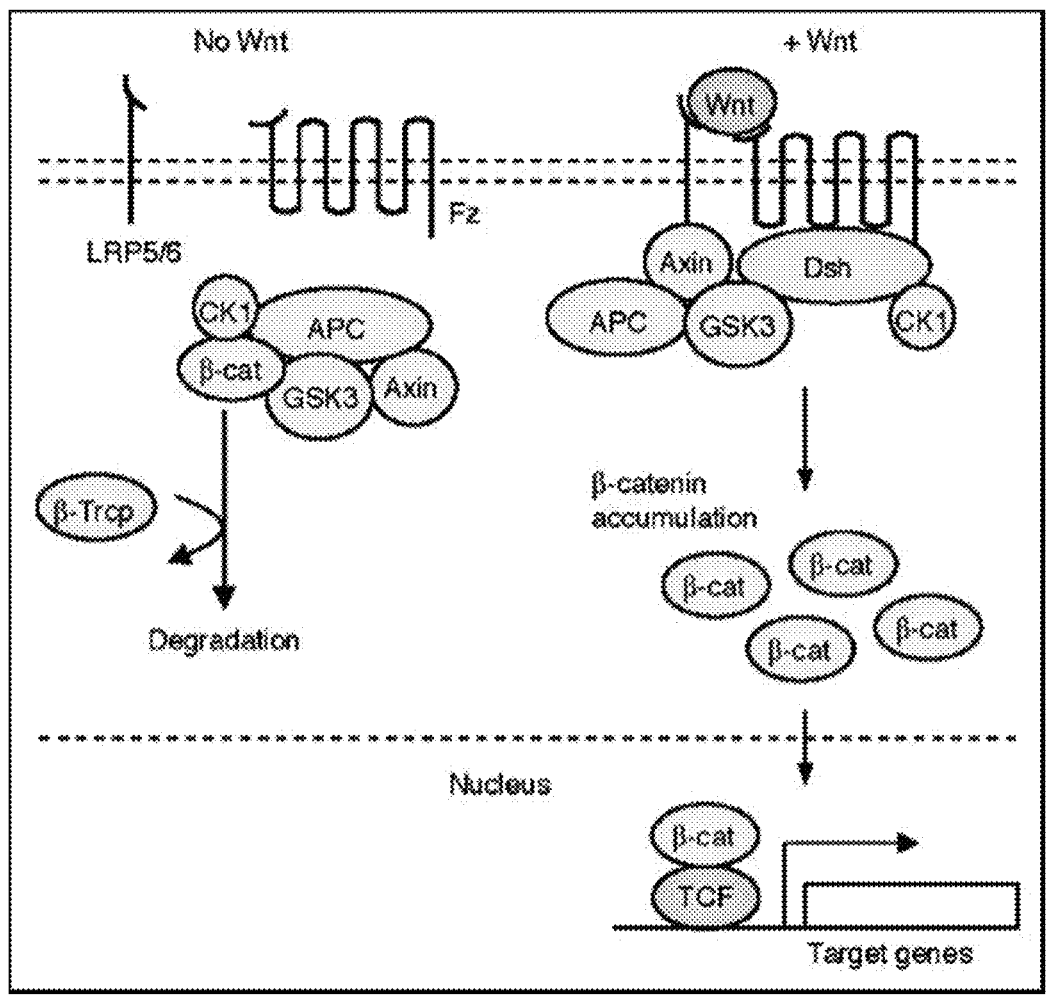
FIG. 4 depicts the canonical Wnt-β-catenin signal transduction cascade (Komiya & Habas. Organogenesis. 2008 April-June; 4(2): 68-75).

Anatomical Terms:

When referring to animals, that typically have one end with a head and mouth, with the opposite end often having the anus and tail, the head end is referred to as the cranial end, while the tail end is referred to as the caudal end. Within the head itself, rostral refers to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. On the limbs or other appendages, a point closer to the main body is "proximal"; a point farther away is "distal". Three basic reference planes are used in zoological anatomy. A "sagittal" plane divides the body into left and right portions. The "midsagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions.

When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is an Y-Z plane, perpendicular to the ground, which separates the anterior from the posterior. A sagittal plane is an X-Z plane, perpendicular to the ground and to the coronal plane, which separates left from right. The midsagittal plane is the specific sagittal plane that is exactly in the middle of the body.

Structures near the midline are called medial and those near the sides of animals are called lateral. Therefore, medial structures are closer to the midsagittal plane, lateral structures are further from the midsagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

The term "Bayes factor" as used herein refers to a likelihood ratio used as a measure of evidential strength, in lieu of classical hypothesis testing parameters, such as P-values (i.e., calculated probability, the estimated probability of rejecting the null hypothesis (H0) of a study question when that hypothesis is true). The Bayes factor is illustrated in the following equation:

$$\text{Bayes factor, } K = \frac{Prob \text{ (Data, given the null hypothesis)}}{Prob \text{ (Data, given the alternate hypothesis)}}$$

A Bayes Factor, K, of >1 indicates that the null hypothesis is more strongly supported by the data u The term "biomarkers" as used herein refers to are molecules or genes that carry information about the health or disease state of the individual. Generally speaking, biomarkers can be divided into several classes based on the type of the information that they provide. Diagnostic biomarkers allow the distinction of one disease from the other, and can be used in disease classification and diagnosis. Disease susceptibility markers—most often gene mutations and polymorphisms associated with the disease—are often included with diagnostic markers, but in fact differ because in the healthy individual they just indicate an increased risk and their diagnostic value is unclear in complex disease. Prognostic biomarkers are markers that allow the prediction of outcome, usually at the time of presentation. Diagnostic and prognostic markers should be distinguished from disease activity biomarkers that may change during the course of the disease—although in some cases they may overlap. The last group of biomarkers can be broadly defined as treatment efficacy biomarkers—these include markers that a drug is indeed affecting the pathway it is supposed to affect, markers that indicate toxicity and markers that indicate a real beneficial drug effect that could eventually be used as surrogate endpoints in drug studies (Zhang & Kaminski. Curr Opin Pulm Med. 2012 September; 18(5): 441-6).

The term "BNC1" as used herein refers to the gene that encodes zinc finger protein basonuclin 1. It is likely to be a transcription factor specific for squamous epithelium and for constituent keratinocytes at a stage either prior to or at the very beginning of terminal differentiation.

The term "cell line" as used herein refers to a population of cultured cells that has undergone a change allowing the cells to grow indefinitely.

The term "cell strain" as used herein refers to a population of cultured cells that has a finite life span.

The term "CFP" as used herein refers to cyan fluorescent protein, which possesses bright fluorescence with excitation/emission maxima at 458 and 480 nm, respectively.

The term "complementary" as used herein refers to two nucleic acid sequences or strands that can form a perfect base-paired double helix with each other.

The term "downstream" with respect to a gene, refers to the direction RNA polymerase moves during transcription, which is toward the end of the template DNA strand with a 3' hydroxyl group. The term "upstream" is the direction on a DNA opposite to the direction RNA polymerase moves during transcription.

The term "EGFP" as used herein refers to enhanced green fluorescent protein, a protein composed of 238 amino acid residues (26.9 kDa) that exhibits bright green fluorescence when exposed to light in the blue to ultraviolet range.

The term "expression vector" as used herein refers to a modified DNA molecule that carries a gene or DNA which is specially constructed into a suitable host cell and there directs synthesis of a protein product encoded by an inserted sequence.

The term "fibroblast" as used herein refers to a connective tissue cell that secretes collagen and other components of the extracellular matrix, which migrates and proliferates during normal wound healing.

The term "flow cytometry" as used herein refers to a tool for interrogating the phenotype and characteristics of cells. Flow cytometry is a system for sensing cells or particles as they move in a liquid stream through a laser (light amplification by stimulated emission of radiation)/light beam past a sensing area. The relative light-scattering and color-discriminated fluorescence of the microscopic particles is measured. Analysis and differentiation of the cells is based on size, granularity, and whether the cells is carrying fluorescent molecules in the form of either antibodies or dyes. As the cell passes through the laser beam, light is scattered in all directions, and the light scattered in the forward direction at low angles (0.5-10 degrees) from the axis is proportional to the square of the radius of a sphere and so to the size of the cell or particle. Light may enter the cell; thus, the 90 degree light (right-angled, side) scatter may be labeled with fluorochrome-linked antibodies or stained with fluorescent membrane, cytoplasmic, or nuclear dyes. Thus, the differentiation of cell types, the presence of membrane receptors and antigens, membrane potential, pH, enzyme activity, and DNA content may be facilitated. Flow cytometers are multiparameter, recording several measurements on each cell; therefore, it is possible to identify a homogeneous subpopulation within a heterogeneous population (Marion G. Macey, Flow cytometry: principles and applications, Humana Press, 2007).

The term "GATHER" as used herein, refers to a tool that integrates various forms of available data to elucidate biological context within molecular signatures produced from high-throughput post-genomic assays. GATHER is an acronym for a "Gene Annotation Tool to Help Explain Relationships," and has been noted for its: 1) ability to discover novel functions of gene groups by integrating functional descriptors from evolutionary homologs and other genes related through protein interaction; 2) ability to annotate, or designate functional descriptors to genes with respect to datasets from multiple systems; and 3) use of a Bayesian statistical model to increase the accuracy of its findings (Chang & Nevins. Bioinformatics. 2006; 22(23): 2926-33). GATHER is available at http://gather.genome.duke.edu).

The term "gene" as used herein is the entire DNA sequence, including exons, introns, and noncoding transcription-control regions necessary for production of a functional protein or RNA.

The term "gene expression" or "expression" are used interchangeably to refer to the process by which information encoded in a gene is converted into an observable phenotype.

The term "growth" as used herein refers to a process of becoming larger, longer or more numerous, or an increase in size, number, or volume.

The term "interfere" or "to interfere with" as used herein refers to the hampering, impeding, dampening, hindering, obstructing, blocking, reducing or preventing of an action or occurrence.

The term "invasion" or "invasiveness" as used herein refers to a process that includes penetration of and movement through surrounding tissues.

The term "GPNMB" as used herein refers to the gene encoding glycoprotein nonmetastatic melanoma protein B. It is up-regulated in various cancer cells, including in glioblastoma multiforme; and expressed in many melanoma cells, as well as in tissue macrophages, including liver Kuppfer cells and lung alveolar macrophages, in podocytes and in some cells of the ciliary body of the eye (at protein level). Waterman, M A J, et al, Intl. J. Cancer 60: 73-81 (1995); Kuan, C T et al, Clin. Cancer Res. 12: 1970-82 (2006) Hardly detectable in healthy brain.

The term "HMGA2" as used herein refers to the gene that encodes high mobility group protein HMGI-C, which functions as a transcriptional regulator. It functions in cell cycle regulation through the gene CCNA2, which encodes cyclin-A2, and plays a role in chromosome condensation during the meiotic G2/M transition of spermatocytes. Tesari, M. A., Mol. Cell Biol. 23: 9104-9116 (2003).

The term "homeobox genes" as used herein refers to a large family of similar genes that direct the formation of many body structures during early embryonic development. In humans, the homeobox gene family contains an estimated 235 functional genes and 65 pseudogenes (meaning structurally similar genes that do not provide instructions for making proteins). Homeobox genes are present on every human chromosome, and often appear in clusters. Homeobox genes contain a particular DNA sequence that provides instructions for making a string of 60 amino acids known as the homeodomain. Most homeodomain-containing proteins act as transcription factors. The homeodomain is the part of the protein that attaches (binds) to specific regulatory regions of the target genes.

Genes in the homeobox family are involved in a wide range of critical activities during development. These activities include directing the formation of limbs and organs along the anterior-posterior axis (meaning the imaginary line that runs from head to tail in animals) and regulating the process by which cells mature to carry out specific functions (differentiation). Some homeobox genes act as tumor suppressors.

The term "hepatic nuclear factor 1 (HNF1)" as used herein refers to a transcriptional activator of many hepatic genes including albumin, α1-antitrypsin, and α- and β-fibrinogen. It is related to the homeobox gene family and is predominantly expressed in liver and kidney. Mice lacking HNF1 fail to thrive and die around weaning after a progressive wasting syndrome with a marked liver enlargement. The transcription rate of genes like albumin and α1-antitrypsin is reduced, while the gene coding for phenylalanine hydroxylase is totally silent, giving rise to phenylketonuria. Pontoglio, M. et al., Cell 4(4): 575-85 (1996).

The term "IL7R" (interleukin-7 receptor subunit alpha (CD127) refers to the gene encoding the receptor for interleukin-7, which also acts as a receptor for thymic stromal lymphopoietin (TSLP).

The term "involucrin" as used herein refers to a component of the keratinocyte crosslinked envelope, is found in the cytoplasm and crosslinked to membrane proteins by transglutaminase.

The term "KRTAP2-3" as used herein refers to the gene encoding keratin associated protein 2-3. In the hair cortex, hair keratin intermediate filaments are embedded in an interfilamentous matrix, consisting of hair keratin-associated proteins (KRTAP), which are essential for the formation of a rigid and resistant hair shaft through their extensive disulfide bond cross-linking with abundant cysteine residues of hair keratins. The matrix proteins include the high-sulfur and high-glycine-tyrosine keratins (By similarity).

The term mCherry" as used herein refers to a 28.8 kDa red fluorescent protein with 256 amino acids.

The term "migration" as used herein refers to movement of a cell from one place or location to another.

The term "NEAT1" as used herein refers to a long noncoding RNA, which is an essential architectural component of paraspeckle nuclear bodies. Neat-1 paraspeckles regulate gene expression through retention of hyperdited mRNAs and/or transcription factors.

The term "NR4A1" as used herein refers to the gene encoding orphan nuclear receptor nuclear receptor subfamily 4 group A member 1. It participates in energy homeostasis by sequestrating the kinase STK11 in the nucleus, thereby attenuating cytoplasmic AMPK activation.

The term "NR4A2" as used herein refers to the gene encoding orphan nuclear receptor nuclear receptor subfamily 4 group A member 2, which is an RNA polymerase II transcriptional regulator important for the differentiation and maintenance of meso-diencephalic dopaminergic (mdDA) neurons during development.

The term "Patched 1" (PTCH1) as used herein refers to the gene encoding the patched-1 protein, which functions as a receptor. It acts as a receptor for sonic hedgehog (SHH), indian hedgehog (IHH) and desert hedgehog (DHH). IT associates with the smoothened protein (SMO) to transduce the hedgehog proteins' signal. Seems to have a tumor suppressor function, as inactivation of this protein is probably a necessary, if not sufficient step for tumorigenesis. Ma, G. et al, Cell Res. 21: 1343-57 (2011).

The term "pericytes" as used herein refer to perivascular cells (cells situated or occurring around a blood vessel) that wrap around capillaries. Pericytes are also known as mural cells, Rouget cells, or, because of their contractile fibers, as vascular smooth muscle cells. Pericytes have roles in angiogenesis, and blood vessel maintenance (Bergers & Song. Neuro Oncol. 2005 October; 7(4): 452-64).

The term "phenotype" as used herein refers to the observable characteristics of a cell, for example, expression of a protein.

The term "PODXL" as used herein refers to the gene encoding podocalyxin-like protein 1, a protein involved in the regulation of both adhesion and cell morphology and cancer progression. Podocalyxin-like protein 1 maintains an open filtration pathway between neighboring foot processes in the podocyte by charge repulsion; acts as a pro-adhesive molecule, enhancing the adherence of cells to immobilized ligands, increasing the rate of migration and cell-cell contacts in an integrin-dependent manner; induces the formation of apical actin-dependent microvilli; is involved in the formation of a preapical plasma membrane subdomain to set up initial epithelial polarization and the apical lumen formation during renal tubulogenesis, and plays a role in cancer development and aggressiveness by inducing cell migration and invasion through its interaction with the actin-binding protein EZR. Larrucea, S. et al., Exptl Cell Res. 314: 2004-15 (2008); Sizemore, S. et al, Cancer Res. 67: 6183-91 (2007). It affects EZR-dependent signaling events, leading to increased activities of the MAPK and PI3K pathways in cancer cells.

The term "proliferate" and its other grammatical forms as used herein means multiplying or increasing in number.

The term "promoter" as used herein refers to a DNA sequence that determines the site of transcription initiation for an RNA polymerase.

The term "reduce" and its various grammatical forms as used herein refer to a diminution, a decrease, an attenuation or abatement of the degree, intensity, extent, size, amount, density or number of occurrences, events or characteristics.

The term "RFP" as used herein refers to red fluorescent protein, which can be excited by the 488 nm or 532 nm laser line and is optimally detected at 588 nm.

RNA interference (RNAi), or Post-Transcriptional Gene Silencing (PTGS) is a conserved biological response to double-stranded RNA that mediates resistance to both endogenous parasitic and exogenous pathogenic nucleic acids, and regulates the expression of protein-coding genes. It is a natural process by which double-stranded RNAs initiate the degradation of homologous RNA; researchers can take advantage of this process to study gene expression. A simplified model for the RNAi pathway is based on two steps, each involving ribonuclease enzyme. In the first step, the trigger RNA (either dsRNA or miRNA primary transcript) is processed into a short, interfering RNA (siRNA) by the RNase II enzymes Dicer and Drosha. In the second step, siRNAs are loaded into the effector complex RNA-induced silencing complex (RISC). The siRNA is unwound during RISC assembly and the single-stranded RNA hybridizes with a mRNA target. Gene silencing is a result of nucleolytic degradation of the targeted mRNA by the RNase H enzyme Argonaute (Slicer).

Gene silencing, however, can also occur not via siRNA-mediated cleavage of targeted mRNA, but rather, via translational inhibition. If the siRNA/mRNA duplex contains mismatches the mRNA is not cleaved; in these cases, direct translational inhibition may occur, especially when high concentrations of siRNA are present. The mechanism of this translation inhibition is not known.

As a result, siRNA can elicit two distinct modes of post-transcriptional repression. Because the requirement for target complementarity is less stringent for direct translational inhibition than for target mRNA cleavage, siRNAs designed for the latter may inadvertently trigger the former in another gene. Therefore, siRNAs designed against one gene may trigger silencing of an unrelated gene.

The term "Scgb1a1" as used herein refers to secretoglobin, family 1a, member 1, or uteroglobin, aevolutionary conserved, steroid-inducible secreted protein that has antiinflammatory and immunomodulatory properties. Mucosal epithelia of virtually all organs that communicate with the external environment express Scgb1a1, and it it present in the blood, urine, and other body fluids (Mukherjee et al. Endocr Rev. 2007 December; 28(7): 707-25).

The term "Sftpc" as used herein refers to pulmonary-associated surfactant protein C, an extremely hydrophobic surfactant protein essential for lung function and homeostasis after birth. It is produced exclusively by AEC2s in the lung. Pulmonary surfactant is a lipid-rich material comprising phospholipids and other surfactant-associated proteins, and prevents lung collapse by reducing surface tension at the air-liquid interface in the alveoli of the lung (Clark & Clark. Semin Fetal Neonatal Med. 2005 June; 10(3): 271-82).

shRNA (short hairpin RNA) sequences offer the possibility of prolonged gene silencing, shRNAs are usually encoded in a DNA vector that can be introduced into cells via plasmid transfection or viral transduction. There are two main categories of shRNA molecules based on their design:

simple stem-loop and microRNA-adapted shRNA. A simple stem-loop shRNA is often transcribed under the control of an RNA Polymerase III (Pol III) promoter [Bartel, D P, MicroRNAs: genomics, biogenesis, mechanism, and function. Cell 116(2):281-297 (2004), Kim, V. N. MicroRNA biogenesis: coordinated cropping and dicing. Nature Reviews, Molecular Cell Biology 6(5):376-385 (2005)]. The 50-70 nucleotide transcript forms a stem-loop structure consisting of a 19 to 29 bp region of double stranded RNA (the stem) bridged by a region of predominantly single-stranded RNA (the loop) and a dinucleotide 3' overhang [Brummelkamp, T. R. et al. (2002) A system for stable expression of short interfering RNAs in mammalian cells. Science 296(5567):550-553; Paddison, P. J. et al. (2002) Stable suppression of gene expression by RNAi in mammalian cells. PNAS 99(3):1443-1448; Paul, C. P. et al. (2002) Effective expression of small interfering RNA in human cells. Nature Biotechnology 20(5):505-508]. The simple stem-loop shRNA is transcribed in the nucleus and enters the RNAi pathway similar to a pre-microRNA. The longer (>250 nucleotide) microRNA-adapted shRNA is a design that more closely resembles native pri-microRNA molecules, and consists of a shRNA stem structure which may include microRNA-like mismatches, bridged by a loop and flanked by 5' and 3' endogenous microRNA sequences [Silva, J. M. et al. (2005) Second-generation shRNA libraries covering the mouse and human genomes. Nature Genetics 37(11):1281-1288.]. The microRNA-adapted shRNA, like the simple stem-loop hairpin, is also transcribed in the nucleus but is thought to enter the RNAi pathway earlier similar to an endogenous pri-microRNA.

The term "small interfering RNAs," which comprises both microRNA (miRNA) and small interfering RNA (siRNA), are small noncoding RNA molecules that play a role in RNA interference. siRNAs are synthesized from double-stranded segments of matched mRNA via RNA-dependent RNA polymerase., and siRNAs regulate the degradation of mRNA molecules identical in sequence to that of the corresponding siRNA, resulting in the silencing of the corresponding gene and the shutting down of protein synthesis. The main mechanism of action of siRNA is the mRNA cleavage function. There are no genes that encode for siRNAs. siRNAs can also silence gene expression by triggering promoter gene methylation and chromatin condensation. miRNAs are synthesized from an unmatched segment of RNA precursor featuring a hairpin turn, and miRNAs are encoded by specific miRNA genes as short hairpin pri-miRNAs in the nucleus. miRNAS are also small noncoding RNAs, but they seem to require only a 7- to 8-base-pair "seed" match between the 5' region of the miRNA and the 3'UTR of the target. While the majority of miRNA targets are translationally repressed, degradation of the target mRNA can also occur. The main mechanism of action of miRNA may be the inhibition of mRNA translation, although the cleavage of mRNA is also an important role (Ross et al. Am J Clin Pathol. 2007; 128(5): 830-36).

The term "aSMA" as used herein refers to alpha-smooth muscle actin, an actin isoform typical of vascular smooth muscle cells, which has been found to play a role in fibroblast contractile activity (Hinz et al. Mol Biol Cell. 2001 September; 12(9): 2730-41).

The term "SOX5" as used herein refers to the gene encoding Sex Determining Region Y-Box 5, a member of the SOX (SRY-related HMB-box) family of transcription factors involved in the regulation of embryonic development and in the determination of cell fate. The encoded protein may form a complex with other proteins, and may play a role in chondrogenesis. It binds specifically to the DNA sequence 5'-AACAAT-3'.

The term "survival rate" as used herein refers to the percentage of a population that are still alive for a certain period of time after treatment.

The term "TAFs" as used herein refers to components of the transcription factor IID (TFIID) complex that is essential for mediating regulation of RNA polymerase transcription. The term "TAF13" as used herein refers to transcription initiation factor TFIID subunit 13, which functions as a component of the DNA-binding general transcription factor complex TFIID. Binding of TFIID to a promoter (with or without TATA element) is the initial step in pre-initiation complex (PIC) formation. TFIID plays a key role in the regulation of gene expression by RNA polymerase II through different activities such as transcription activator interaction, core promoter recognition and selectivity, TFIIA and TFIIB interaction, chromatin modification (histone acetylation by TAF1), facilitation of DNA opening and initiation of transcription. (Birck, C. et al., Cell 94: 239-49 (1998); Sanders, S. L., and Weil, P. A., J Biol. Chem. 275: 13895-900 (2000); Gangloff, Y G et al, Trends Biochem. Sci. 26: 250-257 (2001); Sanders, S. L. et al., Mol Cell. Biol. 22: 6000-6013 (2002); Martinez, E., Plant Mol. Biol. 50: 925-47 (2002)).

The term "TATA box motif" as used herein refers to a consensus sequence found in the promoter region of most genes transcribed by eukaryotic RNA polymerase II, is found about 25 nucleotides before the site of initiation of transcription and has the consensus sequence: 5' TATAAAA 3'. This sequence seems to be important in determining accurately the position at which transcription is initiated.

The term "transcription factor" as used herein refers to a protein that binds to and controls the activity of other genes.

The term "tumor suppressor gene" as used herein refers to a gene whose encoded protein directly or indirectly inhibits progression through the cell cycle and in which a loss-of-function mutation is oncogenic.

The term "VAMP1" refers to the gene encoding vesicle-associated membrane protein 1, which is involved in the targeting and/or fusion of transport vesicles to their target membrane.

The term "XFP" as used herein refers to a general acronym for fluorescent proteins, wherein the "X" is one letter stating the color of the emission.

YBX1 (Y-box binding factor 1) is a gene encoding Y Box binding protein 1, which mediates pre-mRNA alternative splicing regulation. It binds to splice sites in pre-mRNA and regulates splice site selection; binds and stabilizes cytoplasmic mRNA; contributes to the regulation of translation by modulating the interaction between the mRNA and eukaryotic initiation factors. It binds to promoters that contain a Y-box (5-CTGATTGGCCAA-3), such as MDR1 and HLA class II genes, and promotes separation of DNA strands that contain mismatches or are modified by cisplatin. It has endonucleolytic activity and can introduce nicks or breaks into double-stranded DNA (in vitro), and may play a role in DNA repair. It is a component of the CRD-mediated complex that promotes MYC mRNA stability. YBX1 binds preferentially to the 5-[CU]CUGCG-3 motif in vitro. The secreted form acts as an extracellular mitogen and stimulates cell migration and proliferation.

According to one aspect, the described invention provides an isolated population of fibroblasts characterized by a highly invasive phenotype obtained from a subject with idiopathic pulmonary fibrosis. According to one embodiment, the highly invasive phenotype comprises differential expression of one or more of genes selected from the group consisting of Krtap2-3, Involucrin, PODXL, IL7R, GPNMB, VAMP1, and Patched1. According to another embodiment, transcriptional control of the invasive phenotype comprises upregulation of one or more transcriptional factors selected from TAF12, MGA2, and BNC1 and downregulation of one or more transcriptional factors selected from NR4A2 and NEAT1.

According to another aspect, the described invention provides a method for identifying a therapeutic compound effective to reduce invasiveness of fibroblasts characterized by a highly invasive phenotype obtained from a subject with idiopathic pulmonary fibrosis. According to some embodiments, step 1 of the method comprises purifying a population of the fibroblasts characterized by a highly invasive phenotype. The method for purifying the population comprises the steps:

(a) confirming expression of cell surface markers Krtap2-$3^{high}$ and Patched1$^{negative}$ by the invasive fibroblasts by flow cytometry;

(b) isolating and establishing single cell clones based on expression of the cell surface markers;

(c) Transfecting into the IPF fibroblasts one or more mammalian expression pcDNA3-XFP vectors selected from the group of Krtap23-GFP, PODXL-RFP, CD127-CFP and PTCH1-mCherry comprising a promoter of Krtap23, PODXL, CD127, or Patched1 inserted upstream of the fluorescent protein tag;

(d) Selecting positive cells of XFP expression; and (e) Determining cell marker expression, matrix production, proliferation, survival, migration and invasive capacity of the transfected cells, Step 2 of the method comprises contacting the population of fibroblasts characterized by the highly invasive phenotype with a prospective therapeutic compound; and.

Step 3 of the method comprises reducing invasiveness of the fibroblasts as measured in an invasiveness assay, with minimal impact on normal lung fibroblasts with a non-invasive phenotype.

According to some embodiments, the highly invasive phenotype comprises differential expression of one or more of genes selected from the group consisting of Krtap2-3, Involucrin, PODXL, IL7R, GPNMB, VAMP1, and Patched1.

According to some embodiments, transcriptional control of the invasive phenotype comprises upregulation of one or more transcriptional factors selected from TAF12, MGA2, and BNC1 and downregulation of one or more transcriptional factors selected from NR4A2 and NEAT1.

According to some embodiments, the therapeutic compound is a nucleic acid compound. According to some embodiments, the nucleic acid compound is a nucleic acid inhibitor compound. According to some embodiments, the nucleic acid compound is one or more of an siRNA, a DNAzyme, an antisense oligonucleotide, an aptamer or an oligodeoxynucleotide decoy. According to some embodiments, a therapeutic amount of the therapeutic compound is effective to silence gene expression.

[According to some embodiments, the nucleic acid inhibitor is an siRNA. According to some embodiments, the siRNA can be modified to increase stability of the RNA. According to some embodiments, the siRNA is an LNA™-modified siRNA to increase its thermal stability. According to some embodiments, the siRNA is 2'O-methyl modified to improve its stability.

According to some embodiments, the nucleic acid inhibitor is a DNAzyme that is effective to cleave and inactivate TBX4 mRNA. Generally, DNAzymes are catalytically active DNA molecules (see, e.g., Sterna Biologicals, GmbH & Co. KG, www.stema-biologicals.com). DNAzymes of the so-called 10-23 family are specifically characterized by their capability to cleave RNA molecules after appropriate binding. Thus, they directly exert RNA endonuclease activity. 10-23 DNAzymes are single-stranded DNA molecules that consist of two binding domains flanking a central catalytic domain. The latter is composed of 15 deoxynucleotides, the sequence of which is conserved throughout all molecules within this specific DNAzyme class. In contrast, the binding domains are variable and are designed to specifically bind the corresponding target mRNA of interest by Watson-Crick base-pairing.

After binding of a DNAzyme to the corresponding sequence in the target mRNA via the binding domains (step 1), the catalytic domain becomes active and directly cleaves the target mRNA molecule (step 2). After successful cleavage of a target mRNA molecule, the DNAzyme-RNA-complex dissociates and the RNA cleavage products are further degraded by endogenous, intracellular enzymes. The DNAzyme molecule is then available for subsequent binding and cleavage of additional mRNA molecules (step 3).

According to some embodiments, the DNAzyme is modified with a 3'-3' inverted nucleotide at the 3' terminus to prevent exonuclease degradation.

According to some embodiments, the nucleic acid inhibitor is an antisense oligonucleotide. An antisense oligonucleotide (ASO) is a short strand of deoxyribonucleotide analogue that hybridizes with the complementary mRNA in a sequence-specific manner via Watson-Crick base pairing. Formation of the ASO-mRNA heteroduplex either triggers RNase H activity, leading to mRNA degradation, induces translational arrest by steric hindrance of ribosomal activity, interferes with mRNA maturation by inhibiting splicing, or destabilizes pre-mRNA in the nucleus, resulting in downregulation of target protein expression. Chan, J H, Wong, L S, "Clin. Exp. Pharmacol. Physiol. 2006, 33 (5-6): 533-40. According to some embodiments, the antisense oligonucleotide is a DNA antisense oligonucleotide. According to some embodiments, the antisense oligonucleotide is an RNA antisense oligonucleotide. According to some embodiments, the RNA antisense oligonucleotide is phosphorothioate modified to increase its stability and half-life.

According to some embodiments, the nucleic acid inhibitor is an aptamer. Aptamers are a class of small nucleic acid ligands that are composed of RNA or single-stranded DNA oligonucleotides that have high specificity and affinity for their targets. Similar to antibodies, aptamers interact with their targets by recognizing a specific three-dimensional structure. Sun, H. et al., Molec. Therapy Nucleic Acids 2014, 3: e182; doi: 10.1038/mbna.2014.32. According to some embodiments the aptamer is modified with polyethylene glycol to increase its half-life.

According to some embodiment, the nucleic acid inhibitor is an oligodeoxynucleotide (ODN) decoy. A decoy oligonucleotide is a synthesized short DNA sequence that has the same sequence as that found on the portion of the promoter region of a gene where a transcription factor lands. Normally when a transcription factor lands on the promoter region of a gene, transcription of the gene is switched on leading to its expression. However, the decoy oligonucleotide acts as the promoter's "lure", binds with the specific transcription factor in the cell so that the transcription factor cannot land on the genome, and the gene expression is suppressed.

According to some embodiments, the therapeutic compound is a small molecule compound.

According to some embodiments, the therapeutic compound is an antibody. According to some embodiments, the antibody is a synthetic antibody or a fragment thereof that can bind to an antigen with specificity. Examples of antigen-binding antibody fragments include Fab fragments, scFv fragments, and 3G fragments, including single domain and miniaturized antibody therapeutic molecules. See Nelson, A. L., "Antibody fragments," Mabs 2010, 2(1): 77-83).

According to some embodiments, the antibody is a monoclonal antibody or a biologically active fragment thereof. According to some embodiments, the antibody is a chimeric antibody or a biologically active fragment thereof. The term "chimeric antibody" as used herein refers to an antibody made by combining genetic material from a nonhuman source with genetic material from a human. According to some embodiments, the chimeric antibody contains at least 60% human genetic material.

According to some embodiments, the chimeric antibody is a humanized antibody or a biologically active fragment thereof. According to some embodiments, the humanized antibody contains at least about 90% human genetic material.

The term "humanized monoclonal antibodies" refers to antibodies in which the complementarity determining regions, ("CDRs"), which fashion the antibody binding site of a mouse monoclonal antibody, are replaced with a CDR of a human protein, while maintaining the framework and constant regions of the mouse antibody.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those with ordinary skill in the art with a complete disclosure and description of how to make and use the described invention, and are not intended to limit the scope of what the inventors regards as their invention nor are they intended to represent that the experiments below are all or the only experiments performed. Efforts have been made to ensure accuracy with respect to numbers used (e.g., amounts, temperatures, etc.) but some experimental errors and deviation should be accounted for. Unless otherwise indicated, parts are by weight, molecular weight is weight average molecular weight, temperature is in degrees Centigrade, and pressure is at or near atmospheric.

Example 1: Identification and Enrichment of Invasive Fibroblasts with Cell Surface Markers In patients with IPF, a fraction of lung fibroblasts are of the invasive phenotype. Invasive fibroblasts were compared with non-invasive fibroblasts in order to identify a set of genes that were differentially expressed.

An invasiveness assay is an in vitro system for the study of cell invasion of malignant and normal cells. The principle of the assay is that Corning's Matrigel Matrix serves as a reconstituted basement membrane in vitro, occluding the pores of the membrane and blocking non-invasive cells from migrating through the membrane; in contrast, invasive cells secrete proteases that enzymatically degrade the Corning Matrigel Matrix and enable invasion through the membrane pores.

Invasive fibroblasts were identified via a Matrigel® Invasion Assay, using the following procedure:

Materials

Corning BioCoat™ cell culture permeable supports (either 24-well permeable support plates (Corning Cat. No. 354578), or individual permeable supports (Corning Cat. No. 353097)

Falcon® cell culture permeable support companion plates (24 well, Corning Cat. No. 353504)

Corning Matrigel® basement membrane matrix (10 mL vial; standard Corning Matrigel Matrix, Cat. No. 354234; or Growth Factor Reduced Corning Matrigel Matrix, Cat. No. 354230)

Chemoattractant such as 5% fetal bovine serum in tissue culture medium (e.g., Corning Cellgro® Cat. No. 35011-CV)

Bicarbonate based culture medium such as DMEM (serum-free) (Corning cellgro, various formulations)

Tris; Sodium Chloride (coating buffer)

0.2 μm filter unit

Diff-Quik staining kit (Allegiance Cat. No. B4132-1A), or other suitable fixative and stain Microscope with (optional) camera Cotton swabs Sterile forceps Positive displacement pipet Syringes Coating Protocol 1. Coating buffer comprising 0.01M Tris (pH. 8.0) and 0/7% NaCl is prepared and filtered using a 0.2 μm sterile filter unit.

2. A vial containing an aliquot of Matrigel Matrix is thawed on ice at 4° C. Once thawed, the vial is swirled to ensure even dispersion. The vial is kept on ice and handled using sterile technique. The coating buffer should be cooled for two hours in an ice bath in a cold room, or a refrigerator, and any pipets, syringes, or containers that will come in contact with the Matrigel matrix must be chilled prior to use.

3. Coating solution is prepared as follows: Matrigel Matrix (final concentration of 200-300 μg/mL) is mixed with coating butter in a final volume of 2.0 mL. The coating solution is thoroughly mixed with gentle swirling, and the solution in placed on ice at 4° C. This quantity is sufficient to coat twelve 24 well individual permeable supports. Each new syringe is filled halfway with the Matrigel Matrix, expelled, and then filled completely to coat; if positive displacement pipets are used, a larger volume of Matrigel Matrix is necessary to avoid the formation of bubbles.

Permeable Support Coating (Invasion Chambers)

1. Under a hood, the lid from a 24-well permeable support plate is removed (Corning Cat. No. 354578) or individual permeable supports are unwrapped (Corning Cat. No. 353097); sterile forceps are used to transfer the required number of permeable supports into the wells of a Falcon® TC Companion Plate (Corning Cat. No. 353504).
2. Using a sterile syringe or pipet, 0.1 mL of the diluted Matrigel Matrix coating solution is added to each permeable support, taking care to minimize contact of the Matrigel Matrix with the side walls of the permeable support. The coating process is repeated with the remaining permeable supports. Take caution not to introduce air bubbles into the wells. If air bubbles are present, centrifuge the plate to 300×g for 10 minutes at 4° C. in a centrifuge that has been pre-cooled to 4° C.
3. The plates are incubated with the coated permeable supports (invasion chambers) at 37° C. for 2 hours. The remaining liquid (coating buffer) is removed from the permeable support membrane without disturbing the layer of Matrigel Matrix on the membrane just before use. At this point, the coated invasion chambers are ready for use, and the Matrigel Matrix layer should not be allowed to dry out.

Invasion Protocol

1. An equal number of control (uncoated) permeable supports are prepared by using sterile forceps to transfer the permeable supports into empty wells of a Companion Plate.
2. Cells are prepared for the invasion assay according the experimental requirements (e.g., media, serum concentration, confluency). For HT-1080, it is recommended to culture to ~70 to 80% confluency prior to sub-culturing into the invasion chamber.
3. Cell suspensions in culture medium containing 5×104 cells/mL are prepared for the 24 well invasion chambers.
4. Cell suspension (0.5 mL) (2.5×104 cells) is added to each 24 well invasion chamber.
5. Chemoattractant (0.75 mL) is added to the wells of Companion Plate via the access port, taking caution that no air bubbles are trapped beneath the permeable support membranes.
6. The cell invasion chambers are incubated overnight in a humidified tissue culture incubator at 37° C., 5% $CO_2$ atmosphere.

Measurement of Cell Invasion

Removal of Non-Invading Cells

1. A cotton swab moistened with medium is inserted into the top of the Matrigel Matrix coated permeable support (apical side) and gentle but firm pressure is applied while rubbing the area. This is replated with a second swab moistened with medium.

Staining of Cells

Note: The cells on the lower surface of the membrane are stained with Diff-Quik stain. The Diff-Quik kit contains a fixative and two stain solutions, and staining is accomplished by sequentially transferring the permeable supports through the three Diff-Quik solutions and two water rinses. The cell nuclei stain purple and the cytoplasm stains pink.

1. Each solution (0.5 mL) from the Diff-Quik kit is added to three rows of a Companion Plate. Distilled water (0.5 mL) is added to two 24 well plates, or (150 mL) to two beakers.
2. The permeable supports are sequentially transferred through each stain solution and the two plates (or beakers) of water, for approximately 2 minutes in each solution.
3. The permeable support membrane is allowed to air dry.

NOTE: Alternatively, cells may be fixed and stained with 100% methanol and 1% Toluidine Blue, respectively (see below). Alternative staining procedures include fixation followed by hematoxylin and eosin staining or crystal violet.

1. 0.5 mL of 100% methanol is added to the appropriate number of wells of a Companion Plate. In a separate plate, 0.5 mL of 1% Toluidine Blue in 1% borax is added to the appropriate number of wells. Distilled water (0.5 mL) is added to two 24 well plates or (150 mL) to two beakers. Permeable supports are transferred into the methanol for 2 minutes, then into the Toluidine stain for 2 minutes. The permeable support membranes are rinsed in the two 24 well plates or beakers of distilled water to remove excess stain. The permeable support membranes are allowed to air dry.

Counting of Invaded Cells

NOTE: Cell counting can be facilitated by image capture of cells attached to the basal surface through a microscope. Direct counting of the cells is also acceptable.

1. The invaded cells are observed and/or imaged under a microscope at approximately 40× to 100× total magnification, depending on cell density, and the cells are counted in several fields in triplicate.

NOTE: When counting cells, fields in the center of the permeable support membrane as well as fields at the periphery of the membrane should be chosen for an accurate representation of the cell number throughout the membrane. Data is expressed as the percent invasion through the Matrigel® Matrix and membrane relative to the migration of cells through the uncoated membrane.

2. Determine the Percent Invasion:

$$\% \text{ Invasion} = \frac{\text{Mean number of cells invading through Matrigel Matrix coated permeable support membrane}}{\text{Mean number of cells migrating trough uncoated permeable support membrane}} \times 100$$

Figure 5:
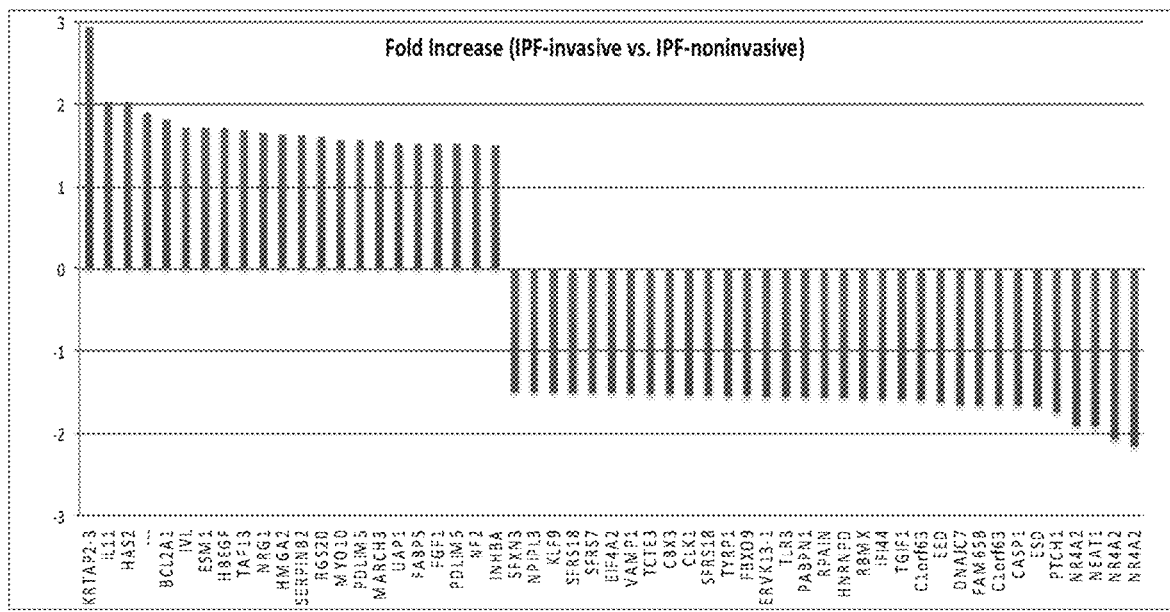
FIG. 5 shows a comparison of gene expression in invasive and non-invasive fibroblasts (normalized, in fold changes relative gene expression (in fold change)) by gene array analysis.
Figure 6:
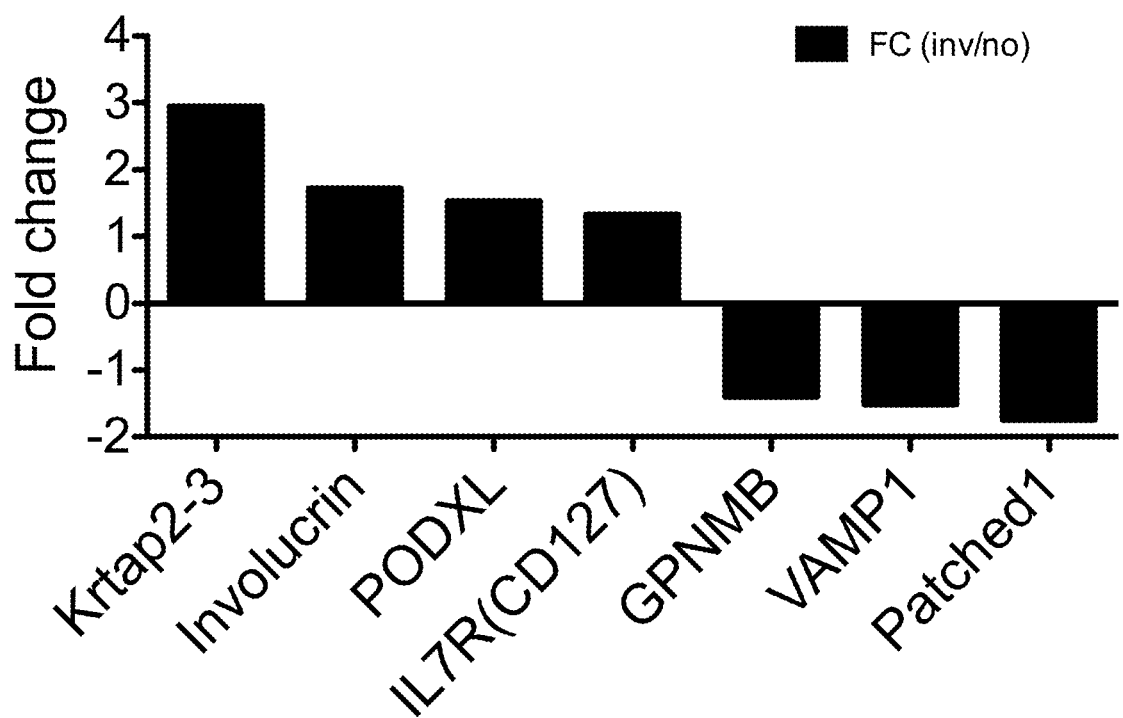
FIG. 6 shows a comparison of relative gene expression (in fold change) of transcription factors in invasive and non-invasive fibroblasts by gene array analysis.

Patterns of gene expression induced during fibroblast invasion have been analyzed. Gene array analysis using Affymetrix gene arrays were carried out on invasive fibroblasts and non-invasive fibroblasts from normal donors and patients with IPF, and a set of genes which were differentially expressed were identified. FIG. 5 illustrates the up-regulation and down-regulation of genes between invasive and non-invasive fibroblasts. Within this set of genes, several putative cell surface markers differentially expressed on invasive and non-invasive fibroblasts were identified. These markers include Krtap2-3, Involucrin, PODXL, CD127 (IL7R), GPNMB, VAMP1 and Patched1. FIG. 6 illustrates the differences in relative gene expression of cell surface molecules between invasive and non-invasive fibroblasts.

Since fibroblasts are heterogeneous, flow cytometry will be used: 1) to confirm the expression of cell surface markers such as Krtap2-3 and Patched1 in invasive fibroblasts from normal and IPF fibroblast lines; and 2) to isolate and establish single cell clones of IPF fibroblasts or normal lung fibroblast lines based on expression of these cell surface markers. Clones with high Krtap2-3 and low/negative Patched1 (Krtap2-3$^{hi}$ and Patched1$^{negative}$) will be enriched by flow sorting and be validated as highly invasive fibroblasts.

As these markers may label a small fraction of fibroblasts, the genetic labeling will be utilized in able to obtain enough cells for drug screening. Krtap23, PODXL, CD127, and Patched1, will be labeled respectively. Mammalian expression pcDNA3-XFP (fluorescent protein tagged) vectors will be used, in which promoters of Krtap23, PODXL, CD127, and Patched1 will replace CMV promoter and will be inserted upstream of XFP (fluorescent protein tags, termed "XFPs") of pcDNA3-XFP vector, respectively. Four XFP vectors will be used, i.e., EGFP, RFP, CFP, and mCherry. Four plasmids, Krtap23-GFP, PODXL-RFP, CD127-CFP, and PTCH1-mCherry will be constructed. The promoters will be isolated by PCR amplification of genomic DNA; vectors will also contain a Neomycin resistant gene which can be used for mammalian selection with G418 in the culture after transfections.

After individual transfection of these vectors into IPF fibroblasts, positive cells and negative cells of XFP expression will be sorted out, and their invasiveness will be determined, respectively. Krtap23-GFP$^{high}$ cells. PODXL-RFP$^{high}$ cells, and CD127-CFP$^{high}$ cells are likely more invasive than their XFP$^{low}$ populations, and PTCH1-mCherry$^{high}$ cells are likely much less invasive than PTCH1-mCherry$^{low}$ cells. Once these characteristics are confirmed, the four vector constructs will be used to co-transfect IPF fibroblasts. Krtap23-GFP$^{high}$PODXL-RFP$^{high}$CD127-CFP$^{high}$PTCH1-mCherry$^{low}$ cells will represent invasive cells. The invasion capacity of these cells will be confirmed. Other phenotype readouts will include cell surface marker expression, matrix production, survival and proliferation, and migration, and invasiveness. These cells will be used for drug screening and antibody immunization.

Example 2: Identification of Transcription Control of Invasive Fibroblasts

Figure 7:
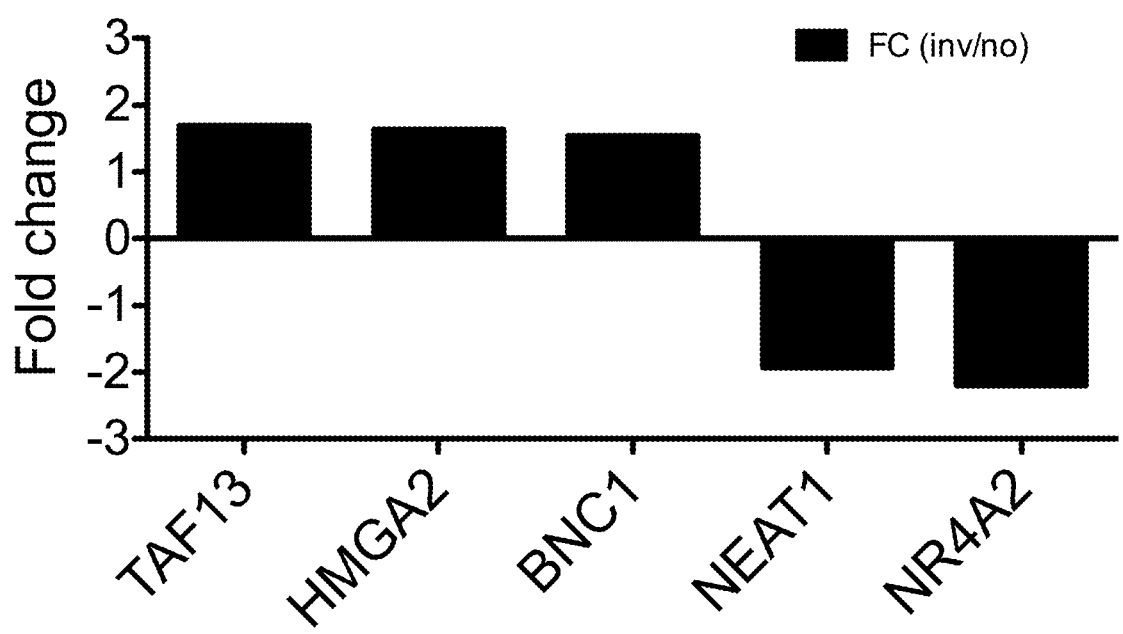
FIG. 7 shows a comparison of relative gene expression (in fold change) of cell surface molecules in invasive and non-invasive fibroblasts by gene array analysis.

Two methods were used to identify transcriptional control for this invasive phenotype. From the Affymetrix gene array analysis, several transcription factors were differentially expressed. Among them, TAF13, HMGA2, and BNC1 were up-regulated, while NR4A2 and NEAT1 were down-regulated. FIG. 7 illustrates the differences in relative gene expression of transcription factors between invasive and non-invasive fibroblasts. Orphan nuclear receptor NR4A1 regulated TGFb signaling and tissue fibrosis Experiments are designed to test whether: 1) TAF13 and NR4A2 are differentially regulated in invasive versus non-invasive fibroblasts; and 2) over-expression of TAF13 and down-regulation of NR4A2 would construct an invasive phenotype. Lentiviral vectors over-expressing TAF13 and shRNA lentiviral vector targeting NR4A2 will be used to infect normal lung fibroblasts. Single cell clones (TAF13$^{high}$hNR4A2$^{low}$) will be isolated and characterized phenotypically and by their gene expression signatures. Phenotype readouts will include cell surface marker expression, matrix production, survival and proliferation, migration, and invasiveness. Clones will be identified based on their invasive gene expression signature, cell surface markers, and invasiveness. Clones will be compared with those based on cell surface markers (Krtap23-GFP$^{high}$PODXL-RFP$^{high}$CD127-CFP$^{high}$PTCH1-mCherry$^{low}$ cells). The experiments will reveal whether the genotypes and phenotypes of these clones identified by these two different methods are similar or comparable.

When genes differentially expressed in invasive versus non-invasive fibroblasts were compared, it was found that within 48 up-regulated genes, 24 can be regulated by YBX1 (Y-box binding factor 1, with a Bayes factor 4), and 28 contain a muscle TATA box motif (with a Bayes factor 2), with GATHER Clustering analysis (http://gather.genome.duke.edu). In 74 down-regulated genes, 36 can be regulated by HNF1 (hepatic nuclear factor 1) (with a Bayes factor 5) and 39 by Sox5 (with a Bayes factor 3). Table 1 illustrates the predicted transcription control of invasive fibroblasts based on Bayes factors. Similar experiments are ongoing to test whether: 1) Ybx1 and Hnf1 are differentially regulated in invasive versus non-invasive fibroblasts; and 2) over-expression of Ybx1 and down-regulation of Hnf1 would construct an invasive phenotype. Lentiviral vectors over-expressing Ybx1 and shRNA lentiviral vector targeting Hnf1 will be used to infect normal lung fibroblasts. Single cell clones (Ybx1$^{high}$ Hnf1$^{low}$) will be isolated and characterized phenotypically and by their gene expression signatures. Phenotype readouts will include cell surface marker expression, matrix production, survival and proliferation, migration, and invasiveness. Clones will be identified based on their invasive gene expression signature, cell surface markers, and invasiveness. Clones will be compared with those based on cell surface markers (Krtap2-3$^{high}$ and Patched1$^{negative}$). The results of these experiments will reveal whether the genotypes and phenotypes of the clones identified by these two different methods are the same or comparable.

TABLE 1

Predicted transcriptional control of invasive phenotype

| TRANSFAC | # Genes | p Value | Bayes Factor |
| --- | --- | --- | --- |
| Up-regulated genes between invasive and non-invasive fibroblasts (48) | | | |
| 1  YBX1, nuclear factor Y (Y-box binding factor) | 20 | 0.0003 | 4 |
| 2  YBX1, nuclear factor Y (Y-box binding factor) | 24 | 0.002 | 3 |
| 3  Muscle TATA box | 28 | 0.005 | 2 |
| 4  v-Myb | 40 | 0.005 | 2 |
| Down-regulated genes between invasive and non-invasive fibroblasts (74) | | | |
| 1  HNF1, Hepatic nuclear factor 1 | 36 | 0.0002 | 5 |
| 2  Retroviral TATA box | 30 | 0.0005 | 4 |
| 3  Sox-5 | 39 | 0.001 | 3 |
| 4  myocyte enhancer factor 2 | 32 | 0.002 | 3 |

Example 3: Drug Screening with Invasive Fibroblasts

Flow cytometric enriched clones (Krtap2-3$^{high}$ and Patched1$^{negative}$) with their parental cells will be subjected to drug screening. The rationale for this screening is to identify compounds that kill highly invasive clones (Krtap2-3$^{high}$ and Patched1$^{negative}$) but with minimal impact to their parental cells and normal lung fibroblasts. The screening will be performed with curated compound libraries at the Molecular Screening Shared Resource at UCLA.

Highly invasive clones (TAF13$^{high}$ NR4A2$^{low}$ and Ybx1$^{high}$ Hnf1$^{low}$, respectively) will be used for drug screening.

The hits will be tested in depth in vitro in normal and IPF fibroblast lines, and readouts will include matrix production, survival and proliferation, migration, and invasiveness. This aims to identify and/or optimize the lead compounds and next further test in murine bleomycin-IPF models in vivo.

A matrix production assay can be used for determining quantitative dye-binding for analysis of sulfated proteoglycans and glycosaminoglycans The test material can be assayed directly when present in a soluble form, or following papain extraction from cells. The dye employed provides a specific label for the sulfated polysaccharide component of proteoglycans or the protein free sulfated glycosaminoglycan chains. An exemplary protocol is as follows:

Papain extraction reagent for sample preparation is prepared by adding 400 mg sodium acetate, 200 mg EDTA, disodium salt, and 40 mg cysteine HCL to 50 ml of a 0.2 ml sodium phosphate buffer, pH 6.4. When dissolved, 250 µl of a papain suspension containing about 5 mg enzyme (Sigma-Aldrich P3125) is added.

Test sample (20-50 mg wet weight) and papain extraction reagent (1 ml) are placed in 1.5 ml labeled microcentrifuge tubes. The tubes are placed in a thermally regulated metal heating block or water bath at 65 C for 3 hours, with occasional mixing. The tubes are centrifuged at 10,000 g for 10 minutes and the supernatant decanted for use with the following protocol.

A set of 1.5 ml microcentrifuge tubes is labeled in duplicate. Reagent blanks (100 µl deionized water or test sample buffer), and GAG standards (aliquots containing 1.0, 2.0, 3.0, 4.0 and 5.0 µg of the reference standard are made up to 100 µl using the same solvent as the Reagent blanks), are used to produce a calibration curve. Test samples contain from 10 µl-100 µl of the test material. The contents of all tubes are adjusted to 100 µl with deionized water or appropriate buffer.

Dye reagent (e.g. Blyscan dye reagent (1.0 ml) containing 1,9 dimethylmethylene blue) is added to each tube. The tubes are capped and mixed by inverting contents. Tubes are placed in a gentle mechanical shaker for 30 minutes to allow a sulfated glycosaminoglycan-dyecomplex to form and precipitate out from soluble unbound dye. The tubes are transferred to a microcentrifuge and spun at 12,000 rpm for 10 minutes. The soluble fraction is removed and the tubes containing insoluble sGAG-dye complex are inverted and rained.

Disociation reagent containing the sodium salt of an anionic surfactant reagent (0.5 ml) is added to the tubes. The tubes are recapped and the bound dye released into solution using a vortex mixer. When all of the bound dye has been dissolved (usually within 10 minutes) the tubes are centrifuged at 12000 rpm for 5 minutes to remove foam.

200 µl of each sample is transferred to individual wells of a 96 microwell plate. The absorbance is measured at 656 nm against reagent blanks.

Example 4: Generation of Monoclonal Antibodies with Invasive Fibroblast Clones

Antibodies are serum proteins the molecules of which possess small areas of their surface that are complementary to small chemical groupings on their targets. These complementary regions (referred to as the antibody combining sites or antigen binding sites) of which there are at least two per antibody molecule, and in some types of antibody molecules ten, eight, or in some species as many as 12, may react with their corresponding complementary region on the antigen (the antigenic determinant or epitope) to link several molecules of multivalent antigen together to form a lattice. As used herein, the term "antibody" includes, by way of example, both naturally occurring and non-naturally occurring antibodies, polyclonal antibodies, monoclonal antibodies, and fragments thereof, chimeric antibodies, wholly synthetic antibodies, and fragments thereof.

The basic structural unit of a whole antibody molecule consists of four polypeptide chains, two identical light (L) chains (each containing about 220 amino acids) and two identical heavy (H) chains (each usually containing about 440 amino acids). The two heavy chains and two light chains are held together by a combination of noncovalent and covalent (disulfide) bonds. The molecule is composed of two identical halves, each with an identical antigen-binding site composed of the N-terminal region of a light chain and the N-terminal region of a heavy chain. Both light and heavy chains usually cooperate to form the antigen binding surface.

Human antibodies show two kinds of light chains, κ and λ; individual molecules of immunoglobulin generally are only one or the other. In normal serum, 60% of the molecules have been found to have κ determinants and 30 percent λ. Many other species have been found to show two kinds of light chains, but their proportions vary. For example, in the mouse and rat, λ chains comprise but a few percent of the total; in the dog and cat, κ chains are very low; the horse does not appear to have any K chain; rabbits may have 5 to 40% λ, depending on strain and b-locus allotype; and chicken light chains are more homologous to λ than κ.

In mammals, there are five classes of antibodies, IgA, IgD, IgE, IgG, and IgM, each with its own class of heavy chain—α (for IgA), δ (for IgD), ε (for IgE), γ (for IgG) and µ (for IgM). In addition, there are four subclasses of IgG immunoglobulins (IgG1, IgG2, IgG3, IgG4) having γ1, γ2, γ3, and γ4 heavy chains respectively. In its secreted form, IgM is a pentamer composed of five four-chain units, giving it a total of 10 antigen binding sites. Each pentamer contains one copy of a J chain, which is covalently inserted between two adjacent tail regions.

All five immunoglobulin classes differ from other serum proteins in that they show a broad range of electrophoretic mobility and are not homogeneous. This heterogeneity—that individual IgG molecules, for example, differ from one another in net charge—is an intrinsic property of the immunoglobulins.

The principle of complementarity, which often is compared to the fitting of a key in a lock, involves relatively weak binding forces (hydrophobic and hydrogen bonds, van der Waals forces, and ionic interactions), which are able to act effectively only when the two reacting molecules can approach very closely to each other and indeed so closely that the projecting constituent atoms or groups of atoms of one molecule can fit into complementary depressions or recesses in the other. Antigen-antibody interactions show a high degree of specificity, which is manifest at many levels. Brought down to the molecular level, specificity means that the combining sites of antibodies to an antigen have a complementarity not at all similar to the antigenic determinants of an unrelated antigen. Whenever antigenic determinants of two different antigens have some structural similarity, some degree of fitting of one determinant into the combining site of some antibodies to the other may occur, and that this phenomenon gives rise to cross-reactions. Cross reactions are of major importance in understanding the complementarity or specificity of antigen-antibody reactions. Immunological specificity or complementarity makes possible the detection of small amounts of impurities/contaminations among antigens.

Monoclonal antibodies (mAbs) can be generated by fusing mouse spleen cells from an immunized donor with a mouse myeloma cell line to yield established mouse hybridoma clones that grow in selective media. A hybridoma cell is an immortalized hybrid cell resulting from the in vitro fusion of an antibody-secreting B cell with a myeloma cell. In vitro immunization, which refers to primary activation of antigen-specific B cells in culture, is another well-established means of producing mouse monoclonal antibodies.

According to some embodiments, flow cytometric enriched single cell clones (Krtap2-3high and Patched1 negative), as well as the clones (TAF13highNR4A2low or Ybx1highHnf1low), will be used as antigens to immunize mice to generate monoclonal antibodies in attempt to obtain antibodies characterized by neutralizing activity towards invasive fibroblast clones. These monoclonal neutralizing antibodies will be tested for their activity in inhibition of fibroblast functions. Readouts will include matrix production, survival and proliferation, migration, and invasiveness.

Diverse libraries of immunoglobulin heavy (VH) and light (Vκ and Vλ) chain variable genes from peripheral blood lymphocytes also can be amplified by polymerase chain reaction (PCR) amplification. Genes encoding single polypeptide chains in which the heavy and light chain variable domains are linked by a polypeptide spacer (single chain Fv or scFv) can be made by randomly combining heavy and light chain V-genes using PCR. A combinatorial library then can be cloned for display on the surface of filamentous bacteriophage by fusion to a minor coat protein at the tip of the phage.

The technique of guided selection is based on human immunoglobulin V gene shuffling with rodent immunoglobulin V genes. The method entails (i) shuffling a repertoire of human λ light chains with the heavy chain variable region (VH) domain of a mouse monoclonal antibody reactive with an antigen of interest; (ii) selecting half-human Fabs on that antigen (iii) using the selected λ light chain genes as "docking domains" for a library of human heavy chains in a second shuffle to isolate clone Fab fragments having human light chain genes; (v) transfecting mouse myeloma cells by electroporation with mammalian cell expression vectors containing the genes; and (vi) expressing the V genes of the Fab reactive with the antigen as a complete IgG1, λ antibody molecule in the mouse myeloma.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method for identifying a therapeutic compound effective to reduce invasiveness of fibroblasts characterized by a highly invasive phenotype obtained from a subject with idiopathic pulmonary fibrosis, wherein such highly invasive phenotype is characterized by upregulation of one or more of genes selected from Krtap2-3, Involucrin, PODXL, IL7R, TAF12, MGA2, and BNC1 and downregulation of one or more genes selected from GPNMB, VAMP1, Patched1, NR4A2 and NEAT1, comprising
   a. Purifying a population of the fibroblasts characterized by the highly invasive phenotype by:
      i. Confirming expression of cell surface markers Krtap2-3$^{high}$ and Patched1$^{negative}$ by the invasive fibroblasts by flow cytometry;
      ii. isolating and establishing single cell clones based on expression of the cell surface markers;
      iii. Transfecting into IPF fibroblasts one or more mammalian expression pcDNA3-XFP vectors selected from the group of Krtap23-GFP, PODXL-RFP, CD127-CFP and PTCH1-mCherry comprising a promoter of Krtap23, PODXL, CD127, or Patched1 inserted upstream of the fluorescent protein tag;
      iv. Selecting positive cells of XFP expression; and
      v. Determining cell marker expression, matrix production, proliferation, survival, migration and invasive capacity of the transfected cells,
   b. Contacting the population of fibroblasts characterized by the highly invasive phenotype with a prospective therapeutic compound; and
   c. Reducing invasiveness of the fibroblasts as measured in an invasiveness assay, with minimal impact on normal lung fibroblasts with a non-invasive phenotype.

2. The method according to claim 1, wherein the therapeutic compound is a short hairpin RNA.

* * * * *

SEQUENCE LISTING

```
<160> NUMBER OF SEQ ID NOS: 1

<210> SEQ ID NO 1
<211> LENGTH: 12
<212> TYPE: DNA
<213> ORGANISM: Homo sapiens

<400> SEQUENCE: 1
ctgattggcc aa                                                     12
```